US012594334B2

(12) United States Patent
Zhang et al.

(10) Patent No.: US 12,594,334 B2
(45) Date of Patent: Apr. 7, 2026

(54) ET$_A$R ANTIBODY, AND PHARMACEUTICAL COMPOSITIONS AND USE THEREOF

(71) Applicant: Gmax Biopharm LLC., Hangzhou (CN)

(72) Inventors: Cheng Zhang, Hangzhou (CN); Kesuo Fan, Hangzhou (CN); Yong Guo, Hangzhou (CN); Chenjiang Yao, Hangzhou (CN); Hua Zhang, Hangzhou (CN); Xiaofeng Wang, Hangzhou (CN); Shuqian Jing, Hangzhou (CN)

(73) Assignee: Gmax Biopharm LLC., Hangzhou (CN)

( * ) Notice: Subject to any disclaimer, the term of this patent is extended or adjusted under 35 U.S.C. 154(b) by 133 days.

(21) Appl. No.: 18/155,644

(22) Filed: Jan. 17, 2023

(65) Prior Publication Data

US 2023/0346932 A1      Nov. 2, 2023

Related U.S. Application Data

(63) Continuation of application No. 16/305,828, filed as application No. PCT/CN2017/086369 on May 27, 2017, now abandoned.

(30) Foreign Application Priority Data

May 31, 2016    (CN) .......................... 201610376600.7
Oct. 27, 2016    (CN) .......................... 201610954533.2

(51) Int. Cl.
| | |
|---|---|
| *A61K 39/395* | (2006.01) |
| *A61K 39/00* | (2006.01) |
| *A61K 47/10* | (2017.01) |
| *A61K 47/12* | (2006.01) |
| *A61K 47/18* | (2017.01) |
| *A61K 47/22* | (2006.01) |
| *A61K 47/26* | (2006.01) |
| *A61P 9/12* | (2006.01) |
| *A61P 11/00* | (2006.01) |
| *A61P 35/00* | (2006.01) |
| *C07K 16/28* | (2006.01) |

(52) U.S. Cl.
CPC ...... *A61K 39/39591* (2013.01); *A61K 39/395* (2013.01); *A61K 47/10* (2013.01); *A61K 47/12* (2013.01); *A61K 47/183* (2013.01); *A61K 47/22* (2013.01); *A61K 47/26* (2013.01); *A61P 9/12* (2018.01); *A61P 11/00* (2018.01); *A61P 35/00* (2018.01); *C07K 16/28* (2013.01); *C07K 16/2869* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,331,647 A | 5/1982 | Goldenberg |
| 4,496,689 A | 1/1985 | Mitra |
| 4,518,584 A | 5/1985 | Mark et al. |
| 4,640,835 A | 2/1987 | Shimizu et al. |
| 4,670,417 A | 6/1987 | Iwasaki et al. |
| 4,737,462 A | 4/1988 | Mark et al. |
| 4,751,180 A | 6/1988 | Cousens et al. |
| 4,791,192 A | 12/1988 | Nakagawa et al. |
| 4,935,233 A | 6/1990 | Bell et al. |
| 4,946,778 A | 8/1990 | Ladner et al. |
| 5,011,912 A | 4/1991 | Hopp et al. |
| 5,457,035 A | 10/1995 | Baum et al. |
| 6,133,426 A | 10/2000 | Gonzalez et al. |
| 6,210,924 B1 | 4/2001 | Hu et al. |
| 6,696,245 B2 | 2/2004 | Winter |
| 6,703,199 B1 | 3/2004 | Koide |
| 6,846,634 B1 | 1/2005 | Tomlinson et al. |
| 10,376,581 B2 | 8/2019 | Zhang et al. |
| 10,869,927 B2 | 12/2020 | Zhang et al. |
| 2002/0055457 A1 | 5/2002 | Janus et al. |
| 2003/0039958 A1 | 2/2003 | Holt et al. |
| 2004/0009507 A1 | 1/2004 | Winter et al. |
| 2004/0038291 A2 | 2/2004 | Tomlinson et al. |
| 2004/0202995 A1 | 10/2004 | Wildt et al. |
| 2005/0202512 A1 | 9/2005 | Tomlinson et al. |
| 2005/0238646 A1 | 10/2005 | Ledbetter et al. |

(Continued)

FOREIGN PATENT DOCUMENTS

| | | |
|---|---|---|
| CN | 101426527 A | 5/2009 |
| CN | 102946861 B | 2/2013 |

(Continued)

OTHER PUBLICATIONS

Ashkenazi et al., "Protection against endotoxic shock by a tumor necrosis factor receptor immunoadhesin," Proc. Natl. Acd. Sci. U.S.A. 88:10535-10539 (1991).

(Continued)

*Primary Examiner* — Marianne P Allen
(74) *Attorney, Agent, or Firm* — .Junhe Law Office, P.C.; James J. Zhu

(57) ABSTRACT

Provided herein are a stable solution formulation of an ET$_A$R antibody, and use thereof in treating, preventing, or alleviating one or more symptoms of pulmonary arterial hypertension or one or more symptoms of cancer of a reproductive organ.

21 Claims, 6 Drawing Sheets

Specification includes a Sequence Listing.

(56) References Cited

U.S. PATENT DOCUMENTS

| | | | |
|---|---|---|---|
| 2009/0162352 A1 | 6/2009 | Adler et al. |
| 2009/0304706 A1 | 12/2009 | Lu et al. |
| 2010/0254985 A1 | 10/2010 | Allan et al. |
| 2011/0171217 A1 | 7/2011 | Badkar et al. |
| 2013/0216525 A1 | 8/2013 | Chen |
| 2014/0186373 A1 | 7/2014 | Cosenza et al. |
| 2018/0256714 A1 | 9/2018 | Zhang et al. |
| 2019/0365894 A1 | 12/2019 | Zhang et al. |

FOREIGN PATENT DOCUMENTS

| | | | |
|---|---|---|---|
| CN | 103728454 A | 4/2014 |
| CN | 104513313 A | 4/2015 |
| CN | 105669863 A | 6/2016 |
| JP | 2008529499 A | 8/2008 |
| JP | 2008280266 A | 11/2008 |
| JP | 2010138165 A | 6/2010 |
| JP | 2010006745 A | 4/2014 |
| JP | 2015522524 A | 8/2015 |
| WO | WO 1993/010151 A1 | 5/1993 |
| WO | WO 1994/010308 A1 | 5/1994 |
| WO | WO 2004/075835 A2 | 9/2004 |
| WO | WO 2006/084264 A2 | 8/2006 |
| WO | WO 2006/099019 A2 | 9/2006 |
| WO | WO 2007/092772 A2 | 8/2007 |
| WO | WO 2011/109365 A2 | 9/2011 |
| WO | WO 2012/045776 A1 | 4/2012 |
| WO | WO 2013/164789 A2 | 11/2013 |
| WO | WO 2017/092375 A1 | 6/2017 |

OTHER PUBLICATIONS

Baron et al., "Co-regulation of two gene activities by tetracycline via a bidirectional promoter," Nucleic Acids Res. 23:3605-3606 (1995).
Barst et al., "Diagnosis and differential assessment of pulmonary arterial hypertension," J. Am. Coll. Cardiol. 43:40S-47S (2004).
Barton et al., "Endothelin: 20 years from discovery to therapy," Can. J. Physiol. Pharmacol. 86:485-498 (2008).
Bauer et al., "A genetic enrichment for mutations constructed by oligodeoxynucleotide-directed mutagenesis," Gene 37:73-81 (1985).
Baum et al., "Molecular characterization of murine and human OX40/OX40 ligand systems: identification of a human OX40 ligand as the HTLV-1-regulated protein gp34," EMBO J. 13:3992-4001 (1994).
Bird et al., "Single-chain antigen-binding proteins," Science 242:423-426 (1988).
Bowie et al., "A method to identify protein sequences that fold into a known three-dimensional structure," Science 253:164-170 (1991).
Brenner et al., "Population statistics of protein structures: lessons from structural classifications," Curr. Op. Struct. Biol. 7:369-376 (1997).
Byrn et al., "Biological properties of a CD4 immunoadhesin," Nature 344:667-670 (1990).
Chou et al., "Conformational parameters for amino acids in helical, beta-sheet, and random coil regions calculated from proteins," Biochemistry 13:211-222 (1974).
Chou et al., "Prediction of protein conformation," Biochemistry 13:222-245 (1974).
Chou et al., "Prediction of the secondary structure of proteins from their amino acid sequence," Adv. Enzymol. Relat. Areas Mol. Biol. 47:45-148 (1978).
Chou et al., "Empirical predictions of protein conformation," Ann. Rev. Biochem. 47:251-276 (1978).
Chou et al., "Prediction of beta-turns," Biophys. J. 26:367-383 (1979).
Craik, "Use of oligonucleotides for site-specific mutagenesis," BioTechniques 3:12-19 (1985).
Crameri et al., "DNA shuffling of a family of genes from diverse species accelerates directed evolution," Nature, 391:288-291 (1998).

De Graaf et al., "Expression of scFvs and scFv fusion proteins in eukaryotic cells," Methods Mol. Biol. 178:379-387 (2002).
Evans et al., "Design of nonpeptidal ligands for a peptide receptor: cholecystokinin antagonists," J. Med. Chem. 30:1229-1239 (1987).
Fanslow et al., "Structural characteristics of CD40 ligand that determine biological function," Semin. Immunol. 6:267-278 (1994).
Gluzman et al., "SV40-transformed simian cells support the replication of early SV40 mutants," Cell 23:175-182 (1981).
Gribskov et al., "Profile analysis: detection of distantly related proteins," Proc. NatL. Acad. Sci. U.S.A. 84:4355-4358 (1987).
Harris, "Processing of C-terminal lysine and arginine residues of proteins isolated from mammalian cell culture," J. Chromatogr. A. 705:129-134 (1995).
Holliger et al., "'Diabodies': small bivalent and bispecific antibody fragments," Proc. Natl. Acad. Sci. U.S.A. 90:6444-6448 (1993).
Holliger et al., "Engineered antibody fragments and the rise of single domains," Nat. Biotechnology, 23:1126-1136 (2005).
Holm et al., "Protein folds and families: sequence and structure alignments," Nucleic Acids Res. 27:244-247 (1999).
Hopp et al., "A short polypeptide marker sequence useful for recombinant protein identification and purification," Bio/Technology 6:1204-1210 (1988).
Hoppe et al., "A parallel three stranded alpha-helical bundle at the nucleation site of collagen triple-helix formation," FEBS Lett. 344:191-195 (1994).
Huston et al, "Protein engineering of antibody binding sites: recovery of specific activity in an anti-digoxin single-chain Fv analogue produced in Escherichia coli," Proc. Natl. Acad. Sci. U.S.A. 85:5879-5883 (1988).
Jelinek et al., "Expression cloning and signaling properties of the rat glucagon receptor," Science 259:1614-1616 (1993).
Jones, "Progress in protein structure prediction," Curr. Opin. Struct. Biol. 7:377-387 (1997).
Korndorfer et al., "Crystallographic analysis of an 'anticalin' with tailored specificity for fluorescein reveals high structural plasticity of the lipocalin loop region," Proteins 53:121-129 (2003).
Kortt et al., "Single-chain Fv fragments of anti-neuraminidase antibody NC10 containing five- and ten-residue linkers form dimers and with zero-residue linker a trimer," Protein Eng. 10:423-433 (1997).
Kortt et al., "Dimeric and trimeric antibodies: high avidity scFvs for cancer targeting," Biomol. Eng. 18:95-108 (2001).
Kriangkum et al., "Bispecific and bifunctional single chain recombinant antibodies," Biomol. Eng. 18:31-40 (2001).
Landschulz et al., "The leucine zipper: a hypothetical structure common to a new class of DNA binding proteins," Science 240:1759-1764 (1988).
Lanitto et al., "Chain shuffling to modify properties of recombinant immunoglobulins," Methods Mol. Biol. 178:303-316 (2002).
Lunde et al., "Troybodies and pepbodies," Biochem. Soc. Trans. 30:500-506 (2002).
Maniatis et al., "Regulation of inducible and tissue-specific gene expression," Science 236:1237-1245 (1987).
Mcmahan et al., "A novel IL-1 receptor, cloned from B cells by mammalian expression, is expressed in many cell types," EMBO J. 10:2821-2832 (1991).
Moult et al., "The current state of the art in protein structure prediction," Curr. Op. Biotech. 7:422-427 (1996).
Millipore Product Information Sheet for rabbit anti-endothelin receptor A affinity purified polyclonal antibody, Catalog No. AB3260, dated Sep. 15, 2011.
Nelson et al., "The endothelin axis: emerging role in cancer," Nat. Rev. Cancer 3:110-113 (2003).
Neylon, "Vascular biology of endothelin signal transduction," Clin. Exp. Pharmacol. Physiol. 26:149-153 (1999).
Nisonoff et al., "Separation of univalent fragments from the bivalent rabbit antibody molecule by reduction of disulfide bonds," Arch. Biochem. Biophys. 89:230-244 (1960).
Nygren et al., "Scaffolds for engineering novel binding sites in proteins," Curr. Opin. Struct. Biol. 7:463-469 (1997).
Patten et al., "Applications of DNA shuffling to pharmaceuticals and vaccines," Curr. Opin. Biotechnol., 8:724-733 (1997).

(56) References Cited

OTHER PUBLICATIONS

Poljak, "Production and structure of diabodies," Structure 2:1121-1123 (1994).

Porter, "The hydrolysis of rabbit y-globulin and antibodies with crystalline papain," Biochem. J. 73:119-126 (1959).

Rasmussen et al., "Isolation, characterization and recombinant protein expression in Veggie-CHO: A serum-free CHO host cell line," Cytotechnology 28:31-42 (1998).

Rizo et al., "Constrained peptides: models of bioactive peptides and protein substructures," Ann. Rev. Biochem. 61:387-418 (1992).

Roque et al., "Antibodies and genetically engineered related molecules: production and purification," Biotechnol. Prog. 20:639-654 (2004).

Schier et al., "Isolation of picomolar affinity anti-c-erbB-2 single-chain Fv by molecular evolution of the complementarity determining regions in the center of the antibody binding site," J. Mol. Biol. 263:551-567 (1996).

Sergre et al., "Receptors for secretin, calcitonin, parathyroid hormone (PTH)/PTH-related peptide, vasoactive intestinal peptide, glucagonlike peptide 1, growth hormone-releasing hormone, and glucagon belong to a newly discovered G-protein-linked receptor family," Trends Endocrinol. Metab. 4:309-314 (1993).

Serasli et al., "Review on bosentan, a dual endothelin receptor antagonist for the treatment of pulmonary arterial hypertension," Recent Pat. Cardiovasc. Drug Discov. 5:184-195 (2010).

Simonneau et al., "Clinical classification of pulmonary hypertension," J. Am. Coll. Cardiol. 43:5S-12S (2004).

Sippl et al., "Threading thrills and threats," Structure 4:15-19 (1996).

Thompson et al., "Affinity maturation of a high-affinity human monoclonal antibody against the third hypervariable loop of human immunodeficiency virus: use of phage display to improve affinity and broaden strain reactivity," J. Mol. Biol. 256:77-88 (1996).

Thomton et al., "Protein structure. Prediction of progress at last," Nature 354:105-106 (1991).

Urlaub et al., "Isolation of Chinese hamster cell mutants deficient in dihydrofolate reductase activity," Proc. Natl. Acad. Sci. U.S.A. 77:4216-4220 (1980).

Vaughan et al., "Human antibodies by design," Nat. Biotechnol. 16:535-539 (1998).

Veber et al., "The design of metabolically-stable peptide analogs," Trends Neurosci. 8:392-396 (1985).

Voss et al., "The role of enhancers in the regulation of cell-type-specific transcriptional control," Trends Biochem. Sci. 11:287-289 (1986).

Walder et al., "Oligodeoxynucleotide-directed mutagenesis using the yeast transformation system," Gene 42:133-139 (1986).

Ward et al., "Binding activities of a repertoire of single immuno-globulin variable domains secreted from *Escherichia coli*," Nature 341:544-546 (1989).

Yang et al., "CDR walking mutagenesis for the affinity maturation of a potent human anti-HIV-1 antibody into the picomolar range," J. Mol. Biol. 254:392-403 (1995).

Marks et al., "By-passing immunization: building high affinity human antibodies by chain shuffling," Biotechnology (N.Y.) 10:779-783 (1992).

Gribskov et al., "Profile analysis," Methods Enzymol. 183:146-159 (1990).

Jpn. J. Clin. Immunol., 2008, vol. 31, No. 6, pp. 424-431.

Journal of Pharmaceutical Science and Technology, Japan, 2012, vol. 72, No. 6, pp. 353-358.

Heart (Sinzo), HEART's Selection, 2013, vol. 45, No. 12, pp. 1503-1511.

Journal of the Japanese Society of Internal Medicine (Nihon Naika Gakkai Zasshi), 2014, vol. 103, No. 9, pp. 2137-2143.

Uchiyama et al., Biophysica et Biochimica Acta 1844:2041-2052 (2014).

Figure 1

| CLONE(#) | CHO-ET$_A$R | CHO-DHFR | CLONE(#) | CHO-ET$_A$R | CHO-DHFR | CLONE(#) | CHO-ET$_A$R | CHO-DHFR |
|---|---|---|---|---|---|---|---|---|
| 1B4 | 0.31 | 0.19 | 11D11 | 0.19 | 0.08 | 25B5 | 0.14 | 0.06 |
| 1D7 | 0.29 | 0.07 | 11I12 | 0.26 | 0.09 | 25G0 | 0.37 | 0.06 |
| 1G8 | 0.15 | 0.07 | 12B1 | 0.28 | 0.06 | 25F9 | 0.14 | 0.06 |
| 1G12 | 0.19 | 0.07 | 12F1 | 0.13 | 0.06 | 25D10 | 0.14 | 0.06 |
| 2H5 | 0.28 | 0.11 | 13B9 | 0.17 | 0.07 | 25C11 | 0.77 | 0.07 |
| 2F12 | 0.41 | 0.26 | 13A12 | 0.34 | 0.07 | 25H10 | 0.39 | 0.06 |
| 3A1 | 0.19 | 0.07 | 14C6 | 0.77 | 0.07 | 26 E4 | 0.13 | 0.07 |
| 3E3 | 0.16 | 0.07 | 14F8 | 0.16 | 0.07 | 27B3 | 0.16 | 0.07 |
| 3F3 | 0.16 | 0.07 | 14A9 | 0.34 | 0.18 | 27D8 | 0.35 | 0.17 |
| 3B7 | 0.16 | 0.09 | 14B9 | 0.37 | 0.06 | 27F12 | 0.18 | 0.08 |
| 3C12 | 0.19 | 0.06 | 14F9 | 0.90 | 0.09 | 28C9 | 0.22 | 0.10 |
| 4B2 | 0.35 | 0.14 | 14 E10 | 0.30 | 0.06 | 30F3 | 0.20 | 0.10 |
| 4C7 | 0.17 | 0.07 | 15F3 | 1.28 | 0.06 | 30A5 | 0.23 | 0.11 |
| 5H1 | 0.14 | 0.07 | 15D7 | 0.16 | 0.06 | 30C11 | 0.14 | 0.07 |
| 5H3 | 0.14 | 0.07 | 15D10 | 0.18 | 0.06 | 30D11 | 0.14 | 0.06 |
| 5C12 | 0.14 | 0.07 | 15G11 | 0.15 | 0.06 | 30H12 | 0.78 | 0.41 |
| 6A1 | 0.71 | 0.07 | 18H4 | 1.07 | 0.07 | 32A7 | 0.84 | 0.50 |
| 6D2 | 0.58 | 0.22 | 18F1 | 0.94 | 0.07 | 32G12 | 0.90 | 0.15 |
| 6D5 | 0.24 | 0.08 | 18F3 | 0.30 | 0.07 | 33F1 | 0.37 | 0.06 |
| 6B6 | 0.49 | 0.25 | 19C12 | 0.48 | 0.07 | 33D6 | 0.39 | 0.08 |
| 6 E8 | 1.76 | 0.41 | 20H1 | 0.30 | 0.06 | 35G3 | 0.53 | 0.07 |
| 8 E2 | 1.33 | 0.06 | 21A1 | 0.91 | 0.07 | 35B8 | 0.61 | 0.07 |
| 8B9 | 0.36 | 0.07 | 21H7 | 0.15 | 0.06 | 36 E9 | 0.29 | 0.06 |
| 8B10 | 0.39 | 0.22 | 21G12 | 0.14 | 0.06 | 36 E11 | 0.34 | 0.06 |
| 8C11 | 0.76 | 0.08 | 22A1 | 0.14 | 0.06 | 36F12 | 1.15 | 0.06 |
| 9D2 | 0.16 | 0.07 | 22C5 | 0.34 | 0.17 | 37B12 | 0.89 | 0.08 |
| 10A2 | 0.10 | 0.07 | 23G1 | 0.15 | 0.09 | 38A9 | 1.75 | 0.06 |
| 10C6 | 0.29 | 0.07 | 23D6 | 0.26 | 0.13 | 38H5 | 1.18 | 0.07 |
| 10B7 | 0.28 | 0.07 | 23 E6 | 1.13 | 0.07 | 40F1 | 0.70 | 0.07 |
| 10A9 | 0.14 | 0.07 | 24C8 | 0.17 | 0.09 | 40F3 | 0.47 | 0.05 |
| 11D1 | 0.25 | 0.07 | 24H10 | 0.17 | 0.08 | 40G2 | 2.22 | 0.08 |
| 11I3 | 0.16 | 0.06 | 24F11 | 0.14 | 0.06 | 40I11 | 0.22 | 0.06 |

| 4 °C | IC$_{50}$ (nM) |
|---|---|
| △ 0 day | 56.3 |
| ■ 3 months | 47.3 |

| 25 °C | IC$_{50}$ (nM) |
|---|---|
| △ 0 day | 55.2 |
| ■ 3 months | 53.7 |

ET$_A$R ANTIBODY, AND PHARMACEUTICAL COMPOSITIONS AND USE THEREOF

CROSS-REFERENCE TO RELATED APPLICATIONS

This application is a continuation of U.S. patent application Ser. No. 16/305,828, filed on Nov. 29, 2018, which is a U.S. National Stage of International Application No. PCT/CN2017/086369, filed May 27, 2017, which claims the benefit of the priority of Chinese Patent Application Nos. 201610954533.2, filed Oct. 27, 2016, and 201610376600.7, filed May 31, 2016; the disclosure of each of which is incorporated herein by reference in its entirety.

SEQUENCE LISTING

This application contains a computer readable Substitute Sequence Listing which has been submitted in XML file format via Patent Center, the entire content of which is incorporated by reference herein in its entirety. The Substitute Sequence Listing XML file submitted via Patent Center is entitled "14254-023-999_SeqList.xml", was created on Jun. 15, 2023, and is 201,958 bytes in size.

FIELD

Provided herein are an ET$_A$R antibody and a pharmaceutical composition thereof, for example, a stable pharmaceutical solution formulation of the ET$_A$R antibody. Also provided herein is a method of treating, preventing, or alleviating one or more symptoms of pulmonary arterial hypertension or one or more symptoms of cancer of a reproductive organ.

BACKGROUND

Endothelin (ET) is a vasoconstriction peptide hormone, important to the homeostasis and regulation of the biological functions of the cardiovascular system. ET is found not only in the endothelium but also in many other tissues and cell types (Barton et al., 2008, *Can. J. Physiol. Pharmacol.* 86:485-498). ET is a 2,400 Da peptide of 21 amino acids, having 2 disulfide bonds at its N-terminus, linking the 1st and 15th cysteine residues and the 3rd and 11th cysteine residues, respectively. Its C-terminus contains hydrophobic amino acid residues. Its N-terminal structure is important for binding to its receptor, while its C-terminal structure is important as to where on the receptor to bind. ET has three isoforms: ET-1, ET-2 and ET-3. They differ by a few amino acid residues. ET-1 plays a major role in the regulation of the biological functions of the cardiovascular system. Upon stimulation, endothelial cells synthesize and release ET-1. ET-1 is mainly regulated at the transcription level.

Endothelin receptors (ETR) has two isoforms: ET$_A$R and ET$_B$R, which belong to the G protein-coupled receptor (GPCR) family. Upon stimulation, ET$_A$R activates membrane Na$^+$/Ca$^{2+}$ exchanger (NCX) and Na$^+$/H$^+$ exchanger (NHE) to increase cellular Ca$^{2+}$ concentrations and to sensitize muscle fibers to Ca', resulting in the constriction of vascular smooth muscle and cardiac muscle (Neylon, 1999, *Clin. Exp. Pharmacol. Physiol.* 26:149-153). Unlike ET$_A$R, ET$_B$R mainly relaxes the vascular smooth muscle cells and cardiac muscle cells (Nelson et al., 2003, *Nat. Rev. Cancer* 3:110-113).

ET$_A$R belongs to GPCR family A and has seven transmembrane domains. The extracellular domain is short and small, and only accounts for about one seventh of the full-length receptor, while a GPCR antibody can only target its extracellular domain. Therefore, the structural feature and naturally low expression level of a GPCR make it difficult to produce biologically active antigens.

Pulmonary arterial hypertension (PAH) is due to the vasoconstriction of the lung or lung related vasculature, resulting in lung artery insufficiency and a compensatory increase in the blood pressure of the heart. On the microscopic scale, there appear to be changes in the small pulmonary arteries, including intimal fibrosis, medial hypertrophy, and plexiform lesions, causing in situ thrombosis of elastic and small pulmonary arteries, and resulting in increased blood circulation resistance in the whole lung vasculature (Simonneau et al., 2004, *J Am. Coll. Cardiol.* 43:5S-12S; Barst et al., 2004, *J. Am. Coll. Cardiol.* 43:40S-47S). PAH is a disease with a fairly high rate of disability or death. It is a devastating disease that severely affects the health of patients and imposes significant burden on society.

The severity of PAH depends on the degree of relevant cardiac deformity, and the common congenital cardiac abnormalities that will result in secondary PAH includes: aortic stenosis, aortopulmonary window, atrial septal defect, complete atrioventricular septal defect, artery coarctation, dilated cardiomyopathy, double outlet right ventricle, hypertrophic cardiomyopathy, mitral stenosis, patent ductus arteriosus, single ventricle, persistent truncus arteriosus, and ventricular septal defect. PAH mainly affects pulmonary arteries and right heart, causing right ventricular hypertrophy, right atrial dilatation, the dilatation of the trunk of the pulmonary artery, and the sparsity of the surrounding pulmonary arterioles. The hypertrophy of endothelial and smooth muscle cells of pulmonary arteriole results in tunica intima fibrosis, tunica media hypertrophy, lumina stenosis, occlusion or distortion, and plexus change. Tunica intima fibrosis and lumina occlusion may also afflict the pulmonary venules.

It has been shown that an ET$_A$R antagonist can effectively block the increase in vascular pressure caused by endothelin to ameliorate PAH symptoms and improve exercise capability and hemodynamics in PAH patients (Serasli et al., 2010, *Recent Pat. Cardiovasc. Drug Discov.* 5:184-95). The antibody provided herein can specifically bind to a human ET$_A$R and attenuate pulmonary arterial pressure in an animal model. It can significantly improve a symptom of PAH in an animal model.

SUMMARY

Provided herein are an ET$_A$R antibody and a pharmaceutical composition thereof, for example, a stable pharmaceutical solution formulation of the ET$_A$R antibody. Also provided herein is a method of treating, preventing, or alleviating one or more symptoms of pulmonary arterial hypertension or one or more symptoms of cancer of a reproductive organ.

The ET$_A$R antibody provided herein comprises 1, 2, 3, 4, 5, or 6 amino acid sequences, wherein each amino acid sequence is independently selected from:

a. light chain CDR1 amino acid sequences: SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30;

b. light chain CDR2 amino acid sequences: SEQ ID NO: 32, SEQ ID NO: 34, SEQ ID NO: 36, SEQ ID NO: 38,

3

SEQ ID NO: 40, SEQ ID NO: 42, SEQ ID NO: 44, SEQ ID NO: 46, and SEQ ID NO: 48;

c. light chain CDR3 amino acid sequences: SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, and SEQ ID NO: 68;

d. heavy chain CDR1 amino acid sequences: SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, and SEQ ID NO: 90;

e. heavy chain CDR2 amino acid sequences: SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, and SEQ ID NO: 114; and f. heavy chain CDR3 amino acid sequences: SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, and SEQ ID NO: 136.

Also provided herein is a pharmaceutical composition comprising an $ET_AR$ antibody provided herein and one or more pharmaceutically acceptable carriers.

Provided herein is a stable pharmaceutical solution formulation of an $ET_AR$ antibody, comprising an $ET_AR$ antibody provided herein and a buffer.

Provided herein is a method of treating, preventing or alleviating one or more symptoms of pulmonary arterial hypertension in a subject, comprising administrating to the subject a therapeutically effective amount of a pharmaceutical composition provided herein, for example, a stable pharmaceutical solution formulation of an $ET_AR$ antibody provided herein.

Provided herein is a method of treating, preventing, or alleviating one or more symptoms of a disease associated with elevated pulmonary arterial pressure in a subject, comprising administrating to the subject a therapeutically effective amount of a pharmaceutical composition provided herein, for example, a stable pharmaceutical solution formulation of an $ET_AR$ antibody provided herein.

Provided herein is a method of treating, preventing, or alleviating one or more symptoms of cancer of a reproductive organ in a subject, comprising administrating to the subject a therapeutically effective amount of a pharmaceutical composition provided herein, for example, a stable pharmaceutical solution formulation of an $ET_AR$ antibody provided herein.

Provided herein is a kit for treating pulmonary arterial hypertension, a disease associated with elevated pulmonary arterial pressure, or cancer of a reproductive organ, comprising a pharmaceutical composition provided herein.

Provided herein is use of a pharmaceutical composition provided herein in the manufacture of a medicament for treating pulmonary arterial hypertension, a disease associated with elevated pulmonary arterial pressure, or cancer of a reproductive organ.

Provided herein is an isolated nucleic acid comprising a polynucleotide sequence encoding an $ET_AR$ antibody provided herein.

Provided herein is a recombinant expression vector comprising a nucleic acid provided herein.

Provided herein is a host cell comprising a vector provided herein.

Provided herein is a method for producing an $ET_AR$ antibody, comprising cultivating a host cell under conditions suitable for expressing an antibody provided herein.

4

BRIEF DESCRIPTION OF THE FIGURES

FIG. 1 shows the ELISA screening results of the supernatants of hybridomas for binding to CHO-DHFR-$ET_AR$ cells (labeled as CHO-$ET_AR$ in the figure). Among them, the $ET_AR$ antibody A-1 (comprising SEQ ID NO: 138 and SEQ ID NO: 166) was obtained from hybridoma clone 15F3.

Figure 3:
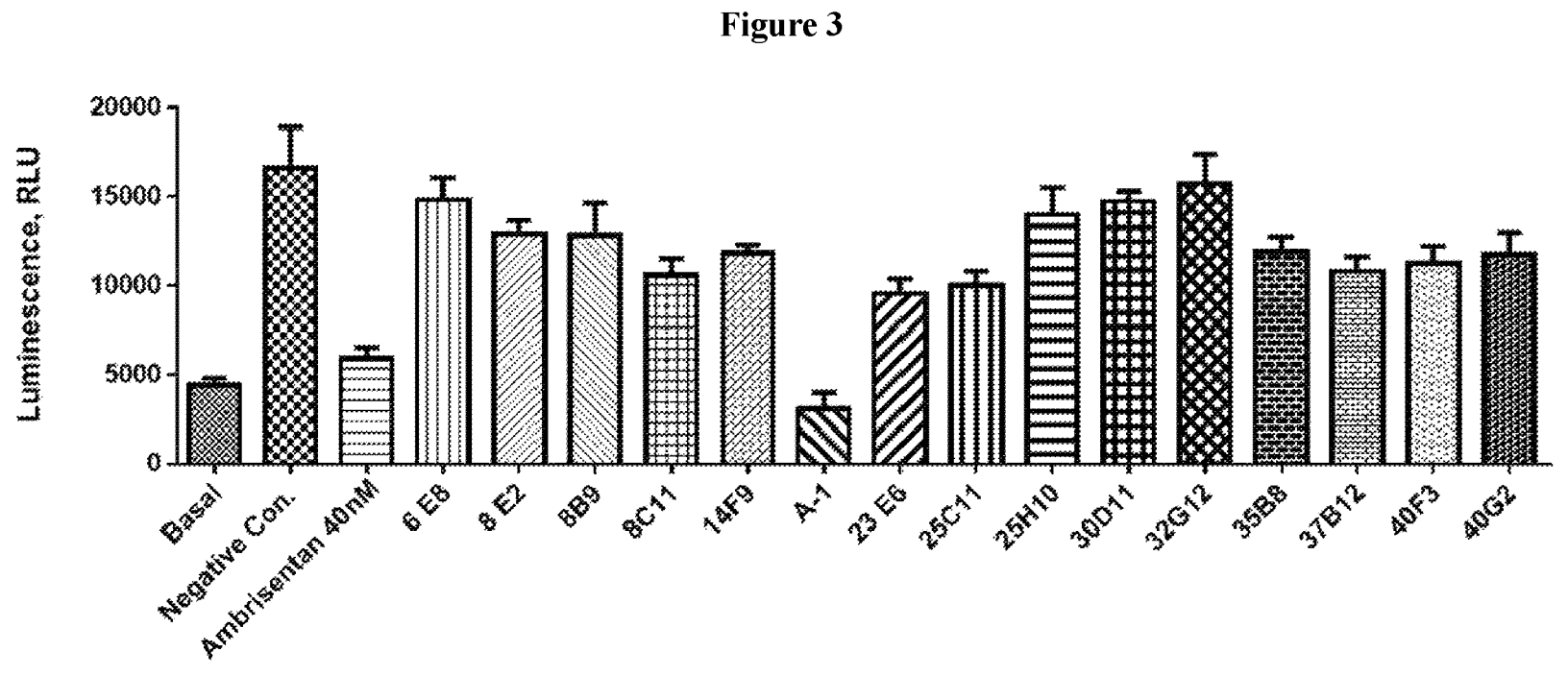

FIG. 3 shows the inhibitory effects of the supernatants of hybridomas on cellular $ET_AR$-mediated $Ca^{2+}$ changes as determined using a calcium flux assay.

Figure 5:
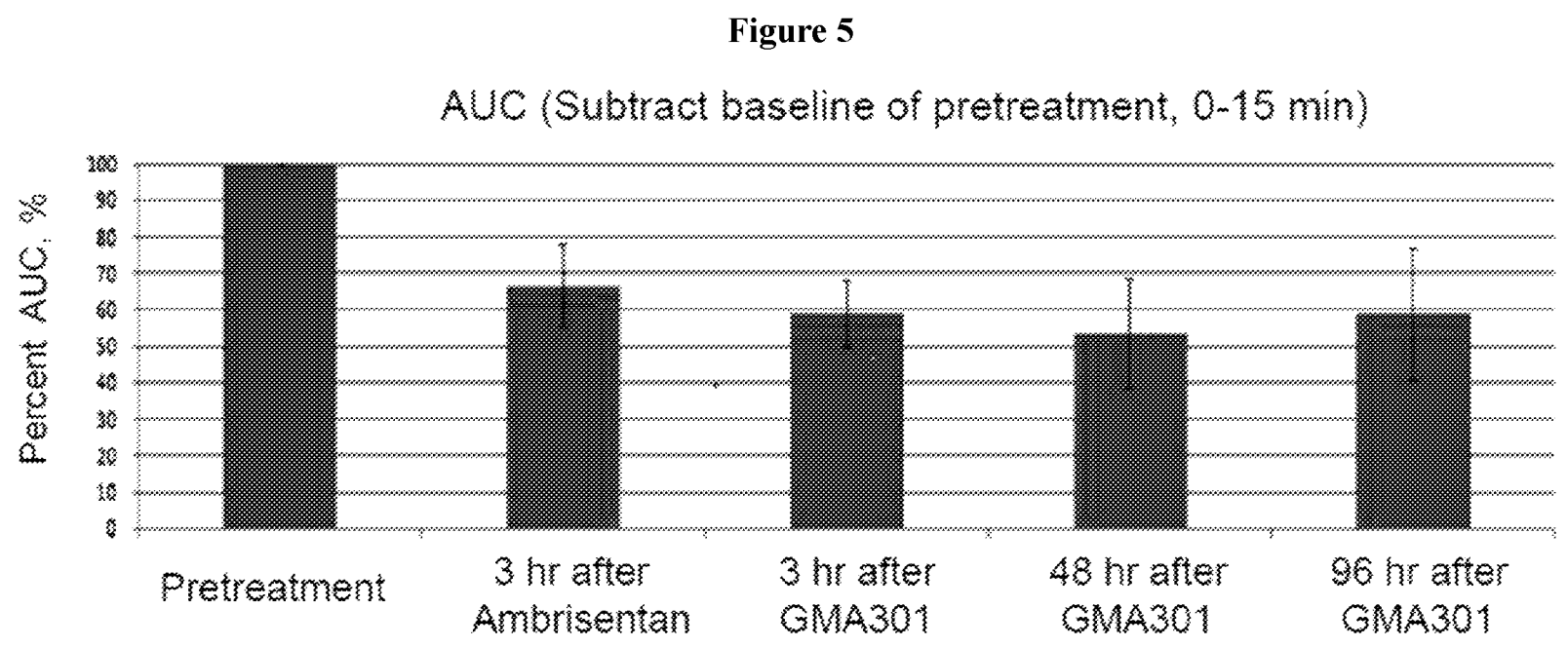

FIG. 5 shows the in vivo activity of the recombinant $ET_AR$ (A-1) in a hypoxia-induced PAH cynomolgus monkey model. A-1 was found to be able to reduce the hypoxia-induced pulmonary systolic pressure significantly, and also to be effective within 96-hr as measured by area under the curve of the pulmonary systolic pressure versus time.

DETAILED DESCRIPTION

Definitions

Figure 2:
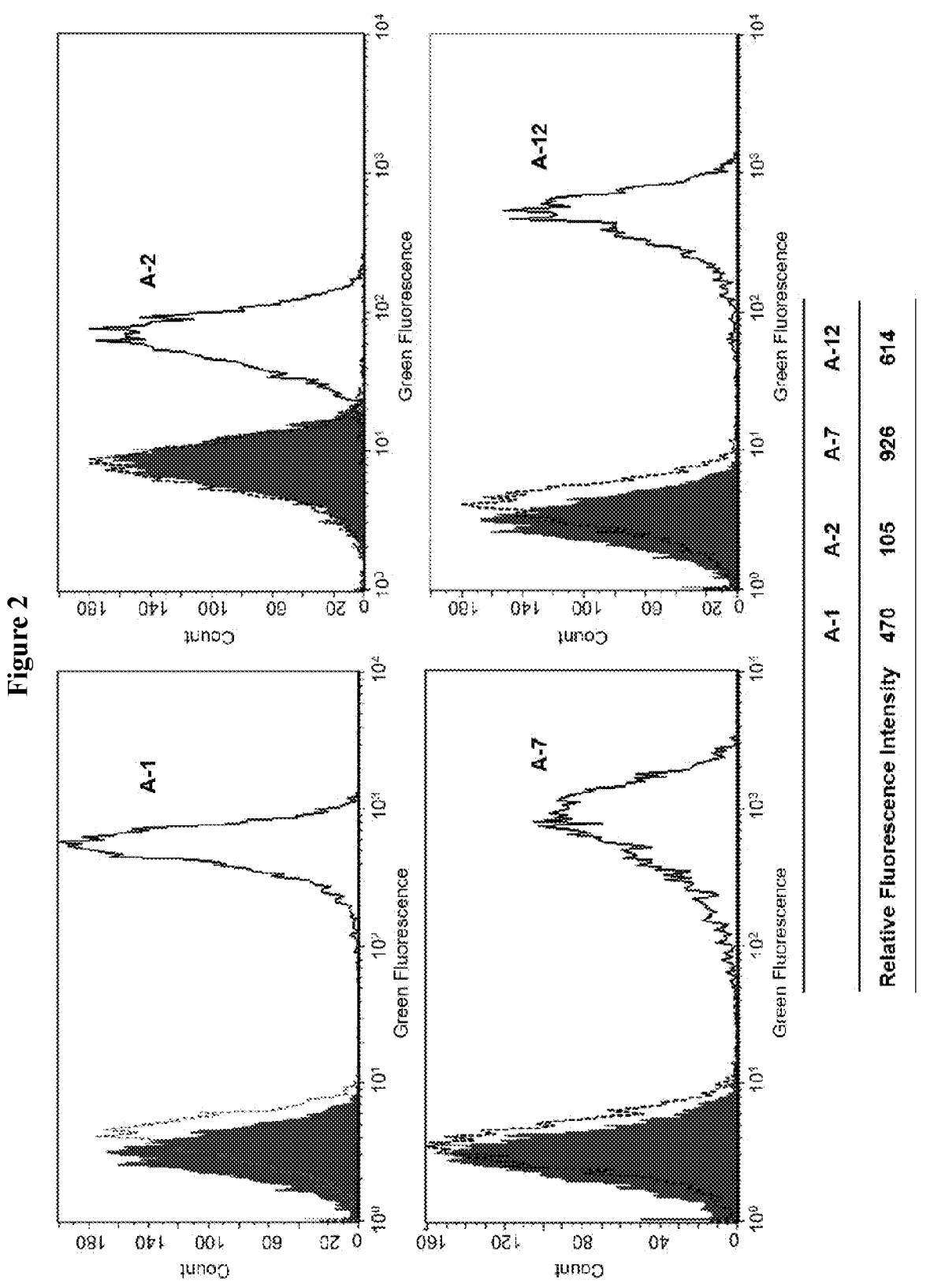
FIG. 2 shows the specific binding of recombinant $ET_AR$ antibodies (A-1, A-2 (comprising SEQ ID NO: 140 and SEQ ID NO: 168), A-7 (comprising SEQ ID NO: 150 and SEQ ID NO: 178), and A-12 (comprising SEQ ID NO: 160 and SEQ ID NO: 188)) to human $ET_AR$ as determined by FACS. The gray peak and the dotted peak are negative controls, the dotted peak representing the binding curve of the $ET_AR$ antibody to CHO-DHFR- and the solid line peak representing the binding curve of the $ET_AR$ antibody to CHO-DHFR-$ET_AR$.
Figure 4:
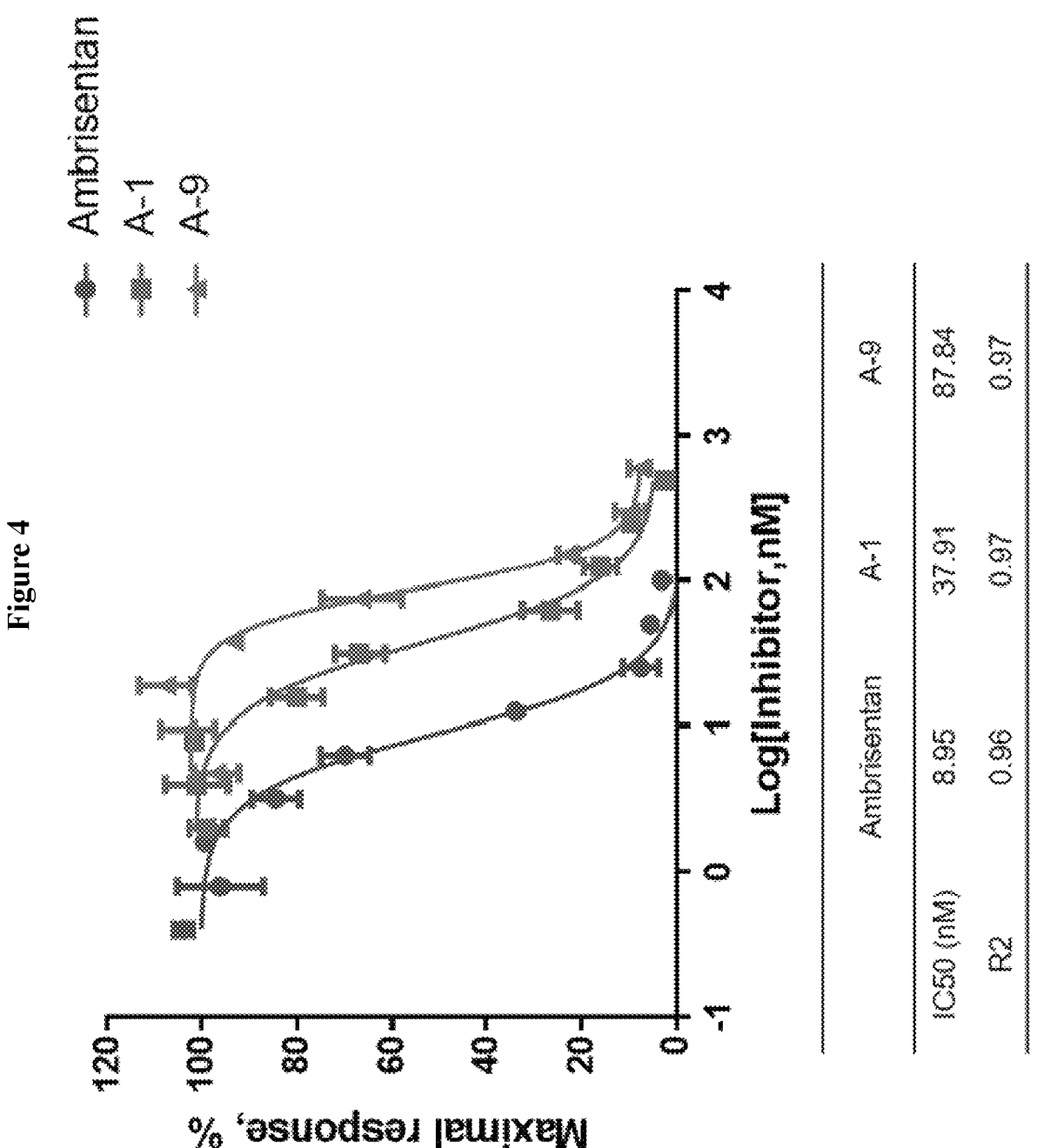
FIG. 4 shows the dose responses of recombinant $ET_AR$ antibodies on the inhibition of human $ET_AR$ as determined using a calcium flux assay ($IC_{50}$=37.91 nM, $R^2$=0.97) (A-1); ($IC_{50}$=87.84 nM, $R^2$=0.97) (A-9 (comprising SEQ ID NO: 154 and SEQ ID NO: 182)).

Unless otherwise defined herein, scientific and technical terms provided herein shall have the meanings that are commonly understood by those of ordinary skill in the art. Generally, nomenclatures and techniques provided herein in connection with pharmacology, biology, biochemistry, cell and tissue culture, molecular biology, immunology, microbiology, genetics and protein and nucleic acid chemistry and hybridization are those well-known and commonly used in the art.

The standard one- or three-letter abbreviations provided herein describe polynucleotide and polypeptide sequences. Unless otherwise specified, polypeptide sequences have their amino termini at the left and their carboxyl termini at the right, and single-stranded nucleic acid sequences and the top strands of double-stranded nucleic acid sequences have their 5' termini at the left and their 3' termini at the right. A particular section of a polypeptide can be designated by amino acid residue numbers such as amino acids 80 to 130, or in combination with the corresponding actual residues such as Lys80 to Lys130. A particular polypeptide or polynucleotide sequence also can be described by showing its differences from a reference sequence.

The terms "peptide" "polypeptide" and "protein" each refer to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post translationally, or otherwise covalently or non-covalently, modified proteins. A peptide, polypeptide, or protein may be monomeric or polymeric.

The term "polypeptide fragment" refers to a polypeptide that has an amino-terminal and/or carboxyl-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

Polypeptides of the disclosure include polypeptides that have been modified in any way and for any reason, for example, to: (1) reduce susceptibility to proteolysis, (2) reduce susceptibility to oxidation, (3) alter susceptibility to form a protein complex, (4) alter binding affinities, and (4) confer or modify other physicochemical or functional properties. Analogs include muteins of a polypeptide. For example, single or multiple amino acid substitutions (e.g., conservative amino acid substitutions) can be made in the naturally occurring sequence (e.g., in the portion of the polypeptide outside the domain(s) forming intermolecular contacts). A "conservative amino acid substitution" is one that does not substantially change the structural characteristics of the parent sequence (e.g., replacement of an amino acid should not break a helix that occurs in the parent sequence, or disrupt other types of secondary structure that characterize the parent sequence or are necessary for its functionality).

A "variant" of a polypeptide comprises an amino acid sequence wherein one or more amino acid residues are inserted into, deleted from and/or substituted into the amino acid sequence relative to another polypeptide sequence. Variants of the disclosure include fusion proteins.

A "derivative" of a polypeptide is a polypeptide that has been chemically modified, e.g., via conjugation to another chemical moiety such as, for example, polyethylene glycol, albumin (e.g., human serum albumin), phosphorylation, and glycosylation.

Unless otherwise indicated, the term "antibody" includes, in addition to antibodies comprising two full-length heavy chains and two full-length light chains, derivatives, variants, fragments, and muteins thereof, examples of which are described below.

An "antibody" is a protein comprising a portion that binds to an antigen and optionally a scaffold or framework portion that allows the antibody to adopt a conformation that promotes the binding of the antibody to the antigen. Examples of antibodies include antibodies, antibody fragments (e.g., an antigen binding portion of an antibody), antibody derivatives, and antibody analogs. The antibody can comprise, for example, an alternative protein scaffold or artificial scaffold with grafted CDRs or CDRs derivatives. Such scaffolds include, but are not limited to, antibody-derived scaffolds comprising mutations introduced, for example, to stabilize the three-dimensional structure of the antibody as well as completely synthetic scaffolds comprising, for example, a biocompatible polymer. See, for example, Korndorfer et al., 2003, *Proteins: Structure, Function, and Bioinformatics,* 53:121-129; Roque et al., 2004, *Biotechnol. Prog.* 20:639-654. In addition, peptide antibody mimetics ("PAMs") can be used, as well as scaffolds based on antibody mimetics utilizing fibronectin components as a scaffold.

An antibody can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxyl terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids. The heavy chain also includes a "D" region of about 10 more amino acids. See generally, Fundamental Immunology, Ch. 7 (Paul, W., ed., 2nd ed. Raven Press, N.Y. (1989)) (incorporated herein by reference in its entirety for all purposes). The variable regions of each light/heavy chain pair form the antibody binding site such that an intact immunoglobulin has two binding sites.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise regions FR1, CDR1, FR2, CDR2, FR3, CDR3 and FR4. The assignment of amino acids to each region is in accordance with the definitions of Kabat et al. in Sequences of Proteins of Immunological Interest, 5th Ed., US Dept. of Health and Human Services, PHS, NIH, NIH Publication No. 91-3242, 1991.

Unless otherwise specified, an "antibody" refers to an intact immunoglobulin or to an antigen binding portion thereof that competes with the intact antibody for specific binding. Antigen binding portions can be produced by recombinant DNA techniques or by enzymatic or chemical cleavage of intact antibodies. Antigen binding portions include, inter alia, Fab, Fab', F(ab')2, Fv, domain antibodies (dAbs), fragments including complementarity determining regions (CDRs), single-chain antibodies (scFv), chimeric antibodies, diabodies, tribodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_{H1}$ regions; a F(ab')2 fragment is a bivalent fragment having two Fab fragments linked by a disulfide bridge at the hinge region; a Fd fragment has the $V_H$ and $C_{H1}$ regions; and a dAb fragment has a $V_H$ region, a $V_L$ region, or an antigen-binding fragment of a $V_H$ or $V_L$ region (U.S. Pat. Nos. 6,846,634, 6,696,245, US application Pub. Nos. 05/0202512, 04/0202995, 04/0038291, 04/0009507, 03/0039958, Ward et al., 1989, *Nature* 341:544-546).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, *Science* 242:423-26 and Huston et al., 1988, *Proc. Natl. Acad. Sci. USA* 85:5879-83). Diabodies are bivalent antibodies comprising two polypeptide chains, wherein each polypeptide chain comprises $V_H$ and $V_L$ regions joined by a linker that is too short to allow for pairing between two regions on the same chain, thus allowing each region to pair with a complementary region on another polypeptide chain (see, e.g., Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and frame work regions (FR) of a given antibody can be identified using the system described by Kabat et al. in Sequences of Proteins of Immunological Interest, 5th Ed., US Dept. of Health and Human Services, PHS, NIH, NIH Publication no. 91-3242, 1991. One or more CDRs can be incorporated into a molecule either covalently or noncovalently to make it an antibody. An antibody can incorporate the CDR(s) as part of a larger polypeptide chain, can covalently link the CDR(s) to another polypeptide chain, or can incorporate the CDR(s) noncovalently. The CDRs permit the antibody to specifically bind to a particular antigen of interest.

An antibody can have one or more binding sites. If there are more than one binding sites, the binding sites can be identical to one another or can be different. For example, a naturally occurring human immunoglobulin typically has two identical binding sites, while a "bispecific" or "bifunctional" antibody has two different binding sites.

The term "murine antibody" includes all antibodies that have one or more variable and constant regions derived from a murine immunoglobulin sequence.

The term "humanized antibody" refers to an antibody that produced by grafting the complementarity determining region sequence of a murine antibody molecule into a human antibody variable region framework.

The term "antigen-binding domain," "antigen-binding region," or "antibody-binding site" is a portion of an antibody that comprises amino acid residues (or other portion) interacting with an antigen and contributing to the specificity and affinity of the antibody for the antigen. For antibodies that specifically bind to their antigen, this will include at least a portion of at least one of its CDR regions.

The term "epitope" is the portion of a molecule that is bound by an antibody (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antibody).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody of the invention, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps and without unpaired nucleotides at the 5' or the 3' end of either sequences. A polynucleotide is "complementary" to another polynucleotide if the two polynucleotides can hybridize to one another under moderately stringent conditions. Thus, a polynucleotide can be complementary to another polynucleotide without being its complement.

The term "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vectors that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in EnZymology 185, Academic Press, San Diego, Calif and Baron et al., 1995, *Nucleic Acids Res.* 23:3605-06.

The term "host cell" is a cell that can be used to express a nucleic acid, e.g., a nucleic acid of the invention. A host cell can be a prokaryote, for example, *E. coli*, or it can be an eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Endothelin Receptor

Endothelin A receptor (ET$_A$R) belongs to family A of 7-transmembrane receptors that are coupled to one or more intracellular signaling pathways via heterotrimeric guanine nucleotide-binding proteins (G proteins) (Jelinek et al., 1993, *Science* 259:1614-1616, Segre et al., 1993, *Trends Endocrinol. Metab.* 4:309-314). As used herein, "endothelin receptor" and "ET$_A$R" are used interchangeably.

In one embodiment, the antibody provided herein can be selected to bind to membrane bound endothelin receptors as expressed on cells, and inhibit or block endothelin signaling through the endothelin receptors. In one embodiment, the antibody provided herein specifically binds to the human endothelin receptor. In a further embodiment, the antibody binding to the human endothelin receptor can also bind to the endothelin receptors of other species, e.g., rat. The examples below provide one method of generating murine antibodies which bind to human membrane-bound endothelin receptors, and in a further embodiment, bind to endothelin receptors of other species.

The polynucleotide and polypeptide sequences for several species of the endothelin receptors are known. SEQ ID NO: 1-SEQ ID NO: 6 present sequences for human, monkey, and rat. The sequence data were obtained from the GeneBank database of the National Center for Biotechnology Information.

Endothelin a Receptor:

Human (*Homo sapiens*) polynucleotides (SEQ ID NO: 1); accession number: 563938.

Human (*Homo sapiens*) amino acid (SEQ ID NO: 2); accession number: AAB20278.

Cynomolgus (*Homo sapiens*) polynucleotides (SEQ ID NO: 3); accession number: JV635771.

Cynomolgus (*Homo sapiens*) amino acid (SEQ ID NO: 4); accession number: AFJ71111.

Rat (*Rattus norvegicus*) polynucleotides (SEQ ID NO: 5); accession number: M60786.

Rat (*Rattus norvegicus*) amino acid (SEQ ID NO: 6); accession number: AAA41114. Endothelin receptor A (ET$_A$R) antibody In one embodiment, an ET$_A$R antibody (for example, a full-length antibody, antibody fragment, antibody derivative, antibody variant, and antibody mutein) is provided herein.

In one embodiment, the ET$_A$R antibody provided herein comprises 1, 2, 3, 4, 5, or 6 amino acid sequences, wherein each amino acid sequence is independently selected from the amino acid sequences listed below:

a. light chain CDR1 amino acid sequences: SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30;

b. light chain CDR2 amino acid sequences: SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, and SEQ ID NO: 48;

c. light chain CDR3 amino acid sequences: SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, and SEQ ID NO: 68;

d. heavy chain CDR1 amino acid sequences: SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, and SEQ ID NO: 90;

e. heavy chain CDR2 amino acid sequences: SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, and SEQ ID NO: 114; and f. heavy chain CDR3 amino acid sequences: SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, and SEQ ID NO: 136.

Table 1 lists light chain CDR amino acid sequences of the ET$_A$R antibodies provided herein, as well as their polynucleotides coding sequences. Table 2 lists heavy chain CDR amino acid sequences of the ET$_A$R antibodies provided herein, as well as their polynucleotides coding sequences.

TABLE 1

| light chain CDR amino acid sequences and polynucleotide coding sequences | | | |
|---|---|---|---|
|  | CDR1 | CDR2 | CDR3 |
| A-1 Nucleic Acid | agggccagtcagaacattggc acaagcatacac (SEQ ID NO: 7) | tatgcttctaagtctatatct (SEQ ID NO: 31) | caacatagttatagcttcccg tggacg (SEQ ID NO: 49) |
| A-1 Amino Acid | RASQNIGTSIH (SEQ ID NO: 8) | YASKSIS (SEQ ID NO: 32) | QHSYSFPWT (SEQ ID NO: 50) |
| A-2 Nucleic Acid | cgagcaagtgaaaatatttac agttatttagca (SEQ ID NO: 9) | aatgcaaaaaccttagcagaa (SEQ ID NO: 33) | cagcatcattatggtattccg ttcacg (SEQ ID NO: 51) |
| A-2 Amino Acid | RASENIYSYLA (SEQ ID NO: 10) | NAKTLAE (SEQ ID NO: 34) | QHHYGIPFT (SEQ ID NO: 52) |
| A-3 Nucleic Acid | cagagcctctttgatattgat ggaaagacatatttgaat (SEQ ID NO: 11) | ctggtgtctgaattggactct (SEQ ID NO: 35) | tggcaaggtacacattttccg ctcacg (SEQ ID NO: 53) |

TABLE 1-continued

| light chain CDR amino acid sequences and polynucleotide coding sequences | | | |
|---|---|---|---|
| | CDR1 | CDR2 | CDR3 |
| A-3 Amino Acid | QSLFDIDGKTYLN (SEQ ID NO: 12) | LVSELDS (SEQ ID NO: 36) | WQGTHFPLT (SEQ ID NO: 54) |
| A-4 Nucleic Acid | cgggcaagtcaggacattggt ggtagcttaaac (SEQ ID NO: 13) | gccacatccagcttagattct (SEQ ID NO: 37) | ctacaatatgctagttctccg tatacg (SEQ ID NO: 55) |
| A-4 Amino Acid | RASQDIGGSLN (SEQ ID NO: 14) | ATSSLDS (SEQ ID NO: 38) | LQYASSPYT (SEQ ID NO: 56) |
| A-5 Nucleic Acid | agggccagccagactattagc gacttcttacac (SEQ ID NO: 15) | tatgcttcccaatccatctct (SEQ ID NO: 39) | caaagtggtaacacctttccg tggacg (SEQ ID NO: 57) |
| A-5 Amino Acid | RASQTISDFLH (SEQ ID NO: 16) | YASQSIS (SEQ ID NO: 40) | QSGNTFPWT (SEQ ID NO: 58) |
| A-6 Nucleic Acid | agggcaagtgaggacatacac actcaattagcc (SEQ ID NO: 17) | ggtgcagccagtttgaaaagt (SEQ ID NO: 41) | caacagtataggagtattccg tggacg (SEQ ID NO: 59) |
| A-6 Amino Acid | RASEDIIITQLA (SEQ ID NO: 18) | GAASLKS (SEQ ID NO: 42) | QQYRSIPWT (SEQ ID NO: 60) |
| A-7 Nucleic Acid | agatctagtcagtacattgtt catagtactggaaccacctat ttagaa (SEQ ID NO: 19) | aaagtttccaaccgattttct (SEQ ID NO: 43) | tttcaaggttcacattttcca ttcacg (SEQ ID NO: 61) |
| A-7 Amino Acid | RSSQYIVHSTGTTYLE (SEQ ID NO: 20) | KVSNRFS (SEQ ID NO: 44) | FQGSHFPFT (SEQ ID NO: 62) |
| A-8 Nucleic Acid | agatctagtcattaccttgtt catgataacggaaacacctat gttgaa (SEQ ID NO: 21) | aaggtttccaaccgattttct (SEQ ID NO: 43) | tttcaaggttcacatttccca ttcacg (SEQ ID NO: 63) |
| A-8 Amino Acid | RSSHYLVHDNGNTYVE (SEQ ID NO: 22) | KVSNRFS (SEQ ID NO: 44) | FQGSHFPFT (SEQ ID NO: 62) |
| A-9 Nucleic Acid | agatctagtcagaacattgtc catagtactggaaacacctat ttagaa (SEQ ID NO: 23) | aaagtttccaaccgattttct (SEQ ID NO: 43) | tttcaaggttcacattttcca ttcacg (SEQ ID NO: 61) |
| A-9 Amino Acid | RSSQNIVHSTGNTYLE (SEQ ID NO: 24) | KVSNRFS (SEQ ID NO: 44) | FQGSHFPFT (SEQ ID NO: 62) |
| A-10 Nucleic Acid | agtgtcagctcaagtgtaagt tcatacac (SEQ ID NO: 25) | gacacatccaaactggcttct (SEQ ID NO: 45) | caccagtggagtactaaccca (SEQ ID NO: 63) |
| A-10 Amino Acid | SVSSSVSYIH (SEQ ID NO: 26) | DTSKLAS (SEQ ID NO: 46) | HQWSTNPPT (SEQ ID NO: 64) |
| A-11 Nucleic Acid | agtgccagctcaagtgtaagt tacatgtgc (SEQ ID NO: 27) | gacacatccaaactggcttct (SEQ ID NO: 45) | cagcagtggagtagtaaccca cccacg (SEQ ID NO: 65) |
| A-11 Amino Acid | SASSSVSYMC (SEQ ID NO: 28) | DTSKALS (SEQ ID NO: 46) | QQWSSNPPT (SEQ ID NO: 66) |
| A-12 Nucleic Acid | cagggcattaacaattat (SEQ ID NO: 29) | tatacatcaactttacagtca (SEQ ID NO: 47) | cagcagtttagtaaacttcgg aca (SEQ ID NO: 67) |
| A-12 Amino Acid | QGINNY (SEQ ID NO: 30) | YTSTLQS (SEQ ID NO: 48) | QQFSKLRT (SEQ ID NO: 68) |

TABLE 2

| | heavy chain CDR amino acid sequences and polynucleotide coding sequences | | |
|---|---|---|---|
| | CDR1 | CDR2 | CDR3 |
| A-1 Nucleic Acid | gggttctcactgaccacttctggcttgggtgttgcc (SEQ ID NO: 69) | cacatttggtcggatggtgacacgcgctattacccagccctgaagaac (SEQ ID NO: 91) | atgaaggatgatagtctttactttgacaac (SEQ ID NO: 115) |
| A-1 Amino Acid | GFSLTTSGLGVA (SEQ ID NO: 70) | HIWSDGDTRYYPALKN (SEQ ID NO: 92) | MKDDSLYFDN (SEQ ID NO: 116) |
| A-2 Nucleic Acid | ggctacacctttactagctactggatacac (SEQ ID NO: 71) | tacattaatcctgacactgattatagtgagtacaat (SEQ ID NO: 93) | gcaagtgctggttattattttttttgacttc (SEQ ID NO: 117) |
| A-2 Amino Acid | GYTFTSYWIH (SEQ ID NO: 72) | YINPDTDYSEYN (SEQ ID NO: 94) | ASAGYYFFDF (SEQ ID NO: 118) |
| A-3 Nucleic Acid | ggcctcaacattaaagacatctatattcac (SEQ ID NO: 73) | aggattgatcctgcgaacggtaagaactgcatatgac (SEQ ID NO: 95) | ggtaggggggcccac (SEQ ID NO: 119) |
| A-3 Amino Acid | GLNIKDIYIH (SEQ ID NO: 74) | RIDPANGKTAYD (SEQ ID NO: 96) | GRGAH (SEQ ID NO: 120) |
| A-4 Nucleic Acid | ggttactcattcaccaactactggatacac (SEQ ID NO: 75) | atgattgatccttccgatgctgaaactgggttaaat (SEQ ID NO: 97) | gcaagaattggcgattactataatatggactac (SEQ ID NO: 121) |
| A-4 Amino Acid | GYSFTNYWIH (SEQ ID NO: 76) | MIDPSDAETGLN (SEQ ID NO: 98) | ARIGDYYNMDY (SEQ ID NO: 122) |
| A-5 Nucleic Acid | ggattcactttcagtgactatcccatgtct (SEQ ID NO: 77) | gttagtgatggtggtggttccacc (SEQ ID NO: 99) | acaagacatgcttcctactatagctacgaccattctatggactac (SEQ ID NO: 123) |
| A-5 Amino Acid | GFTFSDYPMS (SEQ ID NO: 78) | VSDGGGST (SEQ ID NO: 100) | TRHASYYSYDHSMDY (SEQ ID NO: 124) |
| A-6 Nucleic Acid | ggattcactttcagtagctttggcatgtct (SEQ ID NO: 79) | attagtagtgctggtagtttcacc (SEQ ID NO: 101) | gcaagacgggggtacgacgttgggtgctttgaccac (SEQ ID NO: 125) |
| A-6 Amino Acid | GFTFSSFGMS (SEQ ID NO: 80) | ISSAGSFT (SEQ ID NO: 102) | ARRGYDVGCFDH (SEQ ID NO: 126) |
| A-7 Nucleic Acid | ggattcactttcagtacctatggcatgtct (SEQ ID NO: 81) | accattaatactaatggtggtaccacctattatcgagacagtgtgaagggc (SEQ ID NO: 103) | gcaagagactacggggctatggactac (SEQ ID NO: 127) |
| A-7 Amino Acid | GFTFSTYGMS (SEQ ID NO: 82) | TINTNGGTTYYRDSVKG (SEQ ID NO: 104) | ARDYGAMDY (SEQ ID NO: 128) |
| A-8 Nucleic Acid | ggattcactttcagtacctatggcatgtct (SEQ ID NO: 81) | accataaatactaatggtggtaacacctattattcagacaatgtgaagggc (SEQ ID NO: 105) | gcaagagactacggggctatggactac (SEQ ID NO: 127) |
| A-8 Amino Acid | GFTFSTYGMS (SEQ ID NO: 82) | TINTNGGNTYYSDNVKG (SEQ ID NO: 106) | ARDYGAMDY (SEQ ID NO: 128) |
| A-9 Nucleic Acid | ggattcactttcagtagttatggcatgtct (SEQ ID NO: 83) | accattagtactaatggtgccaccgccaattatccagacagtgtgaagggc (SEQ ID NO: 107) | gcaactgaaaagggagctatgggctac (SEQ ID NO: 129) |
| A-9 Amino Acid | GFTFSSYGMS (SEQ ID NO: 84) | TISTNGATANYPDSVKG (SEQ ID NO: 108) | ATEKGAMGY (SEQ ID NO: 130) |
| A-10 Nucleic Acid | gggttttcactgaccacttctggtatgggtgtaggc (SEQ ID NO: 85) | cacatttggtgggatgatgataagtactataatccatccctgaagagc (SEQ ID NO: 109) | gctcgaagaactgagactatgattacgacagtgctatattactatgctatggactac (SEQ ID NO: 131) |
| A-10 Amino Acid | GFSLTTSGMGVG (SEQ ID NO: 86) | HIWWDDDKYYNPSLKS (SEQ ID NO: 110) | ARRTETMITTVLYYYAMDY (SEQ ID NO: 132) |
| A-11 Nucleic Acid | ggattttcactgagcacttctggtttgggtgtaggc (SEQ ID NO: 87) | cacatttggtgggatgatgataagtactataatccatcccttaagaga (SEQ ID NO: 111) | gctcgaaggaggggaagttaacttcggtattaactattactattctatggactac (SEQ ID NO: 133) |

TABLE 2-continued

| heavy chain CDR amino acid sequences and polynucleotide coding sequences | | | |
| --- | --- | --- | --- |
| | CDR1 | CDR2 | CDR3 |
| A-11<br>Amino Acid | GFSLSTSGLGVG<br>(SEQ ID NO: 88) | HIWWDDDKYYNPSLKR<br>(SEQ ID NO: 112) | ARRREVNFGINYYYSMDY<br>(SEQ ID NO: 134) |
| A-12<br>Nucleic Acid | ggattcaccttcagtgatt<br>attac<br>(SEQ ID NO: 89) | attagaaatcgggctaatggttacac<br>aaca<br>(SEQ ID NO: 113) | gtaagagattcctatcacta<br>cgggtacttcgatgtc<br>(SEQ ID NO: 135) |
| A-12<br>Amino Acid | GFTFSDYY<br>(SEQ ID NO: 90) | IRNRANGYTT<br>(SEQ ID NO: 114) | VRDSYHYGYFDV<br>(SEQ ID NO: 136) |

15

In one embodiment, the antibody provided herein comprises a sequence that differs from a CDR sequence listed in Table 1 and Table 2 by 5, 4, 3, 2 or 1 amino acid addition(s), substitution(s), and/or deletion(s). In another embodiment, the antibody provided herein comprises a sequence that differs from a CDR sequence listed in Table 1 and Table 2 by 4, 3, 2 or 1 amino acid addition(s), substitution(s), and/or deletion(s). In yet another embodiment, the antibody provided herein comprises a sequence that differs from a CDR sequence listed in Table 1 and Table 2 by 3, 2 or 1 amino acid addition(s), substitution(s), and/or deletion(s). In yet another embodiment, the antibody provided herein comprises a sequence that differs from a CDR sequence listed in Table 1 and Table 2 by 2 or 1 amino acid addition(s), substitution(s), and/or deletion(s). In still another embodiment, the antibody provided herein comprises a sequence that differs from a CDR sequence listed in Table 1 and Table 2 by 1 amino acid addition, substitution, and/or deletion.

In another embodiment, the $ET_AR$ antibody provided herein ($ET_AR$-1 antibody) comprises 1 or 2 amino acid sequences, wherein each amino acid sequence is independently selected from the amino acid sequences listed below:

a. light chain CDR1 amino acid sequences: SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30; and b. heavy chain CDR1 amino acid sequences: SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, and SEQ ID NO: 90.

In one aspect, the $ET_AR$-1 antibody further comprises 1 or 2 amino acid sequences, wherein each amino acid sequence is independently selected from the amino acid sequences listed below:

a. light chain CDR2 amino acid sequences: SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, and SEQ ID NO: 48; and b. heavy chain CDR2 amino acid sequences: SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, and SEQ ID NO: 114.

In another aspect, the $ET_AR$-1 antibody further comprises 1 or 2 amino acid sequences, wherein each amino acid sequence is independently selected from the amino acid sequences listed below:

a. light chain CDR3 amino acid sequences: SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, and SEQ ID NO: 68; and b. heavy chain CDR3 amino acid sequences: SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, and SEQ ID NO: 136.

In yet another embodiment, the $ET_AR$ antibody provided herein ($ET_AR$-2 antibody) comprises 1 or 2 amino acid sequences, wherein each amino acid sequence is independently selected from the amino acid sequences listed below:

a. light chain CDR2 amino acid sequences: SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, and SEQ ID NO: 48; and b. heavy chain CDR2 amino acid sequences: SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, and SEQ ID NO: 114.

In one aspect, the $ET_AR$-2 antibody further comprises 1 or 2 amino acid sequences, wherein each amino acid sequence is independently selected from the amino acid sequences listed below:

a light chain CDR1 amino acid sequences: SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30; and b. heavy chain CDR1 amino acid sequences: SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, and SEQ ID NO: 90.

In another aspect, the $ET_AR$-2 antibody further comprises 1 or 2 amino acid sequences, wherein each amino acid sequence is independently selected from the amino acid sequences listed below:

a. light chain CDR3 amino acid sequences: SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, and SEQ ID NO: 68; and b. heavy chain CDR3 amino acid sequences: SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, and SEQ ID NO: 136.

In yet another embodiment, the $ET_AR$ antibody provided herein ($ET_AR$-3 antibody) comprises 1 or 2 amino acid sequences, wherein each amino acid sequence is independently selected from the amino acid sequences listed below:

a. light chain CDR3 amino acid sequences: SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, and SEQ ID NO: 68; and b. heavy chain CDR3 amino acid sequences: SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, and SEQ ID NO: 136.

In one aspect, the $ET_AR$-3 antibody further comprises 1 or 2 amino acid sequences, wherein each amino acid sequence is independently selected from the amino acid sequences listed below:

a light chain CDR1 amino acid sequences: SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30; and b. heavy chain CDR1 amino acid sequences: SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, and SEQ ID NO: 90.

In another aspect, the $ET_AR$-3 antibody further comprises 1 or 2 amino acid sequences, wherein each amino acid sequence is independently selected from the amino acid sequences listed below:

a. light chain CDR2 amino acid sequences: SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, and SEQ ID NO: 48; and b. heavy chain CDR2 amino acid sequences: SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, and SEQ ID NO: 114.

In one embodiment, the $ET_AR$ antibody provided herein comprises:

a. a light chain CDR1 amino acid sequence independently selected from the list below: SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30;

b. a light chain CDR2 amino acid sequence independently selected from the list below: SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, and SEQ ID NO: 48;

c. a light chain CDR3 amino acid sequence independently selected from the list below: SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, and SEQ ID NO: 68;

d. a heavy chain CDR1 amino acid sequence independently selected from the list below: SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, and SEQ ID NO: 90;

e. a heavy chain CDR2 amino acid sequence independently selected from the list below: SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, and SEQ ID NO: 114; and f. a heavy chain CDR3 amino acid sequence independently selected from the list below: SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, and SEQ ID NO: 136.

In one embodiment, the $ET_AR$ antibody provided herein comprises a light chain CDR3 amino acid sequence independently selected from the list below: SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, and SEQ ID NO: 68. In another embodiment, the $ET_AR$ antibody provided herein comprises a heavy chain CDR3 amino acid sequence independently selected from the list below: SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, and SEQ ID NO: 136. In yet another embodiment, the $ET_AR$ antibody comprises a combination of light and heavy chain CDR3 amino acid sequences independently selected from the list below: SEQ ID NO: 50 versus SEQ ID NO: 116, SEQ ID NO: 62 versus SEQ ID NO: 128, SEQ ID NO: 62 versus SEQ ID NO: 130, SEQ ID NO: 64 versus SEQ ID NO: 132, SEQ ID NO: 66 versus SEQ ID NO: 134, and SEQ ID NO: 68 versus SEQ ID NO: 136.

In another embodiment, the $ET_AR$ antibody comprises 1 or 2 amino acid sequences, wherein each amino acid sequence is independently selected from the amino acid sequences listed below:

a. amino acid sequences of light chain variable domains: SEQ ID NO: 138 (L1), SEQ ID NO: 140 (L2), SEQ ID NO: 142 (L3), SEQ ID NO: 144 (L4), SEQ ID NO: 146 (L5), SEQ ID NO: 148 (L6), SEQ ID NO: 150 (L7), SEQ ID NO: 152 (L8), SEQ ID NO: 154 (L9), SEQ ID NO: 156 (L10), SEQ ID NO: 158 (L11), SEQ ID NO: 160 (L12), SEQ ID NO: 162 (L13), SEQ ID NO: 164 (L14) and amino acid sequences at least 80%, 85%, 90% or 95% identical to one of the amino acid sequences listed above; and b. amino acid sequences of heavy chain variable domains: SEQ ID NO: 166 (H1), SEQ ID NO: 168 (H2), SEQ ID NO: 170 (H3), SEQ ID NO: 172 (H4), SEQ ID NO: 174 (H5), SEQ ID NO: 176 (H6), SEQ ID NO: 178 (H7), SEQ ID NO: 180 (H8), SEQ ID NO: 182 (H9), SEQ ID NO: 184 (H10), SEQ ID NO: 186 (H11), SEQ ID NO: 188 (H12), SEQ ID NO: 190 (H13), and SEQ ID NO: 192 (H14), and amino acid sequences at least 80%, 85%, 90% or 95% identical to one of the amino acid sequences listed above.

In yet another embodiment, a polynucleotide coding sequence of the $ET_AR$ antibody provided herein comprises 1 or 2 polynucleotide sequences, wherein each polynucleotide sequence is independently selected from the polynucleotide sequences listed below:

a. polynucleotide coding sequences of light chain variable domains: SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, and polynucleotide sequences at least 80%, 85%, 90% or 95% identical to one of the polynucleotide sequences listed above, and b. polynucleotide coding sequences of heavy chain variable domains: SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 187, SEQ ID NO: 189, SEQ ID NO: 191, and polynucleotide sequences at least 80%, 85%, 90% or 95% identical to one of the polynucleotide sequences listed above.

In yet another embodiment, the ET$_A$R antibody provided herein comprises:

a. an amino acid sequence of light chain variable domain independently selected from the list below: SEQ ID NO: 138 (L1), SEQ ID NO: 140 (L2), SEQ ID NO: 142 (L3), SEQ ID NO: 144 (L4), SEQ ID NO: 146 (L5), SEQ ID NO: 148 (L6), SEQ ID NO: 150 (L7), SEQ ID NO: 152 (L8), SEQ ID NO: 154 (L9), SEQ ID NO: 156 (L10), SEQ ID NO: 158 (L11), SEQ ID NO: 160 (L12), SEQ ID NO: 162 (L13), SEQ ID NO: 164 (L14), and amino acid sequences at least 80%, 85%, 90% or 95% identical to one of the amino acid sequences listed above, and b. an amino acid sequence of heavy chain variable domain independently selected from the list below: SEQ ID NO: 166 (H1), SEQ ID NO: 168 (H2), SEQ ID NO: 170 (H3), SEQ ID NO: 172 (H4), SEQ ID NO: 174 (H5), SEQ ID NO: 176 (H6), SEQ ID NO: 178 (H7), SEQ ID NO: 180 (H8), SEQ ID NO: 182 (H9), SEQ ID NO: 184 (H10), SEQ ID NO: 186 (H11), SEQ ID NO: 188 (H12), SEQ ID NO: 190 (H13), SEQ ID NO: 192 (H14), and amino acid sequences at least 80%, 85%, 90% or 95% identical to one of the amino acid sequences listed above.

In yet another embodiment, the ET$_A$R antibody provided herein comprises:

a. an amino acid sequence of light chain variable domain independently selected from the list below: SEQ ID NO: 138 (L1), SEQ ID NO: 140 (L2), SEQ ID NO: 142 (L3), SEQ ID NO: 144 (L4), SEQ ID NO: 146 (L5), SEQ ID NO: 148 (L6), SEQ ID NO: 150 (L7), SEQ ID NO: 152 (L8), SEQ ID NO: 154 (L9), SEQ ID NO: 156 (L10), SEQ ID NO: 158 (L11), SEQ ID NO: 160 (L12), SEQ ID NO: 162 (L13), and SEQ ID NO: 164 (L14), and b. an amino acid sequence of heavy chain variable domain independently selected from the list below: SEQ ID NO: 166 (H1), SEQ ID NO: 168 (H2), SEQ ID NO: 170 (H3), SEQ ID NO: 172 (H4), SEQ ID NO: 174 (H5), SEQ ID NO: 176 (H6), SEQ ID NO: 178 (H7), SEQ ID NO: 180 (H8), SEQ ID NO: 182 (H9), SEQ ID NO: 184 (H10), SEQ ID NO: 186 (H11), SEQ ID NO: 188 (H12), SEQ ID NO: 190 (H13), and SEQ ID NO: 192 (H14).

In yet another embodiment, the ET$_A$R antibody provided herein comprises a combination of amino acid sequences of light and heavy chain variable domains independently selected from the list below: SEQ ID NO: 138 and SEQ ID NO: 166 (L1H1), SEQ ID NO: 140 and SEQ ID NO: 168 (L2H2), SEQ ID NO: 142 and SEQ ID NO: 170 (L3H3), SEQ ID NO: 144 and SEQ ID NO: 172 (L4H4), SEQ ID NO: 146 and SEQ ID NO: 174 (L5H5), SEQ ID NO: 148 and SEQ ID NO: 176 (L6H6), SEQ ID NO: 150 and SEQ ID NO: 178 (L7H7), SEQ ID NO: 152 and SEQ ID NO: 180 (L8H8), SEQ ID NO: 154 and SEQ ID NO: 182 (L9H9), SEQ ID NO: 156 and SEQ ID NO: 184 (L10H10), SEQ ID NO: 158 and SEQ ID NO: 186 (L11H11), SEQ ID NO: 160 and SEQ ID NO: 188 (L12H12), SEQ ID NO: 162 and SEQ ID NO: 190 (L13H13), and SEQ ID NO: 164 and SEQ ID NO: 192 (L14H14).

ET$_A$R antibody provided herein can also be designated using the nomenclature "LxHy", wherein "x" corresponds to the sequence number of the light chain variable region and "y" corresponds to the sequence number of the heavy chain variable region. For example, L2H1 refers to an antibody with a light chain variable region comprising the amino acid sequence of SEQ ID NO: 140 (L2) and a heavy chain variable region comprising the amino acid sequence of SEQ ID NO: 166 (H1).

In yet another embodiment, the ET$_A$R antibody provided herein comprises a light chain variable domain selected from L1-L14 or a heavy chain variable domain selected from H1-H14, and fragments, derivatives, muteins, or variants thereof.

In yet another embodiment, the ET$_A$R antibody provided herein comprises a combination of light and heavy chain CDR3 amino acid sequences independently selected from the list below: SEQ ID NO: 138 and SEQ ID NO: 166, SEQ ID NO: 150 and SEQ ID NO: 178, SEQ ID NO: 152 and SEQ ID NO: 180, SEQ ID NO: 154 and SEQ ID NO: 182, SEQ ID NO: 156 and SEQ ID NO: 184, SEQ ID NO: 158 and SEQ ID NO: 186, SEQ ID NO: 160 and SEQ ID NO: 188, SEQ ID NO: 162 and SEQ ID NO: 190, and SEQ ID NO: 164 and SEQ ID NO: 192.

In one embodiment, the ET$_A$R antibody provided herein comprises light chain variable domain amino acid sequence SEQ ID NO: 138 or heavy chain variable domain amino acid sequence SEQ ID NO: 166. In another embodiment, the ET$_A$R antibody provided herein comprises the combination of light chain variable domain amino acid sequence SEQ ID NO: 138 and heavy chain variable domain amino acid sequence SEQ ID NO: 166.

In another embodiment, the ET$_A$R antibody provided herein further comprises an amino acid sequence of a constant domain, wherein the amino acid sequence of the constant domain is independently selected from the amino acid sequences listed below:

a. light chain constant domain amino acid sequences: SEQ ID NO: 194 and SEQ ID NO: 196; and b. heavy chain constant domain amino acid sequence: SEQ ID NO: 198.

In yet another embodiment, the ET$_A$R antibody provided herein further comprises constant domain amino acid sequences, wherein each constant domain amino acid sequence is independently selected from the combinations of the light chain and heavy chain constant domain amino acid sequences listed below:

a. a combination of light chain constant domain amino acid sequence SEQ ID NO:194 and heavy chain constant domain amino acid sequence SEQ ID NO: 198; and b. a combination of light chain constant domain amino acid sequence SEQ ID NO:196 and heavy chain constant domain amino acid sequence SEQ ID NO: 198.

In one embodiment, the antibody provided herein comprises the amino acid sequences of the light and heavy chain CDRs and FRs (framework) illustrated above. In one embodiment, the antibody comprises a light chain CDR1 sequence illustrated above. In another embodiment, the antibody comprises a light chain CDR2 sequence illustrated above. In another embodiment, the antibody comprises a light chain CDR3 sequence illustrated above. In another embodiment, the antibody comprises a heavy chain CDR1 sequence illustrated above. In another embodiment, the antibody comprises a heavy chain CDR2 sequence illustrated above. In another embodiment, the antibody comprises a heavy chain CDR3 sequence illustrated above. In another embodiment, the antibody comprises a light chain FR1 sequence illustrated above. In another embodiment, the antibody comprises a light chain FR2 sequence illustrated above. In another embodiment, the antibody comprises a light chain FR3 sequence illustrated above. In another embodiment, the antibody comprises a light chain FR4 sequence illustrated above. In another embodiment, the antibody comprises a heavy chain FR1 sequence illustrated above. In another embodiment, the antibody comprises a heavy chain FR2 sequence illustrated above. In another embodiment, the antibody comprises a heavy chain FR3 sequence illustrated above. In another embodiment, the antibody comprises a heavy chain FR4 sequence illustrated above.

In one embodiment, a CDR3 sequence of the antibody differs from the combination of SEQ ID NO: 50 and SEQ ID NO: 116 of the light chain and heavy chain CDR3 sequences illustrated above by no more than 6, 5, 4, 3, 2 or 1 amino acid addition(s), substitution(s), and/or deletion(s). In another embodiment, a light chain CDR3 sequence of the antibody differs from SEQ ID NO: 50 of the light chain CDR3 sequence illustrated above by no more than 6, 5, 4, 3, 2 or 1 amino acid addition(s), substitution(s), and/or deletion(s). In another embodiment, a light chain CDR3 sequence of the antibody differs from SEQ ID NO: 50 of the light chain CDR3 sequence illustrated above by no more than 6, 5, 4, 3, 2 or 1 amino acid addition(s), substitution(s), and/or deletion(s) and a heavy chain CDR3 sequence of the antibody differs from SEQ ID NO: 116 or SEQ ID NO: 118 of the heavy chain CDR3 sequence illustrated above by no more than 6, 5, 4, 3, 2 or 1 amino acid addition(s), substitution(s), and/or deletion(s). In another embodiment, the antibody further comprises a combination of 1, 2, 3, 4, 5 or 6 of light and heavy chain CDR sequences illustrated above. In another embodiment, the antibody further comprises a combination of 1, 2, 3, 4, 5 or 6 of light and heavy chain CDR sequences illustrated above, wherein each sequence independently differs from a combination of SEQ ID NO: 50 and SEQ ID NO: 116 of light chain and heavy chain CDR3 sequences by 6, 5, 4, 3, 2 or 1 amino acid addition(s), substitution(s), and/or deletion(s). In another embodiment, the antibody comprises the CDRs of a light chain variable region and the CDRs of a heavy chain variable region illustrated above. In another embodiment, the antibody comprises a combination of 1, 2, 3, 4, 5, and/or 6 of light and heavy chain CDR sequences illustrated above.

In one embodiment, the antibody (such as an antibody or antibody fragment) comprises the amino acid sequence of light chain variable domain L1 illustrated above. In one embodiment, the sequence of the light chain variable domain differs from the sequence of light chain variable domain L1 by 15, 14, 13, 12, 11, 10, 9, 8, 7, 6, 5, 4, 3, 2 or 1 amino acid deletion(s), insertion(s), or substitution(s). In another embodiment, the light-chain variable domain comprises an amino acid sequence at least 70%, at least 75%, at least 80%, at least 85%, at least 90%, at least 95%, at least 97% or at least 99% identical to the sequence of light chain variable domain L1. In another embodiment, the polynucleotide coding sequence of the light chain variable domain comprises a nucleotide coding sequence at least 70%, at least 75%, at least 80%, at least 85%, at least 90%, at least 95%, at least 97% or at least 99% identical to the polynucleotide coding sequence of L1. In another embodiment, the polynucleotide coding sequence of the light chain variable domain comprises a polynucleotide that hybridizes under moderately stringent conditions to the complement of the polynucleotide coding sequence of light chain variable domain L1. In another embodiment, the polynucleotide coding sequence of the light chain variable domain comprises a polynucleotide that hybridizes under stringent conditions to the complement of the polynucleotide coding sequence of light chain variable domain L1.

In one embodiment, the antibody (such as an antibody or antibody fragment) comprises the amino acid sequence of heavy chain variable domain H1 illustrated above. In one embodiment, the sequence of the heavy chain variable domain differs from the sequence of heavy chain variable domain H1 by 15, 14, 13, 12, 11, 10, 9, 8, 7, 6, 5, 4, 3, 2 or 1 amino acid deletion(s), insertion(s), or substitution(s). In another embodiment, the heavy chain variable domain comprises an amino acid sequence at least 70%, at least 75%, at least 80%, at least 85%, at least 90%, at least 95%, at least 97% or at least 99% identical to the sequence of heavy chain variable domain H1. In another embodiment, a polynucleotide coding sequence of the heavy chain variable domain comprises a polynucleotide sequence at least 70%, at least 75%, at least 80%, at least 85%, at least 90%, at least 95%, at least 97% or at least 99% identical to the polynucleotide sequence of H1. In another embodiment, the polynucleotide coding sequence of the heavy chain variable domain comprises a polynucleotide that hybridizes under moderately stringent conditions to the complement of a polynucleotide coding sequence of the heavy chain variable domain H1. In another embodiment, the polynucleotide coding sequence of the heavy chain variable domain comprises a polynucleotide that hybridizes under stringent conditions to the complement of a polynucleotide coding sequence of the heavy chain variable domain H1.

In one embodiment, the antibody provided herein include the combination of L1H1, L2H2, L3H3, L4H4, L5H5, L6H6, L7H7, L8H8, L9H9, L10H10, L11H11, L12H12, L13H13 or L14H14; or an isotype thereof (for example, IgA, IgG1, IgG2a, IgG2b, IgG3, IgM, IgE, or IgD) or a Fab or F(ab')2 fragment thereof.

In one embodiment, the antibody provided herein includes an antibody comprising a combination of L1H1, or a converted isotype antibody thereof (for example, IgA, IgG1, IgG2a, IgG2b, IgG3, IgM, IgE, or IgD) or a Fab or F(ab')2 fragment thereof.

The antibody (e.g., an antibody, antibody fragment, and antibody derivative) provided herein can comprise any constant region known in the art. The light chain constant region can be, for example, a kappa- or lambda-type light chain constant region, e.g., a murine kappa- or lambda-type light chain constant region. The heavy chain constant region can be, for example, an alpha-, delta-, epsilon- gamma-, or mu-type heavy chain constant regions, e.g., a murine alpha-, delta-, epsilon-, gamma-, or mu-type heavy chain constant region. In one embodiment, the light or heavy chain constant region is a fragment, derivative, variant, or mutein of a naturally occurring constant region.

In one embodiment, the antibody provided herein further comprises a constant light chain κ or λ region or a fragment thereof. The light chain constant region sequence and its polynucleotide coding sequence are provided as follows:
Light Chain Constant Region:
  polynucleotide (κ), (SEQ ID NO: 193); amino acid (κ), (SEQ ID NO: 194)
  polynucleotide (λ), (SEQ ID NO: 195); amino acid (λ), (SEQ ID NO: 196)

In another embodiment, the antibody provided herein further comprises a heavy chain constant region or a fragment thereof. The heavy chain constant region sequence and its polynucleotide coding sequence are provided as follows:

polynucleotide (IgG1), (SEQ ID NO: 197); amino acid (IgG1), (SEQ ID NO: 198)

In one embodiment, the $ET_AR$ antibody provided herein is selected from murine antibodies, humanized antibodies, chimeric antibodies, monoclonal antibodies, polyclonal antibodies, recombinant antibodies, antigen-binding antibody fragments, single-chain antibodies, double-chain antibodies, triple-chain antibodies, tetra-chain antibodies, Fab fragments, F(ab')x fragments, domain antibodies, IgD antibodies, IgE antibodies, IgM antibodies, IgG1 antibodies, IgG2 antibodies, IgG3 antibodies, and IgG4 antibodies. In another embodiment, the $ET_AR$ antibody provided herein is an $ET_AR$ monoclonal antibody. In yet another embodiment, the $ET_AR$ antibody provided herein is a mouse $ET_AR$ antibody. The $ET_AR$ antibody provided herein is a humanized $ET_AR$ antibody.

In one embodiment, the $ET_AR$ antibody provided herein is monoclonal antibody A-1 (comprising SEQ ID NO: 138 and SEQ ID NO: 166), A-7 (comprising SEQ ID NO: 150 and SEQ ID NO: 178), A-8 (comprising SEQ ID NO: 152 and SEQ ID NO: 180), A-9 (comprising SEQ ID NO: 154 and SEQ ID NO: 182), A-10 (comprising SEQ ID NO: 156 and SEQ ID NO: 184), A-11 (comprising SEQ ID NO: 158 and SEQ ID NO: 186), A-12 (comprising SEQ ID NO: 160 and SEQ ID NO: 188), A-13 (comprising SEQ ID NO: 162 and SEQ ID NO: 190), or A-14 (comprising SEQ ID NO: 164 and SEQ ID NO: 192).

Antibodies and Antibody Fragments

In one embodiment, the antibody provided herein is a full-length antibody (including polyclonal, monoclonal, chimeric, humanized or human antibody with full length heavy and/or light chains). In another embodiment, the antibody provided herein is an antibody fragment, for example, F(ab')2, Fab, Fab', Fv, Fc, or Fd fragment, and can be incorporated into single domain antibodies, single-chain antibodies, maxibodies, minibodies, intrabodies, double-chain antibodies, triple-chain antibodies, tetra-chain antibodies, v-NAR and bis-scFv (see e.g., Hollinger and Hudson, 2005, *Nature Biotechnology*, 23, 9, 1126-1136). In another embodiment, the antibody provided herein also includes antibody polypeptides such as those disclosed in U.S. Pat. No. 6,703,199, including fibronectin polypeptide monobodies. In another embodiment, the antibody provided herein also includes other antibody polypeptides disclosed in U.S. Patent Publication 2005/0238646, which are single-chain polypeptides.

In one embodiment, the variable regions of a gene expressing a monoclonal antibody of interest are amplified using nucleotide primers in a hybridoma. These primers can be synthesized by one of ordinary skill in the art, or can be purchased from commercially available sources (see, e.g., Stratagene, La Jolla, Calif), which sells primers for mouse and human variable regions including, among others, primers for $V_{Ha}$, $V_{Hb}$, $V_{Hc}$, $V_{Hd}$, $C_{H1}$, $V_L$ and $C_L$ regions. These primers can be used to amplify heavy or light chain variable regions, which can then be inserted into vectors such as IMMUNOZAP™H or IMMUNOZAP™L (Stratagene), respectively. These vectors can then be introduced into *E. coli*, yeast, or mammalian-based systems for expression. Large amounts of a single-chain protein containing a fusion of the $V_H$ and $V_L$ regions can be produced using these methods (see Bird el al., 1988, *Science* 242:423-426).

Once antibody-producing cells of the instant invention have been obtained using any above-described immunization and other techniques, the genes of the specific antibodies can be cloned by isolating and amplifying DNA or mRNA therefrom according to standard procedures described herein. The antibodies produced therefrom can be sequenced to identify CDRs, and the coding DNA of the CDRs can be manipulated as described above to generate other antibodies provided herein.

Antibodies provided herein preferably modulate endothelin signaling in the cell-based assay described herein and/or in the in vivo assay described herein and/or cross-block the binding of one of the antibodies described herein and/or are cross-blocked from binding $ET_AR$ by one of the antibodies described herein. Accordingly, such binding agents can be identified using the assays described herein.

In certain embodiments, antibodies are generated by first identifying antibodies that bind to cells overexpressing $ET_AR$ and/or neutralize in the cell-based and/or in vivo assays described herein and/or cross-block the antibodies described herein and/or are cross-blocked from binding $ET_AR$ by one of the antibodies described herein.

It should be understood by one skilled in the art that certain proteins, such as antibodies, can undergo a variety of post-translational modifications. The types and extents of these modifications often depend on the host cell lines used to express the protein as well as the culture conditions. Such modifications can include variations in glycosylation, methionine oxidation, diketopiperizine formation, aspartate isomerization and asparagine deamidation. A frequent modification is the loss of a carboxyl-terminal basic residue (such as lysine or arginine) due to the action of carboxypeptidases (as described in Harris, R. J., 1995, *Journal of Chromatography* 705:129-134).

An alternative method for production of a murine monoclonal antibody is to inject hybridoma cells into the peritoneal cavity of a syngeneic mouse, for example, a mouse that has been treated (e.g., pristine-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, e.g., Coligan at pages 2.7.1-2.7.12 and pages 2.9.1-2.9.3; Baines et al., "Purification of Immunoglobulin G (IgG)," in Methods in Molecular Biology, Vol. 10, pages 79-104 (The Humana Press, Inc. 1992)). A monoclonal antibody can be purified by affinity chromatography using an appropriate ligand selected based on particular properties of the antibody (e.g., heavy or light chain isotype, binding specificity, etc.). Examples of suitable ligands immobilized on a solid support include Protein A, Protein G, an anti-constant region (light chain or heavy chain) antibody, an anti-idiotype antibody, and a TGF-β binding protein, or a fragment or variant thereof.

Molecular evolution of the complementarity determining regions (CDRs) in the center of the antibody binding site also has been used to isolate antibodies with increased affinities, for example, antibodies having increased affinities for c-erbB-2, as described by Schier et al., 1996, *J. Mol. Biol.* 263:551-567. Accordingly, such techniques are useful in preparing antibodies of human endothelin A receptor.

Antibodies against human endothelin A receptor can be used, for example, in assays to detect the presence of the endothelin A receptor, either in vitro or in vivo.

Antibodies can also be prepared by any of the conventional techniques. For example, they can be purified from cells that naturally express them (e.g., an antibody can be purified from a hybridoma that produces it) or produced in recombinant expression systems using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988). This is discussed in the nucleic acid section below.

Antibodies can be prepared and screened for desired properties by any known techniques. Some techniques relate to the isolation of nucleic acids encoding polypeptide chains (or portions thereof) of related antibodies (e.g., anti-ET$_A$R antibodies) and manipulation of nucleic acid. Nucleic acids can be fused with another relevant nucleic acid or modified by recombinant DNA techniques (e.g., induced mutations or other conventional techniques) to add, delete or replace one or more amino acid residues.

Where it is desired to improve the affinity of antibodies according to the invention containing one or more of the above-mentioned CDRs, such antibodies can be obtained by a number of affinity maturation protocols, including maintaining the CDRs (Yang et al., 1995, *J. Mol. Biol.*, 254:392-403), chain shuffling (Marks et al., 1992, *Bio/Technology*, 10:779-783), use of mutation strains of *E. coli.* (Low et al., 1996, *J. Mol. Biol.*, 250:350-368), DNA shuffling (Patten et al., 1997, *Curr. Opin. Biotechnol.*, 8:724-733), phage display (Thompson et al., 1996, *J. Mol. Biol.*, 256:7-88) and additional PCR techniques (Crameri et al., 1998, *Nature*, 391:288-291). All of these methods or affinity maturation are discussed in Vaughan et al., 1998, *Nature Biotechnology*, 16:535-539).

In one embodiment, fragments of the ET$_A$R antibody are provided herein. Such fragments can comprise entirely antibody-derived sequences or additional sequences. Examples of antigen binding fragments include Fab, F(ab')2, single chain antibodies, diabodies, tribodies, tetrabodies, and domain antibodies. Other examples are provided in Lunde et al., 2002, *Biochem. Soc. Trans.* 30:500-06.

Single chain antibodies can be formed by linking heavy and light chain variable domain (Fv region) fragments via an amino acid bridge (short peptide linker), resulting in a single polypeptide chain. Such single-chain Fvs (scFvs) have been prepared by fusion DNA encoding a peptide linker between DNAs encoding the two variable domain polypeptides (V$_L$ and V$_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different V$_L$ and V$_H$-comprising polypeptides, multimeric scFvs that bind to different epitopes can be formed (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544; de Graaf et al., 2002, *Methods Mol. Biol.* 178:379-87. Single chain antibodies derived from antibodies provided herein including, but not limited to, scFvs comprising the variable domain combination L1H1, are encompassed by the present invention.

Antibodies derived from an antibody can also be obtained, for example, by proteolytic hydrolysis of the antibody, for example, pepsin or papain digestion of a whole antibody according to conventional methods. By way of example, antibody fragments can be produced by enzymatic cleavage of antibodies with pepsin to provide a SS fragment termed F(ab')2. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoffet et al., 1960, *Arch. Biochem. Biophys.* 89:230; Porter, 1959, *Biochem. J.* 73:119; Edelman et al., Methods in Enzymology 1:422 (Academic Press 1967); and by Andrews, S. M. and Titus, J. A. in Current Protocols in Immunology (Coligan J. E., et al., eds), John Wiley & Sons, New York (2003), pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques can also be used, so long as the fragments bind to the antigen that is recognized by the intact antibody.

Another form of an antibody fragment is a peptide comprising one or more complementarity determining regions (CDRs) of an antibody. CDRs can be obtained by constructing polynucleotides that encode the CDRs. Such polynucleotides are prepared, for example, by using the polymerase chain reaction to synthesize the variable region using mRNA or antibody-producing cells as a template (see, for example, Larrick et al., 1991, Methods: A Companion to Methods in Enzymology 2:106; Courtenay-Luck, "(Genetic Manipulation of Monoclonal Antibodies," in Monoclonal Antibodies: Production, Engineering and Clinical Application, Ritter et al. (eds.), page 166 (Cambridge University Press 1995); and Ward el al., "Genetic Manipulation and Expression or Antibodies," in Monoclonal Antibodies: Principles and Applications, Birch et al., (eds.), page 137 (Wiley-Liss, Inc. 1995). The antibody fragment further can comprise at least one variable region domain of an antibody described herein. Thus, for example, the V region domain can be monomeric and be a V$_H$ or V$_L$ domain, which can bind to ET$_A$R with an affinity of $1 \times 10^{-7}$ M or less as described below.

The variable region domain can be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain can be covalently attached at a C-terminal amino acid to at least one other antibody domain or a fragment thereof. Thus, for example, a V$_H$ domain that is present in the variable region domain can be linked to an immunoglobulin C$_{H1}$ domain or a fragment thereof. Similarly, a V$_L$ domain can be linked to a C$_K$ domain or a fragment thereof. In this way, for example, the antibody can be a Fab fragment, wherein the antigen binding domain contains associated V$_H$ and V$_L$ domains covalently linked at their C-termini to a C$_{H1}$ and C$_\kappa$ domain, respectively. The C$_{H1}$ domain can be extended with further amino acids, for example to provide a hinge region or a portion of a hinge region domain as found in a Fab' fragment, or to provide further domains, such as antibody $C_{H2}$ and $C_{H3}$ domains.

Derivatives and Variants of Antibodies

The nucleotide sequences of L1 and H1, encoding the corresponding amino acid sequences of A-1, can be altered, for example, by random mutagenesis or by site-directed mutagenesis (e.g., oligonucleotide-directed site-specific mutagenesis) to create an altered polynucleotide comprising one or more particular nucleotide substitutions, deletions, or insertions as compared to the non-mutated polynucleotide. Examples of techniques for making such alterations are described in Walder et al., 1986, *Gene* 42:133; Bauer et al., 1985, *Gene* 37:73; Craik, 1985, *BioTechniques*, 3:12-19; Smith et al., 1981, Genetic Engineering: Principles and Methods, Plenum Press; and U.S. Pat. Nos. 4,518,584 and 4,737,462. These and other methods can be used to make, for example, derivatives of anti-endothelin A receptor antibodies that have a desired property, for example, an increase in affinity, avidity, or specificity for an endothelin receptor or in vivo or in vitro stability, or reduced in vivo side-effects as compared to the underivatized antibody.

Other derivatives of anti-endothelin receptor antibodies within the scope or this invention include covalent or aggregative conjugates or anti-endothelin receptor antibodies, or fragments thereof, with other proteins or polypeptides, such as by expression or recombinant fusion proteins comprising heterologous polypeptides fused to the N-terminus or C-terminus or an anti-endothelin receptor antibody polypeptide. For example, the conjugated peptide can be a heterologous signal (or leader) polypeptide, e.g., the yeast alpha-factor leader or a peptide such as an epitope tag. An antibody containing fusion proteins can comprise peptides added to facilitate purification or identification of antigen binding protein (e.g., poly-His). An antibody also can be linked to the FLAG peptide as described in Hopp et al., 1988, *Bio/Technology* 6:1204, and U.S. Pat. No. 5,011,912. The FLAG peptide is highly antigenic and provides an epitope reversibly bound by a specific monoclonal antibody (mAb), enabling rapid assay and facile purification of an expressed recombinant protein. Reagents useful for preparing fusion proteins in which the FLAG peptide is fused to a given polypeptide are commercially available (Sigma, St. Louis, Mo.). In another embodiment, oligomers that contain one or more antibodies can be employed as endothelin receptor antagonists. Oligomers can be in the form of covalently-linked or non-covalently-linked dimers, trimers, or higher oligomers. Oligomers comprising two or more antibodies are contemplated for use, with one example being a homodimer. Other oligomers include heterodimers, homotrimers, heterotrimers, homotetramers, heterotetramers, etc.

One embodiment is directed to oligomers comprising multiple antibodies joined via covalent or non-covalent interactions between peptide moieties fused to the antibodies. Such peptides can be peptide linkers (spacers), or peptides that have the property of promoting oligomerization. Leucine zippers and certain polypeptides derived from antibodies are among the peptides that can promote oligomerization of antibodies attached thereto, as described in more detail below.

In particular embodiments, the oligomers comprise from two to four antibodies. The antibodies of the oligomer can be in any form, such as any of the forms described above, e.g., variants or fragments. Preferably, the oligomers comprise antibodies that have endothelin receptor binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, *PNAS USA* 88:10535; Byrn et al., 1990, *Nature* 344:677; and Hollenbaugh et al., 1992 "Construction of Immunoglobulin Fusion Proteins", in Current Protocols in Immunology, Suppl. 4, pages 10.19.1-10.19.11. One embodiment provided herein is directed to a dimer comprising two fusion proteins created by fusing an endothelin receptor binding fragment of an anti-endothelin A receptor antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon inter-chain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, *EMBO J.* 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. In other embodiments, the variable portion of the heavy and/or light chains of an anti-endothelin receptor antibody can be substituted for the variable portion of an antibody heavy and/or light chain.

Alternatively, the oligomer is a fusion protein comprising multiple antibodies, with or without peptide linkers (spacer peptides). Among the suitable peptide linkers are those described in U.S. Pat. Nos. 4,751,180 and 4,935,233.

Another method for preparing oligomeric antibodies involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, *FEBS Letters* 344:191, hereby incorporated by reference. The use of a modified leucine zipper that allows for stable trimerization of a heterologous protein fused thereto is described in Fanslow et al., 1994, *Semin. Immunol.* 6:267-78. In one method, recombinant fusion proteins comprising an anti-endothelin receptor antibody fragment or derivative fused to a leucine zipper peptide are expressed in suitable host cells, and the soluble oligomeric anti-endothelin receptor antibody fragments or derivatives that form are recovered from the culture supernatant.

In another embodiment, the antibody derivatives can comprise at least one of the CDRs disclosed herein. For example, one or more CDR can be incorporated into known antibody framework regions (IgG1, IgG2, etc.), or conjugated to a suitable vehicle to enhance the half-life thereof. Suitable vehicles include, but are not limited to Fc, albumin, transferrin, and the like. These and other suitable vehicles are known in the art. Such conjugated CDR peptides can be in monomeric, dimeric, tetrameric, or other form. In one embodiment, one or more water-soluble polymer is bonded at one or more specific position, for example at the amino terminus, of a binding agent. In an example, an antibody derivative comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

It will be appreciated that an antibody provided herein can have at least one amino acid substitution, providing that the antibody retains binding specificity. Therefore, modifications to the antibody structures are encompassed within the scope of the invention. These can include amino acid substitutions, which may be conservative or non-conservative, that do not destroy the human endothelin receptor binding capability of an antibody. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution can also involve a substitution of a native amino acid residue with a normative residue such that there is little or no effect on the polarity or charge of the amino acid residue at that position. Non-conservative substitutions can involve the exchange of a member of one class of amino acids or amino acid mimetics for a member from another class with different physical properties (e.g., size, polarity, hydrophobicity, charge).

Moreover, one skilled in the art may generate variants to be tested, which contain a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure. Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. A number of scientific publications have been devoted to the prediction of secondary structure. See Moult, 1996, *Curr. Op. Biotech.* 7:422-427; Chou et al., 1974, *Biochemistry* 13:222-245; Chou et al., 1974, *Biochemistry* 113:211-222; Chou et al., 1978, *Adv. Enzymol. Relat. Areas Mol. Biol.* 47:45-148; Chou et al., 1979, *Ann. Rev. Biochem.* 47:251-276 and Chou et al., *Biophys. J.* 26:367-384. Moreover, computer programs are currently available to assist with predicting secondary structure. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within the structure of a polypeptide or protein. See Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (see Holm, supra (1999), and Brenner, supra (1997)). In certain embodiments, variants of antibodies include glycosylation variants, wherein the number and/or type of glycosylation sites have been altered compared to the amino acid sequences of a parent polypeptide. In certain embodiments, variants comprise a greater or lesser number of N-linked glycosylation sites than the native protein. Alternatively, elimination of such a sequence by substitutions removes an existing N-linked carbohydrate chain. Also provided is a rearrangement of N-linked carbohydrate chains, wherein one or more N-linked glycosylation sites (typically those that are naturally occurring) are eliminated and one or more new N-linked sites are created. Additional preferred antibody variants include cysteine variants, wherein one or more cysteine residues are deleted from or substituted for another amino acid (e.g., serine) as compared to the parent amino acid sequence. Cysteine variants can be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to human endothelin receptor, or to increase or decrease the affinity of the antibodies to human endothelin receptor described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) can be made in the naturally-occurring sequence (in certain embodiments, in the portion of the polypeptide outside the domain(s) forming intermolecular contacts). In certain embodiments, a conservative amino acid substitution typically cannot substantially change the structural characteristics of the parent sequence (e.g., a replacement amino acid should not break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (Branden and Tooze, Eds., Garland Publishing, New York, N.Y. (1991)); and Thornton et al., 1991, Nature 354:105, each of which is incorporated herein by reference.

In certain embodiments, antibodies of the invention can be chemically bonded with polymers, lipids, or other moieties.

The antigen binding agents can comprise at least one of the CDRs described herein incorporated into a biocompatible framework structure. In one embodiment, the biocompatible framework structure comprises a polypeptide or portion thereof that is sufficient to form a conformationally stable structural support, or framework, or scaffold, which is able to present one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically, the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendamistat domains can be used (see, e.g., Nygren and Uhlen, 1997, Current Opinion in Structural Biology 7:463-469).

Additionally, one skilled in the art will recognize that suitable binding agents include portions of these antibodies, such as one or more of heavy chain CDR1, CDR2, CDR3, light chain CDR1, CDR2 and CDR3 as specifically disclosed herein. At least one of the regions of heavy chain CDR1, CDR2, CDR3, CDR1, CDR2 and CDR3 can have at least one amino acid substitution, provided that the antibody retains the binding specificity of the non-substituted CDR. The non-CDR portion of the antibody can be a non-protein molecule, wherein the binding agent cross-blocks the binding of an antibody disclosed herein to human endothelin receptor and/or inhibits the activity of endothelin-1 signaling through the receptor. The non-CDR portion of the antibody can be a non-protein molecule in which the antibody exhibits a similar binding pattern to human endothelin receptor peptides in a competition binding assay as that exhibited by at least one of antibodies A1/A2, and/or neutralizes the activity of endothelin-1. The non-CDR portion of the antibody can be composed of amino acids, wherein the antibody is a recombinant binding protein or a synthetic peptide, and the recombinant binding protein cross-blocks the binding of an antibody disclosed herein to human $ET_AR$ and/or neutralizes endothelin-1 activity in vitro or in vivo. The non-CDR portion of the antibody can be composed of amino acids, wherein the antibody is a recombinant antibody, and the recombinant antibody exhibits a similar binding pattern to human $ET_AR$ peptides in a competition binding assay as exhibited by at least one of the antibodies A1/A2, and/or neutralizes endothelin-1 signaling.

Nucleic Acids

In one aspect, the present invention provides isolated nucleic acid molecules that encode the antibodies provided herein. The nucleic acids comprise, for example, polynucleotides that encode all or part of an antibody, for example, one or both chains of an antibody of the invention, or a fragment, derivative, mutein, or variant thereof; polynucleotides sufficient for use as hybridization probes; PCR primers or sequencing primers for identifying, analyzing, mutating or amplifying a polynucleotide encoding a polypeptide; anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) can be isolated from B-cells of mice that have been immunized with $ET_AR$ antigen. The nucleic acid can be isolated by conventional procedures such as polymerase chain reaction (PCR).

Nucleic acid sequences encoding the variable regions of the heavy and light chain variable regions are shown above. The skilled artisan will appreciate that, due to the degeneracy of the genetic code, each of the polypeptide sequences disclosed herein is encoded by a large number of other nucleic acid sequences. The present invention provides each degenerate nucleotide sequence encoding each antibody of the invention.

The invention further provides nucleic acids that hybridize to other nucleic acids (e.g., nucleic acids comprising a nucleotide sequence of any of A-1/A-2) under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, for example, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., Eds., John Wiley & Sons, Inc., sections 2.10 and 6.3-6.4), and can be readily determined by those having ordinary skill in the art based on, for example, the length and/or base composition of the DNA. Changes can be introduced by mutation into a nucleic acid, thereby leading to changes in the amino acid sequence of a polypeptide (e.g., an antibody) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. No matter how it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. In one embodiment, nucleotide sequences provided herein for L1 to L2 and H1 to H2, or fragments, variants, or derivatives thereof, are mutated such that they encode amino acid sequences provided herein for L1 to L2 and H1 to H2, comprising one or more deletions or substitutions of amino acid residues to result in sequences bearing two or more different amino acid residues. In another embodiment, the mutagenesis inserts an amino acid adjacent to one or more amino acid residues shown herein for L1 to L2 and H1 to H2 to result in sequences with two or more different amino acid residues. Alternatively, one or more mutations can be introduced into a nucleic acid that selectively change the biological activity. (e.g., binding to ET$_A$R) of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., a ET$_A$R binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

In another aspect, the vectors provided herein comprise a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors provided herein can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, the disclosure of each of which is incorporated by reference herein in its entirety), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see Id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell or eukaryotic cell. Prokaryotic host cells include gram negative or gram positive organisms, for example, E. coli or bacilli. Higher eukaryotic cells include insect cells, yeast cells, and established cell lines of mammalian origin. Examples of suitable mammalian host cell lines include Chinese hamster ovary (CHO) cells or their derivatives such as Veggie CHO and related cell lines which grow in serum-free media (see Rasmussen et al., 1998, Cytotechnology 28:31) or CHO strain DXB-11, which is deficient in DHFR (see Urlaub et al., 1980, Proc. Natl. Acad. Sci. USA 77:4216-20). Additional CHO cell lines include CHO-K1 (ATCC #CCL-61), EM9 (ATCC #CRL-1861), and W20 (ATCC #CRL-1862). Additional host cells include the COS-7 line of monkey kidney cells (ATCC #CRL-1651) (see Gluzman et al., 1981, *Cell* 23:175), L cells, C127 cells, 3T3 cells (ATCC CCL-163), AM-1/D cells (described in U.S. Pat. No. 6,210,924), HeLa cells, BHK (ATCC CRL-10) cell lines, the CV1/EBNA cell line derived from the African green monkey kidney cell line CV1 (ATCC CCL-70) (see McMahan et al., 1991, *EMBO J.* 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Appropriate cloning and expression vectors for use with bacterial, fungal, yeast, and mammalian cellular hosts are described by Pouwels et al. (Cloning Vectors: A Laboratory Manual, Elsevier, N.Y., 1985).

Vector DNA can be introduced into prokaryotic or eukaryotic cells via conventional transformation or transfection techniques. For stable transfection of mammalian cells, it is known that, depending upon the expression vector and transfection technique used, only a small fraction of cells can integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

The transformed cells can be cultured under conditions that promote expression of a polypeptide, and the polypeptide recovered by conventional protein purification procedures. One such purification procedure is described in the Examples below. Polypeptides contemplated for use herein include substantially homogeneous recombinant mammalian anti-endothelin receptor antibody polypeptides substantially free of contaminating endogenous materials.

Activity of Antibody

In one embodiment, the antibody provided herein specifically binds to an endothelin receptor, inhibits the signaling transduction, and demonstrates a therapeutic biological effect, for example, the attenuation of pulmonary arterial hypertension in an animal model. In another embodiment, a mouse or humanized antibody provided herein specifically binds to a human endothelin receptor. Such an antibody includes an antagonistic or neutralizing antibody that reduces or neutralizes endothelin signaling.

In one embodiment, the $K_d$ of the antibody provided herein binding to a human endothelin receptor $ET_AR$ is ranging approximately from 0.01 nM to 1000 nM, from 0.1 nM to 500 nM, from 0.5 nM to 200 nM, from 1 nM to 200 nM, or from 10 nM to 100 nM. In another embodiment, the $K_d$ of the antibody provided herein binding to a human endothelin receptor $ET_AR$ is approximately from 1 nM to 200 nM. In yet another embodiment, the $K_d$ of the antibody provided herein binding to a human endothelin receptor $ET_AR$ is approximately from 10 nM to 100 nM. In yet another embodiment, the $K_d$ of the antibody provided herein binding to a human endothelin receptor $ET_AR$ is approximately 1 nM, 2 nM, 5 nM, 10 nM, 20 nM, 30 nM, 40 nM, 50 nM, 60 nM, 70 nM, 80 nM, 90 nM, or 100 nM.

In one embodiment, the $IC_{50}$ of the antibody provided herein antagonizing endothelin signaling is ranging approximately from 0.01 nM to 500 nM, from 0.1 nM to 200 nM, from 0.5 nM to 200 nM, from 1 nM to 200 nM, or from 10 nM to 100 nM. In another embodiment, the $IC_{50}$ of the antibody provided herein antagonizing endothelin signaling is approximately from 1 nM to 200 nM. In yet another embodiment, the $IC_{50}$ of the antibody provided herein antagonizing endothelin signaling is approximately from 10 nM to 100 nM. In yet another embodiment, the $IC_{50}$ of the antibody provided herein antagonizing endothelin signaling is approximately 1 nM, 2 nM, 5 nM, 10 nM, 20 nM, 30 nM, 40 nM, 50 nM, 60 nM, 70 nM, 80 nM, 90 nM, or 100 nM.

In one embodiment, the antibody provided herein specifically binds to a human endothelin receptor $ET_AR$ with one or more following properties:

a. having the same $K_d$ as a reference antibody in binding to a human endothelin receptor $ET_AR$;

b. having the same $IC_{50}$ as a reference antibody in antagonizing a human endothelin receptor $ET_AR$ activated by endothelin; and c. cross-competing binding with a reference antibody to a human endothelin receptor $ET_AR$.

In one aspect, the reference antibody comprises a combination of light chain variable domain amino acid sequence SEQ ID NO: 138 and heavy chain variable domain amino acid sequence SEQ ID NO: 166. In another aspect, the reference antibody is monoclonal antibody A-1, A-2, A-7, A-9, or A-12.

As used herein, the term "substantially similar" means comparable to, or approximately 100%, 99%, 98%, 97%, 95%, 90%, 85%, 80%, 75%, 70%, 65%, or 50% identical to the $IC_{50}$ or $K_b$ (or $K_d$) of a reference antibody. In one embodiment, the reference antibody is, for example, an antibody comprising a heavy chain and light chain combination L1H1 or L2H2. In another embodiment, the reference antibody includes A-1.

In one embodiment, the $ET_AR$ antibody provided herein is able to bind to a human endothelin receptor specifically and lower pulmonary arterial hypertension in an animal model. In one embodiment, the pulmonary arterial hypertension is lowered by about 2% compared with an animal without treatment. In another embodiment, the pulmonary arterial hypertension is lowered by about 5% compared with an animal without treatment. In yet another embodiment, the pulmonary arterial pressure is lowered by about 10% compared to an animal without treatment. In yet another embodiment, the pulmonary arterial hypertension is lowered by about 15% compared to an animal without treatment. In yet another embodiment, the pulmonary arterial hypertension is lowered by about 20% compared to an animal without treatment. In yet another embodiment, the pulmonary arterial hypertension is lowered by about 25% compared to an animal without treatment. The amount of reduction of pulmonary arterial hypertension is controlled by dosage. A therapeutically effective dosage is the dosage required to reduce pulmonary arterial hypertension into the normal range for an animal or human patient.

Pharmaceutical Compositions

In one embodiment, the pharmaceutical composition provided herein comprises an $ET_AR$ antibody provided herein and one or more pharmaceutically acceptable carriers.

In one embodiment, a stable pharmaceutical solution formulation of the $ET_AR$ antibody is provided herein. The stable pharmaceutical solution formulation of the $ET_AR$ antibody is stable and efficacious with a longer half-life in vivo, and can be used to effectively treat pulmonary arterial hypertension and related diseases and cancer of a reproductive organ.

In one embodiment, the stable pharmaceutical solution formulation of the $ET_AR$ antibody provided herein comprises an $ET_AR$ antibody provided herein and a buffer. In one embodiment, the pH of the stable pharmaceutical solution formulation of the $ET_AR$ antibody provided herein is ranging approximately from 4 to 11, from 5 to 7, or from 5 to 6. In another embodiment, the pH of the stable pharmaceutical solution formulation of the $ET_AR$ antibody provided herein is approximately from 5 to 7. In yet another embodiment, the pH of the stable pharmaceutical solution formulation of the $ET_AR$ antibody provided herein is approximately from 5 to 6. In yet another embodiment, the pH of the stable pharmaceutical solution formulation of the $ET_AR$ antibody provided herein is approximately from 5.3 to 6.5. In still another embodiment, the pH of the stable pharmaceutical solution formulation of the $ET_AR$ antibody provided herein is about 5.8.

In one embodiment, in the stable solution formulation of the $ET_AR$ antibody provided herein, the concentration of the $ET_AR$ antibody provided herein is approximately ranging from 10 to 500 mg/mL, from 10 to 250 mg/mL, from 10 to 200 mg/mL, or from 10 to 100 mg/mL. In another embodiment, in the stable solution formulation of the $ET_AR$ antibody provided herein, the concentration of the $ET_AR$ antibody provided herein is approximately 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, or 100 mg/mL. In yet another embodiment, in the stable solution formulation of the $ET_AR$ antibody provided herein, the concentration of the $ET_AR$ antibody provided herein is approximately 110 mg/mL, 120 mg/mL, 130 mg/mL, 140 mg/mL, 150 mg/mL, 160 mg/mL, 170 mg/mL, 180 mg/mL, 190 mg/mL, or 200 mg/mL. In still another embodiment, in the stable solution formulation of the $ET_AR$ antibody provided herein, the concentration of the $ET_AR$ antibody provided herein is approximately 25 mg/mL, 50 mg/mL, 75 mg/mL, or 100 mg/mL.

In one embodiment, in the stable solution formulation of the $ET_AR$ antibody provided herein, the concentration of the buffer described herein is ranging approximately from 1 mM to 200 mM, from 2 mM to 50 mM, or from 5 mM to 25 mM. In yet another embodiment, in the stable solution formulation of the $ET_AR$ antibody provided herein, the concentration of the buffer described herein is approximately 5 mM, 10 mM, 15 mM, 20 mM, 25 mM, 30 mM, 35 mM, 40 mM, 45 mM, or 50 mM. In still another embodiment, in the stable solution formulation of the $ET_AR$ antibody provided herein, the concentration of the buffer described herein is approximately 10 mM, 15 mM, 20 mM, 25 mM, or 30 mM.

In one embodiment, the buffer described herein comprises one or more selected from: citric acid, salts of citric acid, ascorbic acid, salts of ascorbic acid, gluconic acid, salts of gluconic acid, carbonic acid, salts of carbonic acid, tartaric acid, salts of tartaric acid, succinic acid, salts of succinic acid, acetic acid, salts of acetic acid, phthalic acid, salts of phthalic acid, phosphoric acid, salts of phosphoric acid, hydrochloric acid, Tris, thomethamine, and amino acids. In another embodiment, the buffer described herein is a salt of citric acid. In yet another embodiment, the buffer described herein is sodium citrate. In still another embodiment, the buffer described herein is histidine.

In another embodiment, the stable solution formulation of the $ET_AR$ antibody provided herein also comprises a surfactant.

In one embodiment, in the stable solution formulation of the $ET_AR$ antibody provided herein, the concentration of the surfactant described herein is approximately ranging from 0.001 to 1 weight/volume percent, from 0.01 to 0.5 weight/volume percent, or from 0.01 to 0.1 weight/volume percent. In another embodiment, in the stable solution formulation of the $ET_AR$ antibody provided herein, the concentration of the surfactant described herein is approximately from 0.01 to 0.1 weight/volume percent. In yet another embodiment, in the stable solution formulation of the $ET_AR$ antibody provided herein, the concentration of the surfactant described herein is approximately 0.01, 0.02, 0.03, 0.04, 0.05, 0.06, 0.07, 0.08, 0.09, or 0.1 weight/volume percent. In still another embodiment, in the stable solution formulation of the $ET_AR$ antibody provided herein, the concentration of the surfactant described herein is approximately 0.02, 0.03, 0.04, 0.05, or 0.06 weight/volume percent.

In one embodiment, the surfactant described herein is one or more selected from sorbitan fatty acid esters, glycerin fatty acid esters, polyglycerin fatty acid esters, polyoxyethylene sorbitan fatty acid esters, polyoxyethylene sorbitol fatty acid esters, polyoxyethylene glycerine fatty acid esters, polyethylene glycol fatty acid esters, polyoxyethylene alkyl ethers, polyoxyethylene polyoxypropylene alkyl ethers, polyoxyethylene alkylphenyl ethers, polyoxyethylene hydrogenated castor oils, polyoxyethylene beeswax derivatives, polyoxyethylene fatty acid amides, C10-C18 alkyl sulfates, polyoxyethylene C10-C16 alkyl ether sulfate with an average of 2 to 4 moles of the added oxirane groups, C1-C18 alkyl sulfosuccinate ester salts, natural surfactants, sphingophospholipids, and sucrose esters of C12-C18 fatty acids.

In another embodiment, the surfactant described herein is one or more selected from sorbitan fatty acid esters, e.g., sorbitan monocaprylate, sorbitan monolaurate, sorbitan monopalmitate, sorbitan trioleate; glycerin fatty acid esters, e.g., glycerin monocaprylate, glycerin monomyristate, glycerin monostearate; polyglycerin fatty acid esters, e.g., decaglyceryl monostearate, decaglyceryl distearate, decaglyceryl monolinoleate; polyoxyethylene sorbitan fatty acid esters, e.g., polyoxyethylene sorbitan monolaurate, wherein polyoxyethylene (20) sorbitan monolaurate is TWEEN-20 and polyoxyethylene sorbitan monopalmitate is TWEEN-40, polyoxyethylene sorbitan monooleate, wherein polyoxyethylene (80) sorbitan monooleate is TWEEN-80, polyoxyethylene sorbitan monostearate, wherein polyoxyethylene (60) sorbitan monostearate is TWEEN-60, polyoxyethylene sorbitan trioleate is TWEEN-85, and polyoxyethylene sorbitan tristearate is TWEEN-65; polyoxyethylene sorbitol fatty acid esters, e.g., polyoxyethylene sorbitol tetrastearate, polyoxyethylene sorbitol tetraoleate; polyoxyethylene glycerine fatty acid esters, e.g., polyoxyethylene glyceryl monostearate; polyethylene glycol fatty acid esters, e.g., polyethylene glycol distearate; polyoxyethylene alkyl ethers, e.g., polyoxyethylene lauryl ether; polyoxyethylene polyoxypropylene alkyl ethers, e.g., polyoxyethylene polyoxypropylene glycol, polyoxyethylene polyoxypropylene propyl ether, polyoxyethylene polyoxypropylene cetyl ether; polyoxyethylene alkylphenyl ethers, e.g., polyoxyethylene nonylphenyl ether; polyoxyethylene hydrogenated castor oils, e.g., polyoxyethylene castor oil, polyoxyethylene hydrogenated castor oil; polyoxyethylene beeswax derivatives, e.g., polyoxyethylene sorbitol beeswax; polyoxyethylene lanolin derivatives, e.g., polyoxyethylene lanolin; and polyoxyethylene fatty acid amides, e.g., polyoxyethylene stearic acid amide; C10-C18 alkyl sulfates, e.g., sodium cetyl sulfate, sodium lauryl sulfate, sodium oleyl sulfate; polyoxyethylene C10-C16 alkyl ether sulfate with an average of 2 to 4 moles of ethylene oxide units added, e.g., sodium polyoxyethylene lauryl sulfate; and C1-C18 alkyl sulfosuccinate ester salts, e.g., sodium lauryl sulfosuccinate ester; and natural surfactants such as lecithin, glycerophospholipid, sphingophospholipids, e.g., sphingomyelin, and sucrose esters of C12-C18 fatty acids.

In one embodiment, the surfactant described herein is a polyoxyethylene sorbitan fatty acid ester, e.g., TWEEN-20, TWEEN-40, TWEEN-60 and TWEEN-80. In another embodiment, the surfactant described herein is TWEEN-20 or TWEEN-80.

In another embodiment, the stable pharmaceutical solution formulation of the $ET_AR$ antibody also comprises an amino acid protectant.

In one embodiment, in the stable solution formulation of $ET_AR$ antibody provided herein, the concentration of the amino acid protectant described herein is approximately ranging from 1 mM to 500 mM or from 10 mM to 200 mM. In another embodiment, in the stable solution formulation of the $ET_AR$ antibody provided herein, the concentration of the amino acid protectant described herein is approximately from 10 mM to 200 mM. In yet another embodiment, in the stable solution formulation of the $ET_AR$ antibody provided herein, the concentration of the amino acid protectant described herein is approximately 100 mM, 110 mM, 120 mM, 130 mM, 140 mM, 150 mM, 160 mM, 170 mM, 180 mM, 190 mM, or 200 mM. In yet another embodiment, in the stable solution formulation of the $ET_AR$ antibody provided herein, the concentration of the amino acid protectant described herein is approximately 120 mM, 130 mM, 140 mM, 150 mM, or 160 mM.

In one embodiment, the amino acid protectant is one or more selected from histidine, arginine, glycine, and proline. In another embodiment, the amino acid protectant described herein is one or more selected from histidine, arginine, and glycine. In yet another embodiment, the amino acid protectant described herein is arginine or a salt thereof. In still another embodiment, the amino acid protectant described herein is arginine hydrochloride.

In one embodiment, in the stable solution formulation of the $ET_AR$ antibody provided herein, the concentration of the $ET_AR$ antibody is approximately from 10 to 200 mg/mL; the concentration of the surfactant is approximately from 0.01 to 0.1 weight/volume percent; the concentration of the amino acid protectant is approximately from 10 to 200 mM; and the concentration of the buffer is approximately from 1 to 50 mM; wherein the pH of the formulation is approximately from 5 to 7.

In another embodiment, in the stable solution formulation of the $ET_AR$ antibody provided herein, the concentration of the $ET_AR$ antibody is approximately 25, 50, 75, or 100 mg/mL; the concentration of the surfactant is approximately 0.04 weight/volume percent; the concentration of the amino acid protectant is approximately 140 mM; and the concentration of the buffer is approximately 20 mM; wherein the pH of the formulation is approximately from 5 to 6.

In yet another embodiment, the stable pharmaceutical solution formulation of the $ET_AR$ antibody provided herein also comprises a polyol protectant.

In one embodiment, in the stable solution formulation of the $ET_AR$ antibody provided herein, the concentration of the polyol described herein is approximately ranging from 0.1% to 50%, from 1% to 20%, from 1% to 15%, from 2% to 10%, or from 4% to 10%. In another embodiment, in the stable pharmaceutical solution formulation of the $ET_AR$ antibody provided herein, the concentration of the polyol described herein is approximately from 4 to 10 weight/volume percent. In yet another embodiment, in the stable pharmaceutical solution formulation of the $ET_AR$ antibody provided herein, the concentration of the polyol described herein is approximately 1, 1.5, 2, 2.5, 3, 3.5, 4, 4.5, 5, 5.5, 6, 6.5, 7, 7.5, 8, 8.5, 9, 9.5, or 10 weight/volume percent.

In one embodiment, the polyol protectant described herein is sorbitol, mannitol, sucrose, or trehalose. In another embodiment, the polyol protectant described herein is sorbitol or mannitol.

In one embodiment, in the stable solution formulation of the $ET_AR$ antibody provided herein, the concentration of the $ET_AR$ is approximately from 10 to 200 mg/mL; the concentration of the surfactant is approximately from 0.01 to 0.1 weight/volume percent; the concentration of the polyol protectant is approximately from 1 to 20 weight/volume percent; and the concentration of the buffer is approximately from 1 to 50 mM; wherein the pH of the formulation is approximately from 5 to 7.

In another embodiment, in the stable solution formulation of the $ET_AR$ antibody provided herein, the concentration of the $ET_AR$ antibody is approximately 25, 50, 75 or 100 mg/mL; the concentration of the surfactant is approximately 0.04 weight/volume percent; the concentration of the polyol protectant is approximately from 4 to 10 weight/volume percent; and the concentration of the buffer is approximately 20 mM; wherein the pH of the formulation is approximately from 5 to 6.

In another embodiment, the stable solution formulation of the $ET_AR$ antibody provided herein also comprises a metal chelator.

In one embodiment, in the stable solution formulation of the $ET_AR$ antibody provided herein, the concentration of the metal chelator described herein is approximately ranging from 0.001 mM to 1 mM, from 0.005 mM to 0.5 mM, or from 0.01 mM to 0.2 mM. In another embodiment, in the stable solution formulation of the $ET_AR$ antibody provided herein, the concentration of the metal chelator described herein is approximately from 0.01 mM to 0.2 mM. In yet another embodiment, in the stable solution formulation of the $ET_AR$ antibody provided herein, the concentration of the metal chelator described herein is approximately 0.01 mM, 0.02 mM, 0.03 mM, 0.04 mM, 0.05 mM, 0.06 mM, 0.07 mM, 0.08 mM, 0.09 mM, or 0.1 mM. In yet another embodiment, in the stable solution formulation of the $ET_AR$ antibody provided herein, the concentration of the metal chelator described herein is approximately 0.01 mM, 0.02 mM, 0.03 mM, 0.04 mM, 0.05 mM, 0.06 mM, 0.07 mM, 0.08 mM, 0.09 mM, or 0.1 mM. In still another embodiment, in the stable solution formulation of the $ET_AR$ antibody provided herein, the concentration of the metal chelator described herein is approximately 0.03 mM, 0.04 mM, 0.05 mM, 0.06 mM, or 0.07 mM.

In one embodiment, the metal chelator described herein is EDTA, DTPA, or EGTA. In another embodiment, the metal chelator described herein is EDTA.

In one embodiment, in the stable solution formulation of the $ET_AR$ antibody provided herein, the concentration of the $ET_AR$ antibody is approximately from 10 to 200 mg/mL; the concentration of the metal chelator is approximately from 0.01 to 0.2 mM; the concentration of the surfactant is approximately from 0.01 to 0.1 weight/volume percent; the concentration of the amino acid protectant is approximately from 10 to 200 mM; and the concentration of the buffer is approximately from 1 to 50 mM; wherein the pH of the formulation is approximately from 5 to 7.

In another embodiment, in the stable solution formulation of the $ET_AR$ antibody provided herein, the concentration of the $ET_AR$ antibody is approximately 25, 50, 75, or 100 mg/mL; the concentration of the metal chelator is approximately 0.05 mM; the concentration of the surfactant is approximately 0.04 weight/volume percent; the concentration of the amino acid protectant is approximately 140 mM; and the concentration of the buffer is approximately 20 mM; wherein the pH of the formulation is approximately from 5 to 6.

In one embodiment, in the stable solution formulation of the $ET_AR$ antibody provided herein, the concentration of the $ET_AR$ antibody is approximately from 10 to 200 mg/mL; the concentration of the metal chelator is approximately from 0.01 mM to 0.2 mM; the concentration of the surfactant is approximately from 0.01 to 0.1 weight/volume percent; the concentration of the polyol protectant is approximately from 1 to 20 weight/volume percent; and the concentration of the buffer is approximately from 1 to 50 mM; wherein the pH of the formulation is approximately from 5 to 7.

In another embodiment, in the stable solution formulation of the $ET_AR$ antibody provided herein, the concentration of the $ET_AR$ antibody is approximately 25, 50, or 100 mg/mL; the concentration of the metal chelator is approximately 0.05 mM; the concentration of the surfactant is approximately 0.04 weight/volume percent; the concentration of the polyol protectant is approximately from 4 to 10 weight/volume percent; and the concentration of the buffer is approximately 20 mM; wherein the pH of the formulation is approximately from 5 to 6.

In another embodiment, the stable solution formulation of the $ET_AR$ antibody provided herein also comprises an antioxidant.

In one embodiment, in the stable solution formulation of the $ET_AR$ antibody provided herein, the concentration of the antioxidant described herein is approximately ranging from 0.1 mM to 50 mM, from 0.5 mM to 20 mM, or from 1 mM to 10 mM. In another embodiment, in the stable solution formulation of the $ET_AR$ antibody provided herein, the concentration of the antioxidant described herein is approximately from 1 to 10 mM. In yet another embodiment, in the stable solution formulation of the $ET_AR$ antibody provided herein, the concentration of the antioxidant described herein is approximately 1 mM, 2 mM, 3 mM, 4 mM, 5 mM, 6 mM, 7 mM, 8 mM, 9 mM, or 10 mM. In still another embodiment, in the stable solution formulation of the $ET_AR$ antibody provided herein, the concentration of the antioxidant described herein is approximately 3 mM, 4 mM, 5 mM, 6 mM, or 7 mM.

In one embodiment, the antioxidant described herein is methionine, vitamin-C, thiosulfate, thiosulfate, or benzyl methionine. In another embodiment, the antioxidant described herein is methionine.

In one embodiment, in the stable solution formulation of the $ET_AR$ antibody provided herein, the concentration of the $ET_AR$ antibody is approximately from 10 to 200 mg/mL; the concentration of the antioxidant is approximately from 1 to 10 mM; the concentration of the surfactant is approximately from 0.01 to 0.1 weight/volume percent; the concentration of the amino acid protectant is approximately from 10 to 200 mM; and the concentration of the buffer is approximately from 1 to 50 mM; wherein the pH of the formulation is approximately from 5 to 7.

In another embodiment, in the stable solution formulation of $ET_AR$ antibody provided herein, the concentration of the $ET_AR$ antibody is approximately 25, 50, 75, or 100 mg/mL; the concentration of the antioxidant is approximately 5 mM; the concentration of the surfactant is approximately 0.04 weight/volume percent; the concentration of the amino acid protectant is approximately 140 mM; and the concentration of the buffer is approximately 20 mM; wherein the pH of the formulation is approximately from 5 to 6.

In one embodiment, the stable solution formulation of $ET_AR$ antibody provided herein, in the concentration of the $ET_AR$ antibody is approximately from 10 to 200 mg/mL; the concentration of the antioxidant is approximately from 1 mM to 10 mM; the concentration of the surfactant is approximately from 0.01 to 0.1 weight/volume percent; the concentration of the polyol protectant is approximately from 1 to 20 weight/volume percent; and the concentration of the buffer is approximately from 1 to 50 mM; wherein the pH of the formulation is approximately from 5 to 7.

In another embodiment, in the stable solution formulation of $ET_AR$ antibody provided herein, the concentration of the $ET_AR$ antibody is approximately 25, 50, 75, or 100 mg/mL; the concentration of the antioxidant is approximately 5 mM; the concentration of the surfactant is approximately 0.04 weight/volume percent; the concentration of the polyol protectant is approximately from 4 to 10 weight/volume percent; and the concentration of the buffer is approximately 20 mM; wherein the pH of the formulation is approximately from 5 to 6.

In one embodiment, the stable pharmaceutical solution formulation of the $ET_AR$ antibody provided herein comprises:

an $ET_AR$ monoclonal antibody, at 10-150 mg/mL;

a metal chelator at 0.1 mM to 1 mM;

a surfactant at 0.01% to 0.1%;

a polyol protectant at 1% to 50% or an amino acid protectant at 10 to 200 mM; and a buffering system, providing a pH of 5.0-7.0.

In another embodiment, the stable pharmaceutical solution formulation of the $ET_AR$ antibody provided herein comprises:

an $ET_AR$ monoclonal antibody at 10 to 150 mg/mL;

a metal chelator at 0.02 mM to 0.2 mM;

a surfactant at 0.01% to 0.1%;

a polyol protectant at 1% to 10% or an amino acid protectant 50 to 200 mM; and a buffering system, providing a pH of 5.3-6.5.

In one embodiment, the stable pharmaceutical solution formulation of the $ET_AR$ antibody provided herein comprises:

an $ET_AR$ monoclonal antibody at 10 to 150 mg/mL;

a metal chelator at 0-1 mg/mL;

a surfactant at 0-0.1%;

a polyol protectant at 0-50% or an amino acid protectant at 0-200 mM; and a buffering system, providing a pH of 5.0-7.0.

In another embodiment, the stable pharmaceutical solution formulation of the $ET_AR$ antibody provided herein comprises:

an $ET_AR$ monoclonal antibody at 10-150 mg/mL;

EDTA at 0-0.1 mg/mL a surfactant at 0-0.1%;

a polyol protectant at 0-10% or an amino acid protectant at 50-200 mM; and a buffering system, providing a pH of 5.3-6.5.

In one embodiment, the stable pharmaceutical solution formulation of the $ET_AR$ antibody provided herein is an aqueous solution. In another embodiment, the stable formulation of the pharmaceutical $ET_AR$ antibody provided herein is a sterile solution.

In one embodiment, the stability of the stable pharmaceutical solution formulation of the $ET_AR$ antibody provided herein is determined by the extent of aggregation of the $ET_AR$ antibody. In one embodiment, the stable pharmaceutical solution formulation of the $ET_AR$ antibody provided herein, after stored at about 40° C. and about 75% humidity for 1, 2, 3, 6, 12, or 24 months, contains no more than 20%, 15%, 10%, 8%, 6%, 5,%, 4%, 3%, 2%, 1%, or 0.1% of an aggregated $ET_AR$ antibody. In another embodiment, the stable pharmaceutical solution formulation of the $ET_AR$ antibody provided herein, after stored at room temperature and about 65% humidity for 3, 6, 12, or 24 months, contains no more than 20%, 15%, 10%, 8%, 6%, 5%, 4%, 3%, 2%, 1%, or 0.1% of an aggregated $ET_AR$ antibody. In yet another embodiment, the stable pharmaceutical solution formulation of the $ET_AR$ antibody provided herein, after stored at 2-8° C. for 6, 12, 18, 24, 36 or 48 months, contains no more than 20%, 15%, 10%, 8%, 6%, 5%, 4%, 3%, 2%, 1%, or 0.1% of an aggregated $ET_AR$ antibody.

In another embodiment, the stability of the stable pharmaceutical solution formulation of the $ET_AR$ antibody provided herein is determined by the extent of degradation of the $ET_AR$ antibody. In one embodiment, the stable pharmaceutical solution formulation of the $ET_AR$ antibody provided herein, after stored at about 40° C. and about 75% humidity for 1, 2, 3, 6, 12 or 24 months, has a degree of degradation of the $ET_AR$ antibody of no more than 20%, 15%, 10%, 8%, 6%, 5%, 4%, 3%, 2%, 1%, or 0.1%. In another embodiment, the stable pharmaceutical solution formulation of the $ET_AR$ antibody provided herein, after stored at room temperature and about 65% humidity for 3, 6, 12, or 24 months, has a degree of degradation of the $ET_AR$ antibody of no more than 20%, 15%, 10%, 8%, 6%, 5%, 4%, 3%, 2%, 1%, or 0.1%. In yet another embodiment, the stable pharmaceutical solution formulation of the $ET_AR$ antibody provided herein, after stored at 2-8° C. for 6, 12, 18, 24, 36 or 48 months, has a degree of degradation of the $ET_AR$ antibody of no more than 20%, 15%, 10%, 8%, 6%, 5%, 4%, 3%, 2%, 1%, or 0.1%.

In one embodiment, the aggregation of the $ET_AR$ antibody and the loss of a monomeric $ET_AR$ antibody are determined by SEC-HPLC.

In another embodiment, the stability of the stable pharmaceutical solution formulation of the $ET_AR$ antibody provided herein is determined by the change in the biological activity of the $ET_AR$ antibody. In one embodiment, the $ET_AR$ antibody in the stable pharmaceutical solution formulation of the $ET_AR$ antibody provided herein, after stored at about 40° C. and about 75% humidity for 1, 2, 3, 6, 12 or 24 months, has a biological activity of no less than 40%, 50%, 60%, 70%, 80%, 90%, 95%, 96%, 97%, 98%, 99%, or 99.9% of its original biological activity. In another embodiment, the $ET_AR$ antibody in the stable pharmaceutical solution formulation of the $ET_AR$ antibody provided herein, after stored under room temperature and about 65% humidity for 3, 6, 12, or 24 months, has a biological activity of no less than 50%, 60%, 70%, 80%, 90%, 92%, 94%, 95%, 96%, 97%, 98%, 99%, or 99.9% of its original biological activity. In yet another embodiment, the $ET_AR$ antibody in the stable pharmaceutical solution formulation of the $ET_AR$ antibody provided herein, after stored under temperature of 2-8° C. for 6, 12, 18, 24, 36 or 48 months, has a biological activity of no less than 50%, 55%, 60%, 65%, 70%, 75%, 80%, 85%, 90%, 92%, 94%, 95%, 96%, 97%, 98%, 99%, or 99.9% of its original biological activity.

In one embodiment, the change in the biological activity of the $ET_AR$ antibody is determined by a calcium flux detection method to determine the ability of an $ET_AR$ antibody to inhibit an $ET_AR$ in vitro.

Methods of Treatment

In one embodiment, provided herein is a method of lowering hypertension (for example, PAH) in a subject, comprising administering to the subject a therapeutically effective amount of a pharmaceutical composition provided herein, for example, a stable pharmaceutical solution formulation of an $ET_AR$ antibody provided herein.

In another embodiment, provided herein is a method of treating PAH in a subject, comprising administering to the subject a therapeutically effective amount of a pharmaceutical composition provided herein, for example, a stable pharmaceutical solution formulation of an $ET_AR$ antibody provided herein.

As used herein, the term "subject" refers to a mammal, including humans, and is used interchangeably with the term "patient." The term "treatment" encompasses alleviation or prevention of at least one symptom or other aspect of a disorder, or reduction of disease severity, and the like. An antibody provided herein needs not to provide a complete cure, or to eradicate every symptom or manifestation of a disease, to be an effective therapeutic agent. As is recognized in the pertinent field, therapeutic agents can reduce the severity of a given disease state, but need not to abolish every manifestation of the disease to be effective. Similarly, a prophylactic agent needs not to prevent the onset of a condition completely in order to be effective. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient an antibody in an amount and for a time sufficient to induce a sustained improvement over baseline of an indicator that reflects the severity of a particular disorder.

A pharmaceutical composition can be administered by any suitable technique, including, but not limited to, parenterally, topically, or by inhalation. If injected, the pharmaceutical composition can be administered, for example, via an intra-articular, intravenous, intramuscular, intralesional, intraperitoneal or subcutaneous route, by bolus injection or continuous infusion. It is considered, for example, localized administration at the disease or injury site, such as transdermal administration and sustained release of an implant. Delivery by inhalation includes, for example, nasal or oral inhalation, use of a nebulizer, inhalation of an antibody in aerosol form, and the like. Other alternatives include oral preparations, including pills, syrups, or lozenges.

Advantageously, the antibodies provided herein, are administered in a composition comprising one or more additional components such as a physiologically acceptable carrier, excipient or diluent. The composition additionally comprises one or more physiologically active agents as described below. In many particular embodiments, the composition comprises one, two, three, four, five, or six physiologically active agents in addition to one or more antibodies (e.g., murine antibodies or humanized antibodies) provided herein.

In one embodiment, the pharmaceutical composition comprises a murine antibody or humanized antibody of the invention together with one or more substances selected from the group consisting of a buffer suitable for the antibody at a suitable pH, an antioxidant such as ascorbic acid, a low molecular weight polypeptide (such as those having fewer than 10 amino acids), a protein, an amino acid, a carbohydrate such as dextrin, a chelating agent such as EDTA, glutathione, a stabilizer, and an excipient. In accordance with appropriate industry standards, preservatives can also be added. The composition can be formulated as a lyophilizate using appropriate excipient solutions as diluents. Suitable components are nontoxic to recipients at the dosages and concentrations employed. Further examples of components that can be employed in pharmaceutical formulations are presented in Remington's Pharmaceutical Sciences, 16th Ed. (1980) and 20th Ed. (2000). Mack Publishing Company kits for use by medical practitioners are provided, including one or more antibodies of the invention and a label or other instructions for use in treating any of the conditions discussed herein. In one embodiment, the kit includes a sterile preparation of one or more human antibodies, which can be in the form of a composition as disclosed above, and can be in one or more vials.

Dosages and the frequency of administration can vary according to such factors as the route of administration, the particular antibodies employed, the nature and severity of the disease to be treated, whether the condition is acute or chronic, and the size and general condition of the subject. Appropriate dosages can be determined by procedures known in the pertinent art, e.g. in clinical trials that can involve dose escalation studies.

An antibody provided here can be administered, for example, once or more than once, e.g., at regular intervals over a period of time. In particular embodiments, a murine antibody or humanized antibody is administered over a period of at least once a month or more, e.g., for one, two, or three months or even indefinitely. For treating chronic conditions, long-term treatment is generally most effective. However, for treating acute conditions, administration for shorter periods, e.g., from one to six weeks, can be sufficient. In general, the humanized antibody is administered until the patient manifests a medically relevant degree of improvement over baseline for the chosen indicator or indicators.

One example of therapeutic regimens provided herein comprise subcutaneous injection of an antibody once a week, at an appropriate dosage, to treat a condition in which pulmonary arterial pressure levels play a role. Weekly or monthly administration of antibody would be continued until a desired result is achieved, e.g., the subject's symptoms subside. Treatment can resume as needed, or, alternatively, maintenance doses can be administered.

A subject's levels of pulmonary arterial pressure can be monitored before, during and/or after treatment with an antibody such as a humanized antibody, to detect changes, if any, in their levels. For some disorders, the incidence of elevated pulmonary arterial pressure can vary according to such factors as the stage of the disease. Known techniques can be employed for measuring pulmonary arterial pressure levels.

Particular embodiments of methods and compositions of the invention involve the use of an antibody and one or more $ET_AR$ antagonists for example, two or more antibodies of the invention, or an antibody of the disclosure and one or more other $ET_AR$ antagonists. In further embodiments, an antibody is administered alone or in combination with other agents useful for treating the condition with which the patient is afflicted. Examples of such agents include both proteinaceous and non-proteinaceous drugs. When multiple therapeutics are co-administered, dosages can be adjusted accordingly, as is recognized in the pertinent art. "Co-administration" and combination therapy are not limited to simultaneous administration, but also include treatment regimens in which an antibody is administered at least once during a course of treatment that involves administering at least one other therapeutic agent to the patient.

In another aspect, the method of preparing a medicament for treating pulmonary arterial hypertension and related disorders comprises a mixture of the antibody provided herein and pharmaceutically acceptable excipients. The preparation method of the medicament was as described above.

A composition, kit, and method related to an antibody specifically binding to a human endothelin receptor are further provided herein. Nucleic acid molecules and derivatives and fragments thereof comprising a part of or a full polynucleotide encoding a polypeptide interacting with an $ET_AR$, for example, nucleic acids encoding all or part of an endothelin receptor antibody, an antibody fragment or an antibody derivative, are also provided. A vector and plasmid comprising nucleic acids and cells and cell line comprising nucleic acids and/or a vector and plasmid are further provided herein. Methods provided herein include, for example, methods for preparation, identification or separation of an antibody interacting with a human $ET_AR$, for example, a method of an $ET_AR$ antibody, a method for determining whether an antibody binds to $ET_AR$, and a method for administering an antibody binding to an $ET_AR$ to an animal model.

The technical solutions described herein will be further understood by the following examples.

EXAMPLES

If not specified, the starting materials and equipment described herein are commercially available or commonly used in the art. The methods in the following examples, unless otherwise specified, are all conventional methods in the art.

1. Construction of a Stable Antigen Cell Line for Immunization

CHO-DHFR– cells were seeded into a 6-well plate. After 24 h culture, the cells were transfected with a pIRES plasmid (Clontech, commercial) modified to carry $hET_AR$ gene (see SEQ ID NO: 1 for the nucleotide sequence, and SEQ ID NO: 2 for the amino acid sequence). The transfection was carried out by following the transfection conditions recommended by Invitrogen for Lipofectamine 2000. Forty-eight hours after transfection, the medium was replaced with a complete medium containing 10 nM MTX (methotrexate). The medium was changed every 3 days for about two weeks until stable clones appeared. The dispersed cell colonies were detached from the plate and collected. After cells grew to about 50% confluence, the concentration of MTX was gradually increased for pressure selection up to 10 μM. The constructed stable cell lines were analyzed by FACS using a polyclonal antibody (Abcam) against $hET_AR$ to identify cell clones after pressure selection. A large amount of $hET_AR$ expression were detected on the selected CHO-DHFR-$hET_AR$ cell membranes. Finally through subcloning, six high-$ET_AR$ expression and stable cell lines were identified and obtained.

2. Preparation of Antibodies

An emulsion of the CHO-DHFR-$hET_AR$ whole cells and Freund's adjuvant was injected subcutaneously into BALB/c mice (6-8 weeks) at $2\times10^6$ cells/mouse. After 2 weeks, the mice were boosted with incomplete Freund's adjuvant emulsified immunogen and then boosted once every week. After immunization for 6 times in total, blood samples were collected from the clipped tail ends and centrifuged to collect the serum. The serum was analyzed for serum titers by FACS. After the acceptable antibody titers were achieved, the mice were sacrificed and their spleen cells were harvested under aseptic conditions. SP2/0 cells were collected at the logarithmic phase of growth with 3 min centrifugation at 2,000 rpm. The cell pellets were resuspended with serum-free culture medium, then centrifuged, resuspended for a second time and counted. Spleen cells and SP2/0 cells were mixed at ratio of SP2/0 cells:spleen cells ≥1:1, followed by 3 rounds of washing-centrifugation. After the pellets from the last centrifugation were detached, 1 mL of pre-warmed PEG-1350 was added dropwise (finished in 30 s), after pipette-mixing for 1 min, 30 mL of the pre-warmed serum-free medium (Invitrogen) was added slowly to terminate the PEG fusion. After 5 min centrifugation at 1,500 rpm, the cell pellets were resuspended in the fusion culture medium. Spleen cells (20,000) and feeder layer cells (5,000) in 100 μL were plated into each well of 96-well plates. Fused hybridoma cells and feeder layer cells were co-cultured in 96-well plates with HAT (sarcine, amethopterin and thymidine) selection to get rid of the non-fused cells. After 10 days, the supernatants of the hybridoma cells in the culture plates were collected for ELISA analysis.

3. ELISA Screening of Whole Cells

CHO-DHFR-hET$_4$R cells over-expressing hET$_4$R and CHO-DHFR– cells not expressing hET$_4$R were separately transferred into a 96-well plate and allowed to grow to 90% confluent. The supernatant of the culture medium was removed and attached cells were washed twice with PBS, then 100 μL, 100% methanol was added to fix the cells for 10 min at 4° C. Then 100 μL freshly made 0.6% H$_2$O$_2$-PBS was added, and after incubation at room temperature for 20 min, the cells were washed twice with PBS. After blocked with PBS-1% BSA solution, the hybridoma supernatant was added and incubated for 90 min at 4° C. After several washes, 100 μL of the secondary antibody GxM-HRP-Fc (Sigma-Aldrich) was added into each well and incubated at 37° C. for 0.5 h. After five washings, 100 μL of TMB chromogenic substrate was added into each well and incubated at 37° C. for 15 min, and then 2M H$_2$SO$_4$ was added to terminate, read for OD$_{450}$ values. The positive control was the mouse serum after immunization; the negative control was the cell culture supernatant. As shown in FIG. 1, after initial analysis by ELISA, several hybridoma clones secreting anti-hET$_4$R antibodies were selected, and the stable secretory cell lines against hET$_4$R were obtained after cell cloning. Lastly, antibody supernatant secreted by hybridoma was verified by FACS analysis.

4. Cloning and Subcloning of Antibody Genes

Hybridoma cells secreting antibodies were collected. Hybridoma mRNA was extracted according to the manufacturer protocol of QIAGEN mRNA extraction kit. Then the extracted mRNA was transcribed reversely into cDNA. The reverse transcription primers were specific primers for the light and heavy chain constant regions of a mouse, with the heavy chain reverse transcription primer being (5'-TTTGGRGGGAAGATGAAGAC-3') (SEQ ID NO: 199), the light chain reverse transcription primers being (5'-TTAACACTCTCCCCTGTTGAA-3') (SEQ ID NO: 200) and (5'-TTAACACTCATTCCTGTTGAA-3') (SEQ ID NO: 201). RT-PCR reaction conditions were as following: 25° C. for 5 min, 50° C. for 60 min, and 70° C. for 15 min. Reversely transcribed cDNA was diluted with 0.1 mM TE to 500 μL, added into the ultrafiltration centrifuge tube (Amicon Ultra-0.5) and centrifuged at 2,000 g for 10 min. The filtrate was removed, 500 μL of 0.1 mM TE were added and centrifuged at 2,000 g for 10 min. The filtrate was removed and the preparation tube was placed in inversion to the new centrifugal tube, and centrifuged at 2,000 g for 10 min to obtain the purified cDNA. Purified cDNA (10 μL) was taken as a template, followed by addition of 4 μL 5× tailing buffer (Promega), 4 μL dATP (1 mM) and 10 U terminal transferase (Promega), mixing uniformly, and incubation at 37° C. for 5 min and then at 65° C. for 5 min. The PolyA tail cDNA was used as a template and PCR was performed to amplify light and heavy chain variable region genes of antibodies. Upstream primers were all oligodT, with heavy chain downstream primers being (5'-TGGACAGGGATCCAGAGTTCC-3') (SEQ ID NO: 202) and (5'-TGGACAGGGCTCCATAGTTCC-3') (SEQ ID NO: 203), and light chain downstream primer being (5'-ACTCGTCCTTGGTCAACGTG-3') (SEQ ID NO: 204). The PCR reaction conditions were: 95° C. for 5 min; 95° C. for 30 s, 56° C. for 30 s, 72° C. for 1 min, 40 cycles; and 72° C. for 7 min. The PCR products were connected to the PMD 18-T vector (Takara Bio) for sequencing. The sequences of the antibody clones were listed in Table 2.

PCR primers were designed based on the DNA sequences of the antibodies, thus the complete light chain, heavy chain signal peptides and variable domains and mouse IgG1 constant region were ligated into expression vector pTM5.

5. Antibody Humanization and Optimization

First of all, the sequences of light and heavy chain variable regions of the screened mouse antibodies were aligned with the homologous antibodies, using NCBI online antibody variable region sequence alignment tool (Ig Blast) to search the germline gene sequences of a humanized antibody (Ig Germline Gene sequence) homologous to the selected antibodies variable region sequence for humanization, and the humanized gene sequence with highest homology except CDR sequences was used as a template for CDR grafting to obtain humanized antibody variable region sequences and to synthesize humanized antibody light and heavy chain genes through a CRO. According to the sequences, PCR primers were designed and appropriate restriction enzyme sites were introduced at the 5' ends and 3' ends. By PCR, the humanized antibody variable regions were amplified and then combined with the human IgG2 or IgG4 constant region sequence to obtain whole recombinant humanized antibody sequences. The expression of the recombinant antibodies was achieved according to step 7, and their affinities to ET$_4$R was analyzed by FACS as described in step 9. The best humanized antibody candidate retaining affinity to ET$_4$R was selected from the group, and its variable region sequence was further improved by site-specific mutagenesis for improved affinity to ET$_4$R.

6. Subcloning of Genes of a Humanized Anti-hET$_4$R Antibody

The heavy and light chain variable region gene sequences of an optimized humanized antibody were synthesized by Genscript Biotechnology CO., LTD by introducing two restriction sites of NheI at the 5'-end and SalI at the 3'-end. The whole heavy chain variable region was ligated with a heavy chain constant region in an expression vector of pTM5. Similarly, by introducing NheI at the 5'-end and BsiwI at the 3'-end, the light chain variable region was ligated with a light chain constant region in the expression vector of pTM5.

7. Transient Expression of Anti-ET$_4$R Antibodies

A suspension of an HEK293 or CHO expressing cell line (5×10$^5$/mL) was inoculated to a shaker flask. After 24 h rotation at 37° C., the cell density reached 1×10$^6$/mL and were ready for transfection. Polyethylenimine (PEI) was used as a transfection reagent with an optimal mixing ratio of 3:1 for PEI to DNA (DNA amount, 0.5 μg/L×10$^6$ cells; the ratio of the antibody light chain DNA and antibody heavy chain DNA, 3:2). A mixture of both was added into the cell culture after 15 min incubation. The cells after treated with the PEI/DNA mixture were rotated for more than 24 h at 37°

C. and 5% $CO_2$. Then 0.5% of tryptone was added into the cell culture as a supplement required by expression, and after the completion of expression (more than 96 h), the cell supernatant was collected for the antibody purification and separation.

8. Purification and Preparation of Antibody

Cells and cellular debris were removed from the culture after centrifugation (8000 rpm, 15 min), and the supernatant was filtered through 0.45 μm filter for purification. The purification process was done through chromatography. First, the supernatant was passed through a G protein coupled affinity chromatography column, and antibodies bound to the G proteins remained in the column. The antibodies were eluted from the chromatography column using an eluent with pH of 3.0 or less. The low pH eluent was neutralized immediately with 1M Tris-HCl to keep the antibodies from denaturation and loss of activity. The antibody solution was then dialyzed over 16 h into a PBS buffer.

9. FACS Analysis of a Functional Antibody

PBS containing 10 mM EDTA was used to detach and collect $10^5$ CHO-DHFR-hET$_A$R cells into a 1.5 mL EP tube. The supernatant was removed after centrifugation and the negative control sample was resuspended with a loading buffer (PBS, 2% FBS). For the positive control, 200 μL antibody supernatant was added to resuspension cells and incubation at room temperature; the cells were then centrifuged at 1500 rpm to remove the supernatant, washed with a FACS loading buffer and centrifuged again. The cells were resuspended with addition (200 μL/well) of a FITC labeled goat anti-mouse fluorescent antibody at 1:50 dilution (BD Pharmingen) and incubated at room temperature for 30 min in the dark. Supernatant was removed after centrifugation, cells were washed with FACS loading buffer, centrifuged again and resuspended with the loading buffer for analysis. The recombinant antibody supernatant and CHO-DHFR-hET$_A$R cells had specific binding. Gray peak and dotted line peak were negative controls; the solid line peak, corresponding to the antibody supernatant, moved to the right significantly.

10. Calcium Influx Assay for a Functional Antibody

CHO-DHFR cells co-expressing hET$_A$R-Aequorin were seeded into a 96-well cell culture plate with 25000 cells per well and cultured at 37° C. overnight. The next day the culture supernatant was removed. Coelenterazine (50 μL) (Promega) was added in the dark and incubated at 37° C. for 2 h, and then 50 μL of a hybridoma supernatant or a purified antibody were added and incubated at 37° C. for 30 min. After the incubation, 50 μL endothelin 1 was added and the changes of calcium influx within 40 s were recorded by a SpectraMax L microplate reader (Molecular Devices). Different hybridoma supernatants inhibited the calcium influx mediated through hET$_A$R differently, and A-1 antibody significantly inhibited the calcium influx mediated through hET$_A$R. The recombinant anti-hET$_A$R functional antibody significantly inhibited calcium influx mediated through hET$_A$R, increasing with an increase in the antibody concentration.

11. Establishment of Hypoxia-Induced PAH Cynomolgus Model to Study the In Vivo Activity of an Antibody The acute hypoxia-induced pulmonary arterial hypertension (PAH) model of cynomolgus was codeveloped with Crown Bioscience Inc. (Taicang), and the efficacy of A-1 antibody as a single intravenous injection was evaluated in this PAH model. All animals were fasted overnight and weighed, and then received a single intravenous injection of 10 mg/kg of A-1 antibody. Three hours later, the animals were anesthetized. The tricuspid regurgitation velocity by Doppler color echocardiography along with heart rate and oxygen saturation were monitored simultaneously. The baseline was obtained and the induction of 12% hypoxia was followed and at the same time the tricuspid regurgitation velocity was measured; Analysis was made to determine if the antibody would improve hypoxia-induced pulmonary arterial pressure under 12% hypoxia. After 48 h of administration, the tests were performed again. The animals were anesthetized, the tricuspid regurgitation velocity by Doppler color echocardiography along with heart rate and oxygen saturation were monitored simultaneously. The baseline was obtained and the induction of 12% hypoxia was followed and at the same time the tricuspid regurgitation velocity was measured. Analysis was made to determine if the antibody would still improve hypoxia-induced pulmonary arterial pressure. If the efficacy maintained after 48 h, 96 h later, hypoxia induction experiment was performed again. The area under the curve of pulmonary artery systolic pressure versus time was calculated, and by comparing the area under the curve, it was found that A-1 maintained the efficacy of reducing pulmonary artery pressure within 96 h.

12. Stable Pharmaceutical Solution Formulations of an ET$_A$R Antibody:

The followings are examples of stable pharmaceutical solution formulations of an ET$_A$R antibody:

Example 1

| Ingredients | Concentration |
| --- | --- |
| ET$_A$R antibody A-1 | 25 mg/mL |
| Sodium citrate | 20 mM |
| Arginine hydrochloride | 140 mM |
| TWEEN-80 | 0.04% |

The pH of the stable solution formulation of Example 1 is 5.8.

Example 2

| Ingredients | Concentration |
| --- | --- |
| ET$_A$R antibody A-1 | 50 mg/mL |
| Histidine | 20 mM |
| Arginine hydrochloride | 140 mM |
| TWEEN-80 | 0.04% |

The pH of the stable solution formulation of Example 2 is 5.8.

Example 3

| Ingredients | Concentration |
| --- | --- |
| ET$_A$R antibody A-1 | 50 mg/mL |
| Sodium citrate | 20 mM |
| Sorbitol | 4.5% |
| TWEEN-80 | 0.04% |

The pH of the stable solution formulation of Example 3 is 5.8.

Example 4

| Ingredients | Concentration |
| --- | --- |
| $ET_AR$ antibody A-1 | 25 mg/mL |
| Sodium citrate | 20 mM |
| Mannitol | 4.5% |
| TWEEN-80 | 0.04% |

The pH of the stable solution formulation of Example 4 is 5.8.

Example 5

| Ingredients | Concentration |
| --- | --- |
| $ET_AR$ antibody A-1 | 25 mg/mL |
| Sodium citrate | 20 mM |
| Sucrose | 9% |
| TWEEN-80 | 0.04% |

The pH of the stable solution formulation of Example 5 is 5.8.

Example 6

| Ingredients | Concentration |
| --- | --- |
| $ET_AR$ antibody A-1 | 25 mg/mL |
| Histidine | 20 mM |
| Sucrose | 9% |
| TWEEN-80 | 0.04% |

The pH of the stable solution formulation of Example 6 is 5.8.

Example 7

| Ingredients | Concentration |
| --- | --- |
| $ET_AR$ antibody A-1 | 50 mg/mL |
| Histidine | 20 mM |
| Arginine hydrochloride | 140 mM |
| Methionine | 5 mM |
| TWEEN-20 | 0.04% |

The pH of the stable solution formulation of Example 7 is 5.8.

Example 8

| Ingredients | Concentration |
| --- | --- |
| $ET_AR$ antibody A-1 | 50 mg/mL |
| Sodium citrate | 20 mM |
| Arginine hydrochloride | 140 mM |
| Methionine | 5 mM |
| TWEEN-20 | 0.04% |

The pH of the stable solution formulation of Example 8 is 5.8.

Example 9

| Ingredients | Concentration |
| --- | --- |
| $ET_AR$ antibody A-1 | 100 mg/mL |
| Sodium citrate | 20 mM |
| Arginine hydrochloride | 140 mM |
| TWEEN-20 | 0.04% |
| EDTA | 0.05 mM |

The pH of the stable solution formulation of Example 9 is 5.8.

Example 10

| Ingredients | Concentration |
| --- | --- |
| $ET_AR$ antibody A-1 | 100 mg/mL |
| Histidine | 20 mM |
| Arginine hydrochloride | 140 mM |
| TWEEN-20 | 0.04% |
| EDTA | 0.05 mM |

The pH of the stable solution formulation of Example 10 is 5.8.

13. Methods for Analyzing Stable Pharmaceutical Solution Formulations of an $ET_AR$ Antibody:

Size Exclusion High Performance Liquid Chromatography (SEC-HPLC) for Analyzing Monomeric and Aggregated $ET_AR$ Antibodies SEC-HPLC was used to determine the formation of aggregates (soluble aggregates) of the $ET_AR$ antibody and the loss of its monomeric form. In Agilent 1100 HPLC at 25° C., a TSK-G3000SWxl high performance SEC column was flushed with 200 mM phosphate buffer (pH 6.8) as a mobile phase till the baseline of the UV absorbance was constant and stable. A stable pharmaceutical solution formulation of the $ET_AR$ antibody at the concentration of 1 to 3 mg/mL (pre-diluted with the mobile phase) was injected in the amount of 50 µL. The sample was eluted with the mobile phase at a flow rate of 0.5 mL/min and the absorbance at UV 280 nm was recorded. After each run, the AUCs of absorbance peaks of the monomer (the main peak), dimers and multimers were calculated, the percentage of the AUC for the main peak versus the total AUC was calculated and reported as the purity of the sample.

Capillary Electrophoresis (CE-SDS) for Analyzing the Purities of Reduced and Non-Reduced $ET_AR$ Antibody Samples A capillary electrophoresis apparatus (Beckmann MDQP/ ACE) was used, and samples were treated with an IgG purity/heterogeneity assay kit (Beckmann) by adding beta-mercaptoethanol to reduced samples or iodoacetamide to non-reduced samples. Beckmann non-coated capillaries were used to separate, and the samples were loaded at a concentration of 1 mg/mL automatically. After finishing loading a sample, separation was performed at 15 kV reverse voltage, and a UV214 nm absorbance time curve was recorded. When the process was finished, the absorption peaks at UV214 nm of the main peak, fragments and aggregates were integrated. For a non-reduced sample, the ratio of the main peak over total area was calculated, which represents the purity of the non-reduced sample. For a reduced sample, the ratio of light and heavy chain peak areas over the total area was calculated, which represents the purity of the reduced sample.

Calcium Flux Detection Method to Determine Inhibitory Activity of an $ET_AR$ Antibody on an $ET_AR$ In Vitro $ET_AR$-Aq-#105 cells stably expressing $hET_AR$-Aequorin were seeded in a 96 well plate at a density of $3.5 \times 10^4$ cells/well and 100 μL/well, and the plate was placed at 37° C., 5% $CO_2$ overnight. 100 μL of Colenterazine-h (0.23 μM stock solution) was diluted into 3.2 mL of a DMEM/F12 medium without phenol red. The plate was removed from the incubator, the medium was aspirated, 50 μL/well of diluted Colenterazine-h was added (in the dark), and the plate was placed in the 37° C. incubator for 2 hours. Reference antibody A-1 and test samples were diluted serially, and 50 μL/well of the dilutions were added to the 96 well plate (in the dark). After addition of the samples, the plate was placed in an incubator at 37° C. and 5% $CO_2$ for another 30 min. The fluorescence intensity of each well was read on a microplate reader. The read values of three wells with only DMEM/F12 medium (no phenol red) were the background values, and the rest of the wells were added with 20 nM endothelin-1.

The read data were pasted to Excel for analysis, and the time point of the peak fluorescent intensity was selected as the calculation value. The average of the fluorescence values of the blank controls was obtained, and the average value was then subtracted from each original value. After processing, the values of the maximum fluorescence intensities were averaged, and the relative percentage of each well to the average of the maximum response average was calculated finally. Through Prism software, the percentage and concentration of each well were used to calculate $IC_{50}$ values for the reference $ET_AR$ antibody and the test samples, as well as curve fitting correlation coefficients $R^2$. The biological activity of a test sample (%)=($IC_{50}$ of the reference/$IC_{50}$ of the test sample)×100.

14. pH and Buffer Screening:

pH was screened from a pH single factor experiment with antibody A-1 in a 20 mM sodium citrate buffer with pH between 4.7 and 6.3, with a total of 7 experiments (see Table 3) to determine the appearance and A340 absorption of antibody A-1 after 2-hour in a 65° C. water bath. As shown in Table 3, the experimental results indicated that antibody A-1 had relatively good thermal stability within pH 5.0 and 5.7 to 6.3.

TABLE 3

Effect of pH on protein thermal stability at 65° C.

| Test | pH | A340 | Appearance |
|------|-----|-------|------------|
| 1 | 4.7 | 0.028 | Opalescence and large number of floc-like particles |
| 2 | 5.0 | 0.073 | Floc-like particles |
| 3 | 5.3 | 0.451 | Large number of particles |

TABLE 3-continued

Effect of pH on protein thermal stability at 65° C.

| Test | pH | A340 | Appearance |
|------|-----|-------|------------|
| 4 | 5.5 | 0.508 | Large number of particles |
| 5 | 5.7 | 0.218 | Large number of particles |
| 6 | 6.0 | 0.036 | Floc-like particles |
| 7 | 6.3 | 0.012 | Floc-like particles |

15. Effect of Concentrations and Types of a Buffer Salt on Protein Stability:

Based on the above pH screening result, further screening experiments were carried out on pH and buffers. The two buffer systems of sodium citrate and histidine were selected, and the experiment was designed with two influencing factors. Two sets of samples were prepared to buffer at 3 different pH values, 20 mM sodium citrate, 200 mM sodium chloride, 0.02% TWEEN-80 at pH 4.7, 5.1, and 5.3; 20 mM histidine, 200 mM sodium chloride, 0.02% TWEEN-80 at pH 5.7, 6.0, and 6.3 (See Table 4). 1 to 6 groups of accelerated degradation experiments were performed, and the concentration of antibody A-1 was kept at 50 mg/mL. The experimental conditions were freeze-thaw: freeze at −20° C., thaw at room temperature, 3 cycles; high temperature: 37° C. for 10 days, 13 days; illumination: 5000 lx, 300 μW/cm², 25° C., 5 days; testing parameters: appearance, visible particles, purity (SEC-HPLC, non-reduced CE-SDS), charge variant.

TABLE 4

Experimental design for buffer salt type and pH screening

| Formulation | Protein concentration (mg/mL) | Sodium citrate (mM) | Histidine salt (mM) | NaCl (mM) | TWEEN-80 (%) | pH |
|-------------|-------------|-------------|-------------|-------------|-------------|-------------|
| 1 | 50 | 20 | | 200 | 0.02 | 4.7 |
| 2 | 50 | 20 | | 200 | 0.02 | 5.1 |
| 3 | 50 | 20 | | 200 | 0.02 | 5.3 |
| 4 | 50 | | 20 | 200 | 0.02 | 5.7 |
| 5 | 50 | | 20 | 200 | 0.02 | 6.0 |
| 6 | 50 | | 20 | 200 | 0.02 | 6.3 |

The results were summarized in Tables 5 to 8. Experimental results indicated that freeze-thaw cycle didn't significantly affect antibody A-1, but based on the results at high temperatures and light exposure, lower pH of sodium citrate resulted readily in the aggregation and loss of purity. Antibody A-1 is relatively sensitive to light, especially in term of charge variant, and after 5 days of light exposure, the main peak dropped significantly and the basic peak decreased. Only formulation 4 changed little, followed by formulation 5. Therefore, formulation 4 was selected as the formulation for the next protectant screening.

TABLE 5

Appearance inspection results of formulation samples

| Formulation | 0 day | High temperature 10 days | High temperature 13 days | Freeze-and-thaw | Illumination 5 days |
|-------------|-------|-------------|-------------|-------------|-------------|
| 1 | Colorless and clear No visible particles | Slight opalescence No visible particles | Apparent opalescence No visible particles | Colorless and clear No visible particles | Opalescence No visible particles |
| 2 | Colorless and clear | Colorless and clear | Colorless and clear | Colorless and clear | Opalescence No visible |

TABLE 5-continued

| Formu-lation | 0 day | High temperature 10 days | High temperature 13 days | Freeze-and-thaw | Illumination 5 days |
|---|---|---|---|---|---|
| | No visible particles | No visible particles | No visible particles | No visible particles | particles |
| 3 | Colorless and clear | Colorless and clear | Colorless and clear | Colorless and clear | Opalescence |
| | No visible particles | No visible particles | No visible particles | No visible particles | No visible particles |
| 4 | Colorless and clear | Colorless and clear | Colorless and clear | Colorless and clear | Opalescence and slight yellow |
| | No visible particles | No visible particles | No visible particles | No visible particles | No visible particles |
| 5 | Colorless and clear | Colorless and clear | Colorless and clear | Colorless and clear | Slight yellow |
| | No visible particles | No visible particles | No visible particles | No visible particles | No visible particles |
| 6 | Colorless and clear | Colorless and clear | Colorless and clear | Colorless and clear | Slight yellow |
| | No visible particles | No visible particles | No visible particles | No visible particles | No visible particles |

TABLE 6

SEC purity (%) test results of formulation samples

| Formulation | 0 day | High temperature 10 days | High temperature 13 days | Freeze-and-thaw | Illumination 5 days |
|---|---|---|---|---|---|
| 1 | 98.05 | 86.32 | 84.60 | 98.01 | 92.11 |
| 2 | 98.01 | 96.56 | 95.78 | 97.95 | 92.84 |
| 3 | 97.99 | 97.56 | 96.72 | 97.93 | 93.39 |
| 4 | 98.05 | 97.85 | 97.05 | 98.02 | 95.12 |
| 5 | 98.04 | 97.45 | 97.08 | 98.02 | 95.08 |
| 6 | 98.03 | 97.94 | 97.16 | 98.01 | 94.43 |

TABLE 7

Non-reduced CE-SDS purity (%) test results of formulation samples

| Formulation | 0 day | High temperature 10 days | High temperature 13 days | Freeze-and-thaw |
|---|---|---|---|---|
| 1 | 96.50 | 93.71 | 92.59 | 95.80 |
| 2 | 96.78 | 94.77 | 89.90 | 95.81 |
| 3 | 96.40 | 95.59 | 95.47 | 95.76 |
| 4 | 96.20 | 95.55 | 95.47 | 95.77 |
| 5 | 96.12 | 95.55 | 95.84 | 96.13 |
| 6 | 96.22 | 95.61 | 95.89 | 95.21 |

TABLE 8

Changes of charge variant main peak (%) of formulation samples

| Formulation | 0 day | High temperature 10 days | High temperature 13 days | Freeze-and-thaw |
|---|---|---|---|---|
| 1 | 59.80 | 62.53 | 62.57 | 58.82 |
| 2 | 59.53 | 62.42 | 63.84 | 59.08 |
| 3 | 59.88 | 62.64 | 63.30 | 58.90 |
| 4 | 59.49 | 62.09 | 60.42 | 58.73 |
| 5 | 59.56 | 61.17 | 61.13 | 59.23 |
| 6 | 60.54 | 60.76 | 60.89 | 59.07 |

16. Protectant Screening:

Experimental Plan

Two groups of experiments were performed. Six protectants were tested in the first group of experiments, and they are 5% sucrose, 2% mannitol, 2% sorbitol, 100 mM NaCl, 140 mM arginine, and 150 mM proline. In this group, the protein concentration of antibody A-1 was 60 mg/mL, the concentration of histidine as a buffer salt was 20 mM, TWEEN-80 concentration was 0.02%, and pH was 5.8. The experimental conditions were freeze-thaw: freeze at −20° C., thaw at room temperature, 5 cycles; high temperature: 40° C. for 10 days, 13 days; illumination: 5000 lx, 300 µW/cm$^2$, 25° C., 5 days; shaking: 300 rpm, room temperature for 3 days in the dark; testing parameters: appearance, visible particles, purity (SEC-HPLC, non-reduced CE-SDS), charge variant. The design plan is shown in Table 9.

TABLE 9

Experimental design for protectant screening

| Formulation | NaCl (mM) | Sucrose (%) | Mannitol (%) | Sorbitol (%) | Arginine (mM) | Proline (mM) |
|---|---|---|---|---|---|---|
| 7 | 100 | 5 | — | — | — | — |
| 8 | 100 | — | 2 | — | — | — |
| 9 | 100 | — | — | 2 | — | — |
| 10 | — | — | — | — | 140 | — |
| 11 | — | — | — | — | — | 150 |
| 12 | 100 | — | 2 | — | — | — |

The second group of experiments were performed based on the first group of experiments, and sodium citrate was selected as the buffer system. The concentration of sodium citrate was 20 mM, pH was 5.8, and the concentration of antibody A-1 was about 30 mg/mL. In the F1 formulation, arginine was replaced with arginine hydrochloride, and its concentration was 140 mM. Further, the experiment for the selection of a protectant was performed, and conditions of high temperature and illumination were modified to 40° C./2 watts, 1 month, 5000 lx, 0 day, 2 days, 5 days, 10 days. The design plan is shown in Table 10.

TABLE 10

| | Protectant screening design table | | | | | | | |
| Formulation | Protein Conc. (mg/mL) | Sodium citrate (mM) | Arginine HCl (mM) | Sucrose (%) | Mannitol (%) | Sorbitol (%) | Tween-80 (%) | pH |
|---|---|---|---|---|---|---|---|---|
| F1 | 26.4 | 20 | 140 | — | — | — | 0.04 | 5.8 |
| F2 | 30.2 | 20 | — | 5 | — | — | 0.04 | 5.8 |
| F3 | 29.4 | 20 | — | — | 5 | — | 0.04 | 5.8 |
| F4 | 29.8 | 20 | — | — | — | 5 | 0.04 | 5.8 |

Experimental Results

The results of the first group of experiments showed that, after 5 days of illumination, the color of 6 formulation samples all turned yellow to different degrees. The results of SEC-HPLC indicated, in comparison with other protectants, arginine was more effective in reducing aggregate formation. (Table 11).

For 7, 13 days at high temperature 40° C.: the results of SEC-HPLC showed, in comparison with the monomer purity (98%) at 0 day, there was no significant difference in the decrease of monomer in each formulation, and there was even less reduction of purity for the formulations containing sucrose, arginine and proline. The results are shown in Table 12 below.

TABLE 11

| | Test results of formulation samples after illumination | | | | | |
| Formulation | Appearance | Visible particles | Aggregate (%) | Dimer (%) | Monomer (%) | Fragment (%) |
|---|---|---|---|---|---|---|
| 7 | Slight yellow | No visible particles | 0.66 | 4.92 | 93.66 | 0.76 |
| 8 | Slight yellow | No visible particles | 0.61 | 4.77 | 93.97 | 0.65 |
| 9 | Slight yellow | No visible particles | 0.62 | 4.79 | 93.95 | 0.64 |
| 10 | Slight yellow | No visible particles | 0.44 | 3.90 | 95.15 | 0.51 |
| 11 | Slight yellow | No visible particles | 0.73 | 5.07 | 93.60 | 0.61 |
| 12 | Slight yellow | No visible particles | 0.66 | 4.90 | 93.81 | 0.63 |

TABLE 12

| | Test results of formulation samples after high temperature | | | | |
| Formulation | Day | Appearance | Visible particle | Monomer (%) | Charge variant main peak ratio (%) |
|---|---|---|---|---|---|
| 7 | 7 | Colorless and clear | No visible particles | 97.88 | 65.44 |
| 8 | 7 | Colorless and clear | No visible particles | 97.50 | 61.50 |
| 9 | 7 | Colorless and clear | No visible particles | 97.44 | 63.14 |
| 10 | 7 | Colorless and clear | No visible particles | 97.77 | 63.50 |
| 11 | 7 | Colorless and clear | No visible particles | 97.83 | 65.24 |
| 12 | 7 | Colorless and clear | No visible particles | 97.48 | 63.52 |
| 7 | 13 | Colorless and clear | No visible particles | 97.40 | 65.33 |
| 8 | 13 | Slight opalescent | No visible particles | 97.31 | 61.32 |
| 9 | 13 | Colorless and clear | No visible particles | 97.15 | 64.84 |
| 10 | 13 | Colorless and clear | No visible particles | 97.34 | 66.03 |
| 11 | 13 | Slight opalescent | No visible particles | 97.34 | 65.44 |

TABLE 12-continued

| | Test results of formulation samples after high temperature | | | | |
| Formulation | Day | Appearance | Visible particle | Monomer (%) | Charge variant main peak ratio (%) |
|---|---|---|---|---|---|
| 12 | 13 | Slight opalescent | No visible particles | 97.25 | 65.70 |

The test results of shaking and freeze-thaw (see Table 13) indicated that, in comparison with 0 day, there was no significant difference for the aggregate and charge variant.

In the second group of experiments, the sodium citrate was used as the buffer, and the results indicates that, after high temperature and illumination, the formulation of antibody A-1 showed slight opalescence (see Table 14). Comparing the effects of several protectants, we considered arginine hydrochloride the best in preserving the purity of antibody A-1 (see Table 15). The illumination induced significant change of charge variants (see Table 16), therefore, it was recommended to store antibody A-1 in the dark.

TABLE 13

| | Test results of formulation samples after shaking and freeze-thaw | | | | | |
| | SEC purity (%) | | | Ratio of charge variant main peak (%) | | |
| Formulation | 0 day | Shaking | Freeze-thaw | 0 day | Shaking | Freeze-thaw |
|---|---|---|---|---|---|---|
| 7 | 97.98 | 98.03 | 97.97 | 60.02 | 60.24 | 58.60 |
| 8 | 97.95 | 98.00 | 97.88 | 59.72 | 59.97 | 59.07 |
| 9 | 97.99 | 98.03 | 97.95 | 59.51 | 59.71 | 58.92 |
| 10 | 98.03 | 98.08 | 97.96 | 59.57 | 59.65 | 59.13 |
| 11 | 98.00 | 98.01 | 97.97 | 59.44 | 60.40 | 59.22 |
| 12 | 97.99 | 98.02 | 97.92 | 59.39 | 59.58 | 58.95 |

TABLE 14

Change of appearance and visible particles of formulation samples

| | | Appearance | |
|---|---|---|---|
| Formulation | 0 day | Illumination 10 days | 40° C., 1 month |
| F1 | Clear No visible particles | Slight opalescence No visible particles | Slight opalescence No visible particles |
| F2 | Clear No visible particles | Slight opalescence No visible particles | Slight opalescence No visible particles |
| F3 | Clear No visible particles | Slight opalescence No visible particles | Slight opalescence No visible particles |
| F4 | Clear No visible particles | Slight opalescence No visible particles | Slight opalescence No visible particles |

TABLE 15

Test results of SEC purities (%) of formulation samples

| | | | | Illumination | | | High temperature | High temperature |
|---|---|---|---|---|---|---|---|---|
| Formulation | 0 day | Shaking | Freeze-thaw | 2 days | 5 days | 10 days | 2 weeks | 1 month |
| F1 | 98.54 | 98.60 | 98.54 | 98.36 | 98.13 | — | 98.53 | 98.53 |
| F2 | 98.40 | 98.30 | 98.44 | 98.27 | 97.94 | 97.83 | 97.92 | 96.2 |
| F3 | 98.36 | 98.26 | 96.32 | 97.96 | 97.96 | 97.22 | 97.94 | 95.85 |
| F4 | 98.40 | 98.30 | 98.44 | 98.18 | 97.83 | 97.63 | 97.72 | 94.92 |

Note:

the sample of illumination for 10 days was left out by mistake, therefore, the SEC purity and charge variant data of the sample was not available.

TABLE 16

Test results of charge variant main peak (%) of formulation samples

| | | | | Illumination | | | High temperature | High temperature |
|---|---|---|---|---|---|---|---|---|
| Formulation | 0 day | Shaking | Freeze-thaw | 2 days | 5 days | 10 days | 2 weeks | 1 month |
| F1 | 70.40 | 72.08 | 72.97 | 60.34 | 48.26 | — | 59.64 | 56.41 |
| F2 | 69.64 | 72.86 | 72.81 | 67.96 | 49.51 | 47.59 | 56.86 | 63.79 |
| F3 | 72.19 | 72.71 | 73.84 | 65.12 | 49.56 | 51.03 | 69.05 | 61.88 |
| F4 | 70.24 | 72.82 | 70.2 | 63.98 | 49.04 | 49.54 | 53.90 | 61.22 |

17. The Experiment on the Factors Affecting Antioxidants: Experimental Plan

The experiment was to evaluate the protective effect of 0.0187 mg/mL EDTA, and two buffers were selected, 20 mM histidine salt and 20 mM sodium citrate with 0.02% and 0.1% of Tween-80 (Table 17). The concentration of antibody A-1 was 60 mg/mL, arginine hydrochloride was 140 mM, and pH was 5.8. The three formulation samples were subject to accelerated degradation experiment, and the experimental condition was illumination: 5000 1x, 300 $\mu W/cm^2$, 25° C., 3 days, 6 days; the test items: appearance, visible particles, purity (SEC-HPLC), and charge variant.

TABLE 17

Antioxidant screening table

| Formulation | Histidine salt (mM) | Sodium citrate (mM) | EDTA (mg/mL) | Tween-80 (%) |
|---|---|---|---|---|
| 13 | 20 | — | 0.0187 | 0.02 |
| 14 | 20 | — | — | 0.1 |
| 15 | — | 20 | — | 0.02 |

Based on the above experiment, methionine was added as a screening antioxidant, and the detailed plan was in Table 18. The experiment conditions were: high temperature 40° C. for 2 weeks, 1 month; illumination 5000 lx for 0 day, 2 days, 5 days, 10 days.

TABLE 18

Methionine formulation screening table

| Formulation | Concentration (mg/mL) | Sodium citrate (mM) | Arginine hydrochloride (mM) | Methionine (mM) | Tween-80 (%) | pH |
|---|---|---|---|---|---|---|
| F1-M | ~50 | 20 | 140 | — | 0.04 | 5.8 |
| F2-M | ~50 | 20 | 140 | 5 | 0.04 | 5.8 |
| F3-M | ~50 | 20 | 140 | 10 | 0.04 | 5.8 |

Experimental Results

Based on the results of two groups of experiments, neither of the two protectants affects antibody A-1 significantly. No difference was observed in the different concentrations of Tween used (Table 19, Table 20, Table 21, Table 22), but when using histidine as the formulation buffer salt, the formulation turned yellow after illumination, therefore, sodium citrate is a better choice as the formulation buffer salt. After three days of destruction with illumination, the SEC-HPLC peaks of formulation samples 13 to 15 decreased with no notable difference between them. The peak of the 3-day formulation sample is the same as 0 day's in the dark. After 6 days of destruction by illumination, the peak of sample 13 showed even more reduction, while sample 14 and 15 showed no further reduction. The peak of the 6-day formulation sample is the same as 0 day's in the dark.

TABLE 19

Test results of formulation samples after illumination

| Formulation | Condition | Appearance | Visible particle | SEC purity (%) |
|---|---|---|---|---|
| 13 | Illumination 3 days | Slightly yellow | No visible particles | 97.11 |
| 14 | Illumination 3 days | Very slightly yellow | No visible particles | 97.27 |

TABLE 19-continued

Test results of formulation samples after illumination

| Formulation | Condition | Appearance | Visible particle | SEC purity (%) |
|---|---|---|---|---|
| 15 | Illumination 3 days | Opalescence | No visible particles | 96.97 |
| 13 | Illumination 3 days | Clear and colorless | No visible particles | 98.07 |
| 15 | Illumination 3 days | Clear and colorless | No visible particles | 98.05 |
| 13 | Illumination 6 days | Slightly yellow | Tiny particles | 96.12 |
| 14 | Illumination 6 days | Slightly yellow | Tiny particles | 96.41 |
| 15 | Illumination 6 days | Opalescence | Tiny particles | 96.24 |
| 13 | Illumination 6 days | Clear and colorless | No visible particles | 97.97 |
| 15 | Illumination 6 days | Clear and colorless | No visible particles | 98.08 |

TABLE 20

Appearance, visible particles and purity change of formulation samples after high temperature 40° C.

| Formulation | SEC purity (%) | | | Appearance | | |
| --- | --- | --- | --- | --- | --- | --- |
| | 0 day | 1 week | 1 month | 0 day | 2 weeks | 1 month |
| F1-M | 98.51 | 98.65 | 97.30 | Slight opalescence No visible particles | Opalescence No visible particles | Opalescence No visible particles |
| F2-M | 98.50 | 98.67 | 97.37 | Slight opalescence No visible particles | Opalescence No visible particles | Opalescence No visible particles |
| F3-M | 98.53 | 98.66 | 97.53 | Slight opalescence No visible particles | Opalescence No visible particles | Opalescence No visible particles |

TABLE 21

Test results of the SEC purity (%) of formulation samples after illumination and high temperature

| Formulation | Illumination | | | | High temperature | High temperature |
| --- | --- | --- | --- | --- | --- | --- |
| | 0 day | 2 days | 5 days | 10 days | 2 weeks | 1 month |
| F1-M | 98.51 | 98.23 | 97.95 | 97.38 | 98.65 | 97.30 |
| F2-M | 98.50 | 98.23 | 97.98 | 97.75 | 98.67 | 97.37 |
| F3-M | 98.53 | 98.28 | 98.03 | 97.85 | 98.66 | 97.53 |

TABLE 22

Test results of the charge variant main peak (%) of formulation samples after illumination and high temperature

| Formulation | Illumination | | | | High temperature | High temperature |
| --- | --- | --- | --- | --- | --- | --- |
| | 0 day | 2 days | 5 days | 10 days | 2 weeks | 1 month |
| F1-M | 68.83 | 46.82 | 47.23 | 46.39 | 64.13 | 55.13 |
| F2-M | 70.16 | 45.53 | 48.85 | 45.87 | 62.43 | 57.05 |
| F3-M | 75.67 | 62.50 | 49.97 | 44.06 | 64.54 | 58.48 |

18. Long-Term and Accelerated Stability Study at Different Protein Concentrations:

Experimental Plan

After determining the initial formulation, we also did long-term and acceleration stability studies on the antibody A-1 at different concentrations. We set the antibody concentrations at 25, 50, and 100 mg/mL, and used the defined formulation to pursue long-term (4° C., 0 day, 1 month, 2 months, 3 months, 6 months, 9 months) and acceleration (25° C., 0 day, 1 month, 2 months, 3 months, 6 months, 9 months) stability studies. The test items are: protein concentration, appearance, visible particle, pH, purity (SEC-HPLC, non-reduced CE-SDS), charge variant, bioactivity. The design plan is shown in Table 23 below.

TABLE 23

Formulation design table for antibody A-1 at different concentrations

| Formulation | Protein concentration (mg/mL) | Sodium citrate (mM) | Arginine hydrochloride (mM) | Tween-80 (%) | pH |
| --- | --- | --- | --- | --- | --- |
| F11 | 26.1 | 20 | 140 | 0.04 | 5.8 |
| F12 | 53.9 | 20 | 140 | 0.04 | 5.8 |
| F13 | 103.1 | 20 | 140 | 0.04 | 5.8 |

Experimental Results

From appearance, as the protein concentration increased, the opalescence increased, and it's easier for the formulation samples to turn yellow at high concentration of the antibody (see Table 24). But after nine-month of long-term and acceleration stability test, the formulation sample was still clear and free of visible particles, meeting the requirement of injection. There was no significant change of the protein concentration and pH during the study (see Table 25 and Table 26).

The purity test result indicated, the SEC and CE-SDS purity of antibody A-1 decreased as the time passed and as the concentration increased. The CE-SDS purity of the samples decreased slightly more (see Table 27, Table 28 and Table 29). But after 9-month of stability test, the purity of the product still met the corresponding quality standards and, and the change of purity was within the acceptable range.

Figure 6:
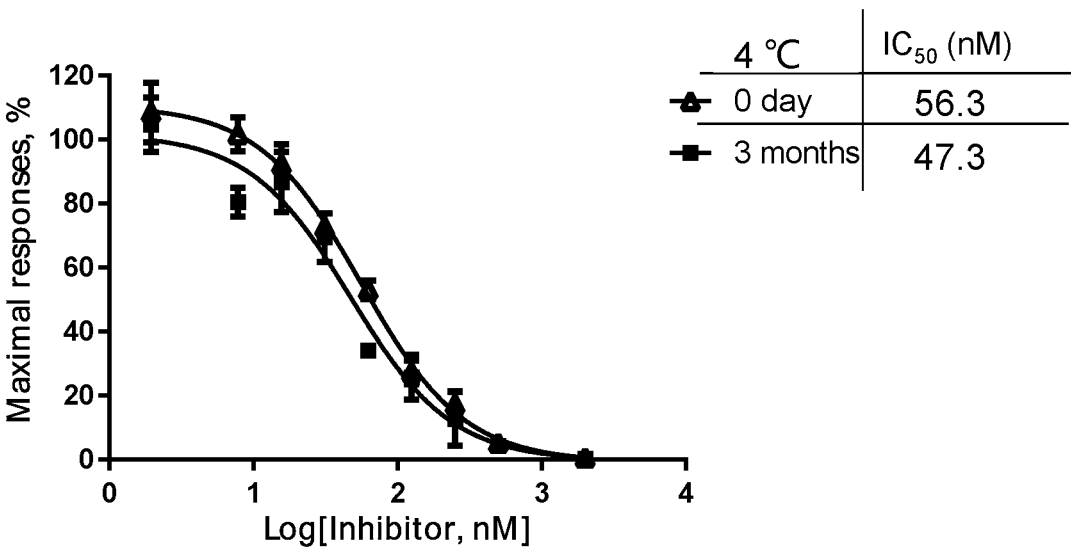
FIG. 6 shows that the biological activity of $ET_AR$ antibody A-1 (25 mg/mL) did not change significantly after 3 months of storage in a formulation solution containing 20 mM sodium citrate, 140 mM arginine-HCl, and 0.04% TWEEN-80 at pH 5.8 and 4° C.
Figure 7:
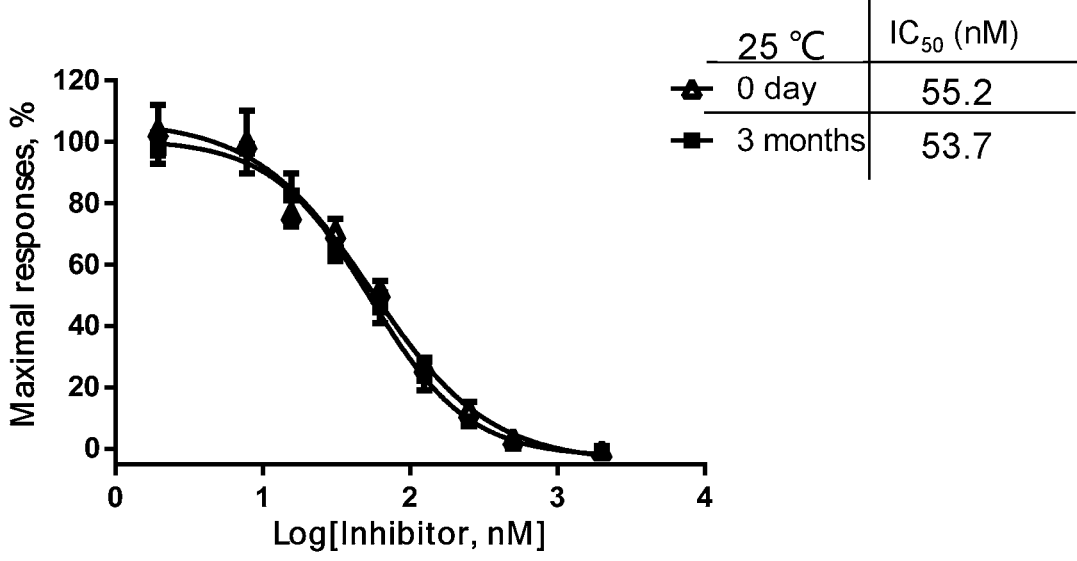
FIG. 7 shows that the biological activity of $ET_AR$ antibody A-1 (25 mg/mL) did not change significantly after 3 months of storage in a formulation solution containing 20 mM sodium citrate, 140 mM arginine-HCl, and 0.04% TWEEN-80 at pH 5.8 and 25° C.

The test result of charge variants indicated (see Table 30), the aggregates and acidic/basic charge variants increased as the protein concentration of antibody A-1 increased, and the stability at lower protein concentration is better. However, judging from the shape of the peaks, there is not much difference at the three concentrations, and the trend was consistent. Bioactivity test of the 3-month samples indicated the bioactivity was relatively stable, as shown in FIG. 6 and FIG. 7. Based on the above results, the protein is stable in this formulation for at least 18 months.

TABLE 24

| Appearance change of formulation samples during 0-9 months | | | | | | | |
| --- | --- | --- | --- | --- | --- | --- | --- |
| Formulation | Temp. | 0 day | 1 month | 2 months | 3 months | 6 months | 9 months |
| F11 | 4° C. | Clear | Clear | Clear | Clear | Slight opalescence | Slight opalescence |
| F12 | 4° C. | Clear | Clear | Slight opalescence | Slight opalescence | Slight opalescence | Slight opalescence |
| F13 | 4° C. | Slight yellow | Slight yellow | Opalescence | Slight yellow and opalescence | Slight yellow and opalescence | Slight yellow and opalescence |
| F11 | 25° C. | Clear | Clear | Clear | Clear | Slight opalescence | Slight opalescence |
| F12 | 25° C. | Clear | Clear | Slight opalescence | Slight opalescence | Slight opalescence | Slight opalescence |
| F13 | 25° C. | Slight yellow | Slight yellow | Opalescence | Slight yellow and opalescence | Slight yellow and opalescence | Slight yellow and opalescence |

TABLE 25

| Test results of protein concentrations (mg/mL) of formulation samples in long-term accelerated stability study | | | | | | | |
| --- | --- | --- | --- | --- | --- | --- | --- |
| Formulations | Temp. | 0 day | 1 month | 2 months | 3 months | 6 months | 9 months |
| F11 | 4° C. | 26.1 | 25.7 | 26.5 | 27.0 | 28.0 | 24.9 |
| F12 | 4° C. | 53.9 | 54.0 | 51.6 | 51.2 | 54.5 | 48.4 |
| F13 | 4° C. | 103.1 | 97.2 | 101.2 | 106.7 | 114.9 | 94.1 |
| F11 | 25° C. | 26.1 | 27.7 | 26.1 | 27.4 | 29.5 | 25.3 |
| F12 | 25° C. | 53.9 | 51.5 | 51.7 | 57.6 | 58.1 | 54.3 |
| F13 | 25° C. | 103.1 | 106.1 | 99.9 | 110.1 | 115.7 | 94.1 |

TABLE 26

| Test results of pH of formulation samples in a long-term accelerated stability study | | | | | | | |
| --- | --- | --- | --- | --- | --- | --- | --- |
| Formulations | Temp. | 0 day | 1 month | 2 months | 3 months | 6 months | 9 months |
| F11 | 4° C. | 5.89 | 5.86 | 5.88 | 5.87 | 5.86 | 5.84 |
| F12 | 4° C. | 5.89 | 5.86 | 5.86 | 5.84 | 5.86 | 5.83 |
| F13 | 4° C. | 5.91 | 5.87 | 5.88 | 5.83 | 5.87 | 5.86 |

TABLE 26-continued

| Test results of pH of formulation samples in a long-term accelerated stability study | | | | | | | |
| --- | --- | --- | --- | --- | --- | --- | --- |
| Formulations | Temp. | 0 day | 1 month | 2 months | 3 months | 6 months | 9 months |
| F11 | 25° C. | 5.89 | 5.85 | 5.87 | 5.96 | 5.83 | 5.84 |
| F12 | 25° C. | 5.89 | 5.86 | 5.86 | 5..83 | 5.88 | 5.86 |
| F13 | 25° C. | 5.91 | 5.86 | 5.88 | 5.84 | 5.89 | 5.87 |

TABLE 27

| Test results of SEC purity (%) of formulation samples in a long-term accelerated stability study | | | | | | | |
| --- | --- | --- | --- | --- | --- | --- | --- |
| Formulations | Temp. | 0 day | 1 month | 2 months | 3 months | 6 months | 9 months |
| F11 | 4° C. | 98.6 | 98.7 | 98.7 | 98.7 | 98.6 | 98.7 |
| F12 | 4° C. | 98.6 | 98.6 | 98.6 | 98.7 | 98.7 | 98.6 |
| F13 | 4° C. | 98.5 | 98.6 | 98.5 | 98.6 | 98.6 | 98.5 |
| F11 | 25° C. | 98.6 | 98.7 | 98.7 | 99.0 | 98.6 | 98.1 |

TABLE 27-continued

Test results of SEC purity (%) of formulation samples in a
long-term accelerated stability study

| Formulations | Temp. | 0 day | 1 month | 2 months | 3 months | 6 months | 9 months |
|---|---|---|---|---|---|---|---|
| F12 | 25° C. | 98.6 | 98.6 | 98.6 | 98.8 | 98.5 | 98.2 |
| F13 | 25° C. | 98.5 | 98.5 | 98.5 | 98.6 | 98.1 | 97.9 |

TABLE 28

Test results of the non-reduced CE-SDS purity (%) of formulation
samples in a long-term accelerated stability study

| Formulations | Temperature | 0 day | 1 month | 2 months | 3 months | 6 months | 9 months |
|---|---|---|---|---|---|---|---|
| F11 | 4° C. | 97.23 | 98.26 | 97.86 | 97.75 | 97.88 | 96.36 |
| F12 | 4° C. | 97.17 | 98.24 | 97.78 | 97.77 | 96.84 | 96.01 |
| F13 | 4° C. | 97.06 | 97.9 | 97.89 | 97.39 | 97.07 | 96.16 |
| F11 | 25° C. | 97.23 | 97.42 | 97.63 | 96.34 | 96.68 | 94.94 |
| F12 | 25° C. | 97.17 | 97.66 | 97.51 | 97.44 | 96.59 | 94.80 |
| F13 | 25° C. | 97.06 | 97.47 | 97.44 | 97.42 | 96.77 | 94.45 |

TABLE 29

Test results of reduced CE-SDS purity (%) of formulation
samples in a long-term accelerated stability study

| Formulations | Temperature | 3 months | 6 months | 9 months |
|---|---|---|---|---|
| F11 | 4° C. | 100 | 100 | 100 |
| F12 | 4° C. | 100 | 100 | 100 |
| F13 | 4° C. | 100 | 100 | 99.98 |
| F11 | 25° C. | 100 | 99.83 | 99.91 |
| F12 | 25° C. | 99.56 | 100 | 99.38 |
| F13 | 25° C. | 99.12 | 98.49 | 96.07 |

TABLE 30

Test results of the charge variant main peak (%) of formulation
samples in a long-term accelerated stability study

| Formulations | Temperature | 0 day | 1 month | 2 months | 3 months | 6 months | 9 months |
|---|---|---|---|---|---|---|---|
| F11 | 4° C. | 74.97 | 71.40 | 66.28 | 72.80 | 72.30 | 80.68 |
| F12 | 4° C. | 74.74 | 71.30 | 71.01 | 71.40 | 67.96 | 77.81 |
| F13 | 4° C. | 75.01 | 71.40 | 65.95 | 72.40 | 69.1 | 77.13 |
| F11 | 25° C. | 74.97 | 74.48 | 70.22 | 66.64 | 65.69 | 69.22 |
| F12 | 25° C. | 74.74 | 75.96 | 65.47 | 68.17 | 65.36 | 69.26 |
| F13 | 25° C. | 75.01 | 74.30 | 69.18 | 66.97 | 63.15 | 78.5 |

The formulation of antibody A-1 (20 mM sodium citrate, 140 mM arginine hydrochloride, 0.04% TWEEN-80, pH 5.8) was tested at 3 different antibody concentrations in long-term and accelerated stability studies. After 9 months, regardless of acceleration and long-term stability studies, the quality of the protein still met the quality standards set. Especially after 9 months of long-term storage, the purity of antibody A-1 remained above 98%.

The above embodiments are provided to fully disclose and explain how to make and use the claimed embodiments to one of ordinary skill in the art, and they are not meant to limit the scope of this disclosure. Modifications obvious to those skilled in the art are within the scope of the claims herein. All the publications, patents and patent applications cited in the specifications were incorporated herein as references, just as each of them was specifically and independently incorporated herein as a reference.

What is claimed is:

1. A stable pharmaceutical solution formulation of an $ET_4R$ antibody, comprising an $ET_4R$ antibody and a buffer, wherein the formulation has a pH approximately ranging from 5 to 7; and wherein the $ET_4R$ antibody comprises light chain CDR1 amino acid sequence: SEQ ID NO: 8; light chain CDR2 amino acid sequence: SEQ ID NO: 32; light chain CDR3 amino acid sequence: SEQ ID NO: 50; heavy chain CDR1 amino acid sequence: SEQ ID NO: 70; heavy chain CDR2 amino acid sequence: SEQ ID NO: 92; and heavy chain CDR3 amino acid sequence: SEQ ID NO: 116.

2. The formulation of claim 1, wherein the $ET_4R$ antibody comprises light chain variable domain amino acid sequence SEQ ID NO: 162 and heavy chain variable domain amino acid sequence SEQ ID NO: 190.

3. The formulation of claim 1, wherein the $ET_4R$ antibody comprises light chain variable domain amino acid sequence SEQ ID NO: 138 and heavy chain variable domain amino acid sequence SEQ ID NO: 166.

4. The formulation of claim 1, wherein the $ET_4R$ antibody further comprises light chain constant domain amino acid sequence SEQ ID NO: 194 or SEQ ID NO: 196; and heavy chain constant domain amino acid sequence SEQ ID NO: 198.

5. The formulation of claim 1, wherein the $ET_4R$ antibody comprises a murine $ET_4R$ antibody or a humanized $ET_4R$ antibody.

6. The formulation of claim 1, wherein the $ET_4R$ antibody comprises a monoclonal $ET_4R$ antibody.

7. The formulation of claim 1, wherein the concentration of the $ET_4R$ antibody is approximately ranging from 10 to 200 mg/mL or from 10 to 100 mg/mL.

8. The formulation of claim 1, wherein the concentration of the buffer is approximately ranging from 1 mM to 200 mM, from 2 mM to 50 mM, or from 5 mM to 25 mM.

9. The formulation of claim 1, wherein the buffer comprises a salt of citric acid or histidine.

10. The formulation of claim 1, further comprising a surfactant.

11. The formulation of claim 10, wherein the surfactant comprises a polysorbate.

12. The formulation of claim 11, wherein the surfactant comprises polysorbate 20 or polysorbate 80.

13. The formulation of claim 10, wherein the concentration of the surfactant is approximately ranging from 0.001 to 1 weight/volume percent, from 0.01 to 0.5 weight/volume percent, or from 0.01 to 0.1 weight/volume percent.

14. The formulation of claim 1, further comprising an amino acid protectant.

15. The formulation of claim 14, wherein the amino acid protectant comprises arginine or a salt thereof.

16. The formulation of claim 14, wherein the concentration of the amino acid protectant is approximately ranging from 1 mM to 500 mM or from 10 mM to 200 mM.

17. The formulation of claim 1, further comprising a polyol protectant.

18. The formulation of claim 17, wherein the concentration of the polyol protectant is approximately ranging from 0.1 to 50 weight/volume percent, from 1 to 20 weight/volume percent, or from 1 to 10 weight/volume percent.

19. The formulation of claim 1, further comprising a metal chelator.

20. The formulation of claim 19, wherein the concentration of the metal chelator is approximately ranging from 0.001 mM to 1 mM, from 0.005 mM to 0.5 mM, or from 0.01 mM to 0.2 mM.

21. A method of reducing pulmonary arterial hypertension in a subject, comprising administering to the subject a therapeutically effective amount of the formulation of claim 1.

* * * * *

SEQUENCE LISTING

```
Sequence total quantity: 204
SEQ ID NO: 1            moltype = DNA  length = 1868
FEATURE                 Location/Qualifiers
source                  1..1868
                        mol_type = other DNA
                        organism = Homo sapiens
SEQUENCE: 1
gaattcggga aaaagtgaag gtgtaaaagc agcacaagtg caataagaga tatttcctca   60
aatttgcctc aagatggaaa ccctttgcct cagggcatcc ttttggctgg cactggttgg  120
atgtgtaatc agtgataatc ctgagagata cagcacaaat ctaagcaatc atgtggatga  180
tttcaccact tttcgtggca cagagctcag cttcctggtt accactcatc aacccactaa  240
tttggtccta cccagcaatg gctcaatgca caactattgc ccacagcaga ctaaaattac  300
ttcagctttc aaatacatta acactgtgat atcttgtact attttcatcg tgggaatggt  360
ggggaatgca actctgctca ggatcattta ccagaacaaa tgtatgagga atggccccaa  420
cgcgctgata gccagtcttg cccttggaga ccttatctat gtggtcattg atctccctat  480
caatgtattt aagctgctgg ctgggcgctg gccttttgat cacaatgact ttggcgtatt  540
tctttgcaag ctgttcccct ttttgcagaa gtcctcggtg gggatcaccg tcctcaacct  600
ctgcgctctt agtgttgaca ggtacagagc agttgcctcc tggagtcgtg ttcagggaat  660
tgggattcct ttggtaactg ccattgaaat tgtctccatc tggatcctgt cctttatcct  720
ggccattcct gaagcgattg gcttcgtcat ggtacccttt gaatatagggg gtgaacagca  780
taaaacctgt atgctcaatg ccacatcaaa attcatggag ttctaccaag atgtaaagga  840
ctggtggctc ttcgggttct atttctgtat gcccttggtg tgcactgcga tcttctacac  900
cctcatgact tgtgagatgt tgaacagaag gaatggcagc ttgagaattg ccctcagtga  960
acatcttaag cagcgtcgag aagtggcaaa aacagttttc tgcttggttg taatttttgc  1020
tctttgctgg ttccctcttc atttaagccg tatattgaag aaaactgtgt ataacgagat 1080
ggacaagaac cgatgtgaat tacttagttt cttactgctc atggattaca tcggtattaa 1140
cttggcaacc atgaattcat gtataaaccc catagctgtg tattttgtga gcaagaaatt 1200
taaaaattgt ttccagtcat gcctctgctg ctgctgttac cagtccaaaa gtctgatgac 1260
ctcggtcccc atgaacggaa caagcatcca gtggaagaac cacgatcaaa acaaccacaa 1320
cacagaccgg agcagccata aggacagcat gaactgacca cccttagaag cactcctcgg 1380
tactcccata atcctctcgg agaaaaaaat cacaaggcaa ctgtgagtcc gggaatctct 1440
tctctgatcc ttcttcctta attcactccc acacccaaga agaaatgctt tccaaaaccg 1500
caagggtaga ctggtttatc cacccacaac atctacgaat cgtacttctt taattgatct 1560
aatttacata ttctgcgtgt tgtattcagc actaaaaaat ggtgggagct gggggagaat 1620
gaagactgtt aaatgaaacc agaaggatat ttactacttt tgcatgaaaa tagagctttc 1680
aagtacatgg ctagctttta tggcagttct ggtgaatgtt caatgggaac tggtcaccat 1740
gaaactttag agattaacga caagattttc tacttttttt aagtgatttt tttgtccttc 1800
agccaaacac aatatgggct caagtcactt ttatttgaaa tgtcatttgg tgccagtatc 1860
ccgaattc                                                        1868

SEQ ID NO: 2            moltype = AA  length = 427
FEATURE                 Location/Qualifiers
source                  1..427
                        mol_type = protein
                        organism = Homo sapiens
SEQUENCE: 2
METLCLRASF WLALVGCVIS DNPERYSTNL SNHVDDFTTF RGTELSFLVT THQPTNLVLP   60
SNGSMHNYCP QQTKITSAFK YINTVISCTI FIVGMVGNAT LLRIIYQNKC MRNGPNALIA  120
SLALGDLIYV VIDLPINVFK LLAGRWPFDH NDFGVFLCKL FPFLQKSSVG ITVLNLCALS  180
VDRYRAVASW SRVQGIGIPL VTAIEIVSIW ILSFILAIPE AIGFVMVPFE YRGEQHKTCM  240
LNATSKFMEF YQDVKDWWLF GFYFCMPLVC TAIFYTLMTC EMLNRRNGSL RIALSEHLKQ  300
RREVAKTVFC LVVIFALCWF PLHLSRILKK TVYNEMDKNR CELLSFLLLM DYIGINLATM  360
NSCINPIALY FVSKKFKNCF QSCLCCCYQ SKSLMTSVPM NGTSIQWKNH DQNNHNTDRS  420
SHKDSMN                                                          427

SEQ ID NO: 3            moltype = DNA  length = 2696
FEATURE                 Location/Qualifiers
```

-continued

```
source                  1..2696
                        mol_type = other DNA
                        organism = Mus musculus
SEQUENCE: 3
gtctaggagc ctgtggagtc taaggaagat cgcgggaggc gtgttcctcc ggagtttgct   60
tttccttggg agcctcgcgc gcacacccat cccttctagt ctggcaactg tgtctaggag   120
gtggggagcc tctctctgat ccaccggacc atcgctggag cttgcaggct gagcaagatc   180
tccccctaga gaagcctggc tgtccgggga agtttccccg agctgagact gtgctgcagc   240
cctggtcacc cgccaccctg cgcgccaccc tcgttctcca gctcaggctc cggctggccc   300
gtgcgcggac ctggagctgt ctgcttccga ggagctctaa ggtgaaaaaa agaaaggcgt   360
gagaccaaca taagaagact taaaatccag gttaagatga gtatcttttg ccttgcggca   420
tactttggc tgaccatggt gggaggcgta atggctgaca tccggagag atacagcgct   480
aatctaagca gccacatgga agacttcacc ccttttccgg ggacgggagt caactttctg   540
ggcaccaccc atcgaccccc taatttggcc ctgcctagca atggctcaat gcacggctat   600
tgcccacagc agactaaaat cacgacagct ttcaaatata ttaacactgt gatatcctgc   660
accattttca tcgtgggaat ggtggggaac gcaactctac tacgaatcat ttaccaaaac   720
aagtgtatga ggaacggccc caatgcgctc atagccagcc tggcccttgg agacctttatc   780
tacgtggtca ttgacctccc catcaacgtg tttaagctct tggcaggacg ctggccttc   840
gaccacaatg attttggagt gtttctctgc aagctgttcc ccttcctgca gaagtcctcc   900
gtgggcatca ccgtcttgaa cctctgtgct ctcagtgtgg acaggtacag agcagtggct   960
tcctggagcc gagttcaagg aatcgggatc cccttgatta ccgccattga aatcgtctcc   1020
atctggattc tttccttcat cttggccatc ccggaagcaa tcggcttcgt catggtaccc   1080
ttcgaataca agggcgagct gcataggacc tgcatgctca acgccacgtc caagttcatg   1140
gagtttacc aagatgtgaa ggactggtgg ctctttgggt tctacttctg catgcccttg   1200
gtgtgcacag caatcttcta caccctcatg acctgtgaga tgctcaacag gaggaacggc   1260
agcttgcgga tcgcccttag tgagcacctc aaacagcgtc gagaagtgca aaagactgtc   1320
ttctgcttgg ttgtcatctt cgccctgtgc tggttccctc ttcacttaag ccgcatttttg   1380
aagaaaactg tatatgatga gatggataag aaccggtgtg aactgctcag cttcttgctg   1440
ctaatggatt acatcggcat taacctggca accatgaatt cttgcataaa cccaatagct   1500
ctatattttg tgagcaagaa attcaaaaat tgttttcagt cctgcctctg ttgctgttgt   1560
caccagtccca aaagcctcat gacctcggtc cccatgaatg gaacgagtat ccagtggaag   1620
aaccaagagc agaacaacca caacacggaa cggagcagcc acaaggacag catgaactaa   1680
ccctccgcag aaacaccgag acgtgtgcct tcaagtccta ggatggaaac aaccattacg   1740
ccacagatgc gctcccaaaa cctcccaagt ctctcccatg ctccttttct aagtccatcc   1800
taggaaaagc tctcctgccc tcccaacagc acgtggtgga ccggtcccag ctatagccaa   1860
tgggtctttc ctgagtactg tatatgattt gcataccgcg catgtcattt ccaacacttg   1920
aaaattagac ctgggagaaa ggagatgatg gttcaaagaa gccacctagc tgccgccttt   1980
gcatgaacac agagtttgca agttcatgac cagcttccgt gcagttctat ggaccagctg   2040
gtgggaactg tccatcctaa gattctagag cagtgggtct caaccttccc aatgctgcag   2100
ccccttaata cagttcttca tttccagtg acccccccca accacaatat tatttttttgt   2160
tgctacttca attattttga attgttataa ttgtctgata tttctgatag tcttagcctg   2220
cccctgttaa agggtcatta gcaacccaca agttgagaac cactgcccta gaaattctgt   2280
tgcgtttcat ggcccatgac tacaatccta aaattggcag gatgagggaa gatggtcagg   2340
tgttcaaggt tagcctcatc aacatagttc ggaaaagcca gggctacctg ttctcacaag   2400
acacaaacag acaaaaagtg tttcaaagtt atggcagatt cattattatt aattattatt   2460
atcttatagc caaacacatt gtgaggttaa agtactcttt tggaaatgtc accgagtgtt   2520
ggtactttat aactgcatgg taccctagaa atgatcgttt catcttcttt caatgtactc   2580
tgaagaaaag aaataggaga gttccagaag ggagatctgg aaaggagata atgtttgaaa   2640
tgtaaagaag gaaaatatcc aataaaaaaa ttcaaagtct aaaaaaaaaa aaaaaa       2696

SEQ ID NO: 4          moltype = AA  length = 427
FEATURE               Location/Qualifiers
source                1..427
                      mol_type = protein
                      organism = Mus musculus
SEQUENCE: 4
MSIFCLAAYF WLTMVGGVMA DNPERYSANL SSHMEDFTPF PGTEINFLGT THRPPNLALP   60
SNGSMHGYCP QQTKITTAFK YINTVISCTI FIVGMVGNAT LLRIIYQNKC MRNGPNALIA   120
SLALGDLIYV VIDLPINVFK LLAGRWPFDH NDFGVFLCKL FPFLQKSSVG ITVLNLCALS   180
VDRYRAVASW SRVQGIGIPL ITAIEIVSIW ILSFILAIPE AIGFVMVPFE YKGELHRTCM   240
LNATSKFMEF YQDVKDWWLF GFYFCMPLVC TAIFYTLMTC EMLNRRNGSL RIALSEHLKQ   300
RREVAKTVFC LVVIFALCWF PLHLSRILKK TVYDEMDKNR CELLSFLLLM DYIGINLATM   360
NSCINPIALY FVSKKFKNCF QSCLCCCCHQ SKSLMTSVPM NGTSIQWKNQ EQNNHNTERS   420
SHKDSMN                                                             427

SEQ ID NO: 5          moltype = DNA  length = 1436
FEATURE               Location/Qualifiers
source                1..1436
                      mol_type = other DNA
                      organism = Rattus norvegicus
SEQUENCE: 5
gtgagaccaa cataacagga cgtttcttca gatccacatt aagatgggtg tcctttgctt   60
tctggcgtcc ttttggctgg ccctggtggg aggcgcaatc gctgacaatg ctgagagata   120
cagtgctaat ctaagcagcc acgtggagga cttcaccct tttccaggga cagagttcga   180
ctttctgggc accaccctc gaccccctaa tttggccctg cctagcaatg ctcaatgca   240
tggctattgc ccacagcaga caaaaatcac gacggctttc aaatatatca acactgtgat   300
atcctgtacc attttcatcg tgggaatggt ggggaacgcc actctcctaa gaatcattta   360
ccaaaacaag tgtatgagga acggccccaa tgcgctcata gccagcctgg cccttggaga   420
cctttatctac gtggtcattg atctccccat caatgtgttt aagctgttgg cggggcgctg   480
```

-continued

```
gccttttgac cacaatgatt ttggagtgtt tctctgcaag ctgttcccct ttttgcagaa   540
gtcgtccgtg ggcatcactg tcctgaatct ctgcgctctc agtgtggaca ggtacagagc   600
agtggcttcc tggagccggg ttcaaggaat cgggatcccc ttgattaccg ccattgaaat   660
tgtctccatc tggatccttt cctttatctt ggccatccca gaagcaatcg gcttcgtcat   720
ggtacccttc gaatacaagg gcgagcagca caggacctgc atgctcaacg ccacgaccaa   780
gttcatggag ttttaccaag acgtgaagga ctggtggctc tttggattct acttctgcat   840
gcccttggtg tgcacagcaa tcttctatac cctcatgacc tgtgagatgc tcaacagaag   900
gaatgggagc ttgcggattg ccctcagcga acacctcaag cagcgtcgag aggtggcaaa   960
gaccgtcttc tgcttggttg tcatcttcgc cctgtgctgg ttccctcttc acttaagccg  1020
aattttgaag aaaaccgtct atgatgagat ggataagaac cggtgtgaac tgctcagctt  1080
cttgctgctc atggattaca ttggcattaa cctggcaacc atgaactctt gcataaaccc  1140
aatagctctg tattttgtga gcaagaaatt caaaaattgt tttcagtcat gcctctgttg  1200
ctgttgtcac cagtccaaaa gcctcatgac ctcggtcccc atgaatggaa cgagtatcca  1260
gtggaagaac caggagcaga accacaacac agaacggaac agccacaagg acagcatgaa  1320
ctaaccctgt gcagaagcac cgagcagtgt gccttcgagt cccaggatga aacggtcacg  1380
cagcagctgc gctcccaaaa cctcccaggt ctctcccctg cttttttgtct aagctt      1436
```

```
SEQ ID NO: 6              moltype = AA  length = 426
FEATURE                   Location/Qualifiers
source                    1..426
                          mol_type = protein
                          organism = Rattus norvegicus
SEQUENCE: 6
MGVLCFLASF WLALVGGAIA DNAERYSANL SSHVEDFTPF PGTEFDFLGT TLRPPNLALP    60
SNGSMHGYCP QQTKITTAFK YINTVISCTI FIVGMVGNAT LLRIIYQNKC MRNGPNALIA   120
SLALGDLIYV VIDLPINVFK LLAGRWPFDH NDFGVFLCKL FPFLQKSSVG ITVLNLCALS   180
VDRYRAVASW SRVQGIGIPL ITAIEIVSIW ILSFILAIPE AIGFVMVPFE YKGEQHRTCM   240
LNATTKFMEF YQDVKDWWLF GFYFCMPLVC TAIFYTLMTC EMLNRRNGSL RIALSEHLKQ   300
RREVAKTVFC LVVIFALCWF PLHLSRILKK TVYDEMDKNR CELLSFLLLM DYIGINLATM   360
NSCINPIALY FVSKKFKNCF QSCLCCCCHQ SKSLMTSVPM NGTSIQWKNQ EQNHNTERSS   420
HKDSMN                                                             426
```

```
SEQ ID NO: 7              moltype = DNA  length = 33
FEATURE                   Location/Qualifiers
source                    1..33
                          mol_type = other DNA
                          organism = Mus musculus
SEQUENCE: 7
agggccagtc agaacattgg cacaagcata cac                                33
```

```
SEQ ID NO: 8              moltype = AA  length = 11
FEATURE                   Location/Qualifiers
source                    1..11
                          mol_type = protein
                          organism = Mus musculus
SEQUENCE: 8
RASQNIGTSI H                                                        11
```

```
SEQ ID NO: 9              moltype = DNA  length = 33
FEATURE                   Location/Qualifiers
source                    1..33
                          mol_type = other DNA
                          organism = Mus musculus
SEQUENCE: 9
cgagcaagtg aaaatattta cagttattta gca                                33
```

```
SEQ ID NO: 10             moltype = AA  length = 11
FEATURE                   Location/Qualifiers
source                    1..11
                          mol_type = protein
                          organism = Mus musculus
SEQUENCE: 10
RASENIYSYL A                                                        11
```

```
SEQ ID NO: 11             moltype = DNA  length = 39
FEATURE                   Location/Qualifiers
source                    1..39
                          mol_type = other DNA
                          organism = Mus musculus
SEQUENCE: 11
cagagcctct ttgatattga tggaaagaca tatttgaat                          39
```

```
SEQ ID NO: 12             moltype = AA  length = 13
FEATURE                   Location/Qualifiers
source                    1..13
                          mol_type = protein
                          organism = Mus musculus
SEQUENCE: 12
QSLFDIDGKT YLN                                                      13
```

```
SEQ ID NO: 13              moltype = DNA  length = 33
FEATURE                    Location/Qualifiers
source                     1..33
                           mol_type = other DNA
                           organism = Mus musculus
SEQUENCE: 13
cgggcaagtc aggacattgg tggtagctta aac                                    33

SEQ ID NO: 14              moltype = AA  length = 11
FEATURE                    Location/Qualifiers
source                     1..11
                           mol_type = protein
                           organism = Mus musculus
SEQUENCE: 14
RASQDIGGSL N                                                            11

SEQ ID NO: 15              moltype = DNA  length = 33
FEATURE                    Location/Qualifiers
source                     1..33
                           mol_type = other DNA
                           organism = Mus musculus
SEQUENCE: 15
agggccagcc agactattag cgacttctta cac                                    33

SEQ ID NO: 16              moltype = AA  length = 11
FEATURE                    Location/Qualifiers
source                     1..11
                           mol_type = protein
                           organism = Mus musculus
SEQUENCE: 16
RASQTISDFL H                                                            11

SEQ ID NO: 17              moltype = DNA  length = 33
FEATURE                    Location/Qualifiers
source                     1..33
                           mol_type = other DNA
                           organism = Mus musculus
SEQUENCE: 17
agggcaagtg aggacataca cactcaatta gcc                                    33

SEQ ID NO: 18              moltype = AA  length = 11
FEATURE                    Location/Qualifiers
source                     1..11
                           mol_type = protein
                           organism = Mus musculus
SEQUENCE: 18
RASEDIHTQL A                                                            11

SEQ ID NO: 19              moltype = DNA  length = 48
FEATURE                    Location/Qualifiers
source                     1..48
                           mol_type = other DNA
                           organism = Mus musculus
SEQUENCE: 19
agatctagtc agtacattgt tcatagtact ggaaccacct atttagaa                    48

SEQ ID NO: 20              moltype = AA  length = 16
FEATURE                    Location/Qualifiers
source                     1..16
                           mol_type = protein
                           organism = Mus musculus
SEQUENCE: 20
RSSQYIVHST GTTYLE                                                       16

SEQ ID NO: 21              moltype = DNA  length = 48
FEATURE                    Location/Qualifiers
source                     1..48
                           mol_type = other DNA
                           organism = Mus musculus
SEQUENCE: 21
agatctagtc attaccttgt tcatgataac ggaaacacct atgttgaa                    48

SEQ ID NO: 22              moltype = AA  length = 16
FEATURE                    Location/Qualifiers
source                     1..16
                           mol_type = protein
                           organism = Mus musculus
SEQUENCE: 22
```

-continued

```
RSSHYLVHDN GNTYVE                                                16

SEQ ID NO: 23           moltype = DNA   length = 48
FEATURE                 Location/Qualifiers
source                  1..48
                        mol_type = other DNA
                        organism = Mus musculus
SEQUENCE: 23
agatctagtc agaacattgt ccatagtact ggaaacacct atttagaa            48

SEQ ID NO: 24           moltype = AA   length = 16
FEATURE                 Location/Qualifiers
source                  1..16
                        mol_type = protein
                        organism = Mus musculus
SEQUENCE: 24
RSSQNIVHST GNTYLE                                                16

SEQ ID NO: 25           moltype = DNA   length = 30
FEATURE                 Location/Qualifiers
source                  1..30
                        mol_type = other DNA
                        organism = Mus musculus
SEQUENCE: 25
agtgtcagct caagtgtaag ttacatacac                                30

SEQ ID NO: 26           moltype = AA   length = 10
FEATURE                 Location/Qualifiers
source                  1..10
                        mol_type = protein
                        organism = Mus musculus
SEQUENCE: 26
SVSSSVSYIH                                                       10

SEQ ID NO: 27           moltype = DNA   length = 30
FEATURE                 Location/Qualifiers
source                  1..30
                        mol_type = other DNA
                        organism = Mus musculus
SEQUENCE: 27
agtgccagct caagtgtaag ttacatgtgc                                30

SEQ ID NO: 28           moltype = AA   length = 10
FEATURE                 Location/Qualifiers
source                  1..10
                        mol_type = protein
                        organism = Mus musculus
SEQUENCE: 28
SASSSVSYMC                                                       10

SEQ ID NO: 29           moltype = DNA   length = 18
FEATURE                 Location/Qualifiers
source                  1..18
                        mol_type = other DNA
                        organism = Mus musculus
SEQUENCE: 29
cagggcatta acaattat                                              18

SEQ ID NO: 30           moltype = AA   length = 6
FEATURE                 Location/Qualifiers
source                  1..6
                        mol_type = protein
                        organism = Mus musculus
SEQUENCE: 30
QGINNY                                                           6

SEQ ID NO: 31           moltype = DNA   length = 21
FEATURE                 Location/Qualifiers
source                  1..21
                        mol_type = other DNA
                        organism = Mus musculus
SEQUENCE: 31
tatgcttcta agtctatatc t                                         21

SEQ ID NO: 32           moltype = AA   length = 7
FEATURE                 Location/Qualifiers
source                  1..7
                        mol_type = protein
                        organism = Mus musculus
```

```
SEQUENCE: 32
YASKSIS                                                                  7

SEQ ID NO: 33          moltype = DNA   length = 21
FEATURE                Location/Qualifiers
source                 1..21
                       mol_type = other DNA
                       organism = Mus musculus
SEQUENCE: 33
aatgcaaaaa ccttagcaga a                                                 21

SEQ ID NO: 34          moltype = AA   length = 7
FEATURE                Location/Qualifiers
source                 1..7
                       mol_type = protein
                       organism = Mus musculus
SEQUENCE: 34
NAKTLAE                                                                   7

SEQ ID NO: 35          moltype = DNA   length = 21
FEATURE                Location/Qualifiers
source                 1..21
                       mol_type = other DNA
                       organism = Mus musculus
SEQUENCE: 35
ctggtgtctg aattggactc t                                                 21

SEQ ID NO: 36          moltype = AA   length = 7
FEATURE                Location/Qualifiers
source                 1..7
                       mol_type = protein
                       organism = Mus musculus
SEQUENCE: 36
LVSELDS                                                                   7

SEQ ID NO: 37          moltype = DNA   length = 21
FEATURE                Location/Qualifiers
source                 1..21
                       mol_type = other DNA
                       organism = Mus musculus
SEQUENCE: 37
gccacatcca gcttagattc t                                                 21

SEQ ID NO: 38          moltype = AA   length = 7
FEATURE                Location/Qualifiers
source                 1..7
                       mol_type = protein
                       organism = Mus musculus
SEQUENCE: 38
ATSSLDS                                                                   7

SEQ ID NO: 39          moltype = DNA   length = 21
FEATURE                Location/Qualifiers
source                 1..21
                       mol_type = other DNA
                       organism = Mus musculus
SEQUENCE: 39
tatgcttccc aatccatctc t                                                 21

SEQ ID NO: 40          moltype = AA   length = 7
FEATURE                Location/Qualifiers
source                 1..7
                       mol_type = protein
                       organism = Mus musculus
SEQUENCE: 40
YASQSIS                                                                   7

SEQ ID NO: 41          moltype = DNA   length = 21
FEATURE                Location/Qualifiers
source                 1..21
                       mol_type = other DNA
                       organism = Mus musculus
SEQUENCE: 41
ggtgcagcca gtttgaaaag t                                                 21

SEQ ID NO: 42          moltype = AA   length = 7
FEATURE                Location/Qualifiers
source                 1..7
                       mol_type = protein
```

-continued

```
                            organism = Mus musculus
SEQUENCE: 42
GAASLKS                                                        7

SEQ ID NO: 43          moltype = DNA   length = 21
FEATURE                Location/Qualifiers
source                 1..21
                       mol_type = other DNA
                       organism = Mus musculus
SEQUENCE: 43
aaagtttcca accgattttc t                                        21

SEQ ID NO: 44          moltype = AA   length = 7
FEATURE                Location/Qualifiers
source                 1..7
                       mol_type = protein
                       organism = Mus musculus
SEQUENCE: 44
KVSNRFS                                                        7

SEQ ID NO: 45          moltype = DNA   length = 21
FEATURE                Location/Qualifiers
source                 1..21
                       mol_type = other DNA
                       organism = Mus musculus
SEQUENCE: 45
gacacatcca aactggcttc t                                        21

SEQ ID NO: 46          moltype = AA   length = 7
FEATURE                Location/Qualifiers
source                 1..7
                       mol_type = protein
                       organism = Mus musculus
SEQUENCE: 46
DTSKLAS                                                        7

SEQ ID NO: 47          moltype = DNA   length = 21
FEATURE                Location/Qualifiers
source                 1..21
                       mol_type = other DNA
                       organism = Mus musculus
SEQUENCE: 47
tatacatcaa ctttacagtc a                                        21

SEQ ID NO: 48          moltype = AA   length = 7
FEATURE                Location/Qualifiers
source                 1..7
                       mol_type = protein
                       organism = Mus musculus
SEQUENCE: 48
YTSTLQS                                                        7

SEQ ID NO: 49          moltype = DNA   length = 27
FEATURE                Location/Qualifiers
source                 1..27
                       mol_type = other DNA
                       organism = Mus musculus
SEQUENCE: 49
caacatagtt atagcttccc gtggacg                                  27

SEQ ID NO: 50          moltype = AA   length = 9
FEATURE                Location/Qualifiers
source                 1..9
                       mol_type = protein
                       organism = Mus musculus
SEQUENCE: 50
QHSYSFPWT                                                      9

SEQ ID NO: 51          moltype = DNA   length = 27
FEATURE                Location/Qualifiers
source                 1..27
                       mol_type = other DNA
                       organism = Mus musculus
SEQUENCE: 51
cagcatcatt atggtattcc gttcacg                                  27

SEQ ID NO: 52          moltype = AA   length = 9
FEATURE                Location/Qualifiers
source                 1..9
```

```
                             mol_type = protein
                             organism = Mus musculus
SEQUENCE: 52
QHHYGIPFT                                                              9

SEQ ID NO: 53          moltype = DNA   length = 27
FEATURE                Location/Qualifiers
source                 1..27
                       mol_type = other DNA
                       organism = Mus musculus
SEQUENCE: 53
tggcaaggta cacattttcc gctcacg                                         27

SEQ ID NO: 54          moltype = AA   length = 9
FEATURE                Location/Qualifiers
source                 1..9
                       mol_type = protein
                       organism = Mus musculus
SEQUENCE: 54
WQGTHFPLT                                                              9

SEQ ID NO: 55          moltype = DNA   length = 27
FEATURE                Location/Qualifiers
source                 1..27
                       mol_type = other DNA
                       organism = Mus musculus
SEQUENCE: 55
ctacaatatg ctagttctcc gtatacg                                         27

SEQ ID NO: 56          moltype = AA   length = 9
FEATURE                Location/Qualifiers
source                 1..9
                       mol_type = protein
                       organism = Mus musculus
SEQUENCE: 56
LQYASSPYT                                                              9

SEQ ID NO: 57          moltype = DNA   length = 27
FEATURE                Location/Qualifiers
source                 1..27
                       mol_type = other DNA
                       organism = Mus musculus
SEQUENCE: 57
caaagtggta acacctttcc gtggacg                                         27

SEQ ID NO: 58          moltype = AA   length = 9
FEATURE                Location/Qualifiers
source                 1..9
                       mol_type = protein
                       organism = Mus musculus
SEQUENCE: 58
QSGNTFPWT                                                              9

SEQ ID NO: 59          moltype = DNA   length = 27
FEATURE                Location/Qualifiers
source                 1..27
                       mol_type = other DNA
                       organism = Mus musculus
SEQUENCE: 59
caacagtata ggagtattcc gtggacg                                         27

SEQ ID NO: 60          moltype = AA   length = 9
FEATURE                Location/Qualifiers
source                 1..9
                       mol_type = protein
                       organism = Mus musculus
SEQUENCE: 60
QQYRSIPWT                                                              9

SEQ ID NO: 61          moltype = DNA   length = 27
FEATURE                Location/Qualifiers
source                 1..27
                       mol_type = other DNA
                       organism = Mus musculus
SEQUENCE: 61
tttcaaggtt cacattttcc attcacg                                         27

SEQ ID NO: 62          moltype = AA   length = 9
FEATURE                Location/Qualifiers
```

-continued

```
source                  1..9
                        mol_type = protein
                        organism = Mus musculus
SEQUENCE: 62
FQGSHFPFT                                                              9

SEQ ID NO: 63           moltype = DNA   length = 27
FEATURE                 Location/Qualifiers
source                  1..27
                        mol_type = other DNA
                        organism = Mus musculus
SEQUENCE: 63
tttcaaggtt cacatttccc attcacg                                          27

SEQ ID NO: 64           moltype = AA   length = 9
FEATURE                 Location/Qualifiers
source                  1..9
                        mol_type = protein
                        organism = Mus musculus
SEQUENCE: 64
HQWSTNPPT                                                              9

SEQ ID NO: 65           moltype = DNA   length = 27
FEATURE                 Location/Qualifiers
source                  1..27
                        mol_type = other DNA
                        organism = Mus musculus
SEQUENCE: 65
cagcagtgga gtagtaaccc acccacg                                          27

SEQ ID NO: 66           moltype = AA   length = 9
FEATURE                 Location/Qualifiers
source                  1..9
                        mol_type = protein
                        organism = Mus musculus
SEQUENCE: 66
QQWSSNPPT                                                              9

SEQ ID NO: 67           moltype = DNA   length = 24
FEATURE                 Location/Qualifiers
source                  1..24
                        mol_type = other DNA
                        organism = Mus musculus
SEQUENCE: 67
cagcagttta gtaaacttcg gaca                                             24

SEQ ID NO: 68           moltype = AA   length = 8
FEATURE                 Location/Qualifiers
source                  1..8
                        mol_type = protein
                        organism = Mus musculus
SEQUENCE: 68
QQFSKLRT                                                               8

SEQ ID NO: 69           moltype = DNA   length = 36
FEATURE                 Location/Qualifiers
source                  1..36
                        mol_type = other DNA
                        organism = Mus musculus
SEQUENCE: 69
gggttctcac tgaccacttc tggcttgggt gttgcc                                36

SEQ ID NO: 70           moltype = AA   length = 12
FEATURE                 Location/Qualifiers
source                  1..12
                        mol_type = protein
                        organism = Mus musculus
SEQUENCE: 70
GFSLTTSGLG VA                                                          12

SEQ ID NO: 71           moltype = DNA   length = 30
FEATURE                 Location/Qualifiers
source                  1..30
                        mol_type = other DNA
                        organism = Mus musculus
SEQUENCE: 71
ggctacacct ttactagcta ctggatacac                                       30

SEQ ID NO: 72           moltype = AA   length = 10
```

-continued

```
FEATURE              Location/Qualifiers
source               1..10
                     mol_type = protein
                     organism = Mus musculus
SEQUENCE: 72
GYTFTSYWIH                                                          10

SEQ ID NO: 73        moltype = DNA   length = 30
FEATURE              Location/Qualifiers
source               1..30
                     mol_type = other DNA
                     organism = Mus musculus
SEQUENCE: 73
ggcctcaaca ttaaagacat ctatattcac                                   30

SEQ ID NO: 74        moltype = AA   length = 10
FEATURE              Location/Qualifiers
source               1..10
                     mol_type = protein
                     organism = Mus musculus
SEQUENCE: 74
GLNIKDIYIH                                                          10

SEQ ID NO: 75        moltype = DNA   length = 30
FEATURE              Location/Qualifiers
source               1..30
                     mol_type = other DNA
                     organism = Mus musculus
SEQUENCE: 75
ggttactcat tcaccaacta ctggatacac                                   30

SEQ ID NO: 76        moltype = AA   length = 10
FEATURE              Location/Qualifiers
source               1..10
                     mol_type = protein
                     organism = Mus musculus
SEQUENCE: 76
GYSFTNYWIH                                                          10

SEQ ID NO: 77        moltype = DNA   length = 30
FEATURE              Location/Qualifiers
source               1..30
                     mol_type = other DNA
                     organism = Mus musculus
SEQUENCE: 77
ggattcactt tcagtgacta tcccatgtct                                   30

SEQ ID NO: 78        moltype = AA   length = 10
FEATURE              Location/Qualifiers
source               1..10
                     mol_type = protein
                     organism = Mus musculus
SEQUENCE: 78
GFTFSDYPMS                                                          10

SEQ ID NO: 79        moltype = DNA   length = 30
FEATURE              Location/Qualifiers
source               1..30
                     mol_type = other DNA
                     organism = Mus musculus
SEQUENCE: 79
ggattcactt tcagtagctt tggcatgtct                                   30

SEQ ID NO: 80        moltype = AA   length = 10
FEATURE              Location/Qualifiers
source               1..10
                     mol_type = protein
                     organism = Mus musculus
SEQUENCE: 80
GFTFSSFGMS                                                          10

SEQ ID NO: 81        moltype = DNA   length = 30
FEATURE              Location/Qualifiers
source               1..30
                     mol_type = other DNA
                     organism = Mus musculus
SEQUENCE: 81
ggattcactt tcagtaccta tggcatgtct                                   30
```

```
SEQ ID NO: 82              moltype = AA   length = 10
FEATURE                    Location/Qualifiers
source                     1..10
                           mol_type = protein
                           organism = Mus musculus
SEQUENCE: 82
GFTFSTYGMS                                                              10

SEQ ID NO: 83              moltype = DNA   length = 30
FEATURE                    Location/Qualifiers
source                     1..30
                           mol_type = other DNA
                           organism = Mus musculus
SEQUENCE: 83
ggattcactt tcagtagtta tggcatgtct                                        30

SEQ ID NO: 84              moltype = AA   length = 10
FEATURE                    Location/Qualifiers
source                     1..10
                           mol_type = protein
                           organism = Mus musculus
SEQUENCE: 84
GFTFSSYGMS                                                              10

SEQ ID NO: 85              moltype = DNA   length = 36
FEATURE                    Location/Qualifiers
source                     1..36
                           mol_type = other DNA
                           organism = Mus musculus
SEQUENCE: 85
gggttttcac tgaccacttc tggtatgggt gtaggc                                 36

SEQ ID NO: 86              moltype = AA   length = 12
FEATURE                    Location/Qualifiers
source                     1..12
                           mol_type = protein
                           organism = Mus musculus
SEQUENCE: 86
GFSLTTSGMG VG                                                           12

SEQ ID NO: 87              moltype = DNA   length = 36
FEATURE                    Location/Qualifiers
source                     1..36
                           mol_type = other DNA
                           organism = Mus musculus
SEQUENCE: 87
ggattttcac tgagcacttc tggtttgggt gtaggc                                 36

SEQ ID NO: 88              moltype = AA   length = 12
FEATURE                    Location/Qualifiers
source                     1..12
                           mol_type = protein
                           organism = Mus musculus
SEQUENCE: 88
GFSLSTSGLG VG                                                           12

SEQ ID NO: 89              moltype = DNA   length = 24
FEATURE                    Location/Qualifiers
source                     1..24
                           mol_type = other DNA
                           organism = Mus musculus
SEQUENCE: 89
ggattcacct tcagtgatta ttac                                              24

SEQ ID NO: 90              moltype = AA   length = 8
FEATURE                    Location/Qualifiers
source                     1..8
                           mol_type = protein
                           organism = Mus musculus
SEQUENCE: 90
GFTFSDYY                                                                8

SEQ ID NO: 91              moltype = DNA   length = 48
FEATURE                    Location/Qualifiers
source                     1..48
                           mol_type = other DNA
                           organism = Mus musculus
SEQUENCE: 91
cacatttggt cggatggtga cacgcgctat tacccagccc tgaagaac                    48
```

-continued

```
SEQ ID NO: 92              moltype = AA   length = 16
FEATURE                    Location/Qualifiers
source                     1..16
                           mol_type = protein
                           organism = Mus musculus
SEQUENCE: 92
HIWSDGDTRY YPALKN                                                    16

SEQ ID NO: 93              moltype = DNA   length = 36
FEATURE                    Location/Qualifiers
source                     1..36
                           mol_type = other DNA
                           organism = Mus musculus
SEQUENCE: 93
tacattaatc ctgacactga ttatagtgag tacaat                             36

SEQ ID NO: 94              moltype = AA   length = 12
FEATURE                    Location/Qualifiers
source                     1..12
                           mol_type = protein
                           organism = Mus musculus
SEQUENCE: 94
YINPDTDYSE YN                                                       12

SEQ ID NO: 95              moltype = DNA   length = 36
FEATURE                    Location/Qualifiers
source                     1..36
                           mol_type = other DNA
                           organism = Mus musculus
SEQUENCE: 95
aggattgatc ctgcgaacgg taagactgca tatgac                             36

SEQ ID NO: 96              moltype = AA   length = 12
FEATURE                    Location/Qualifiers
source                     1..12
                           mol_type = protein
                           organism = Mus musculus
SEQUENCE: 96
RIDPANGKTA YD                                                       12

SEQ ID NO: 97              moltype = DNA   length = 36
FEATURE                    Location/Qualifiers
source                     1..36
                           mol_type = other DNA
                           organism = Mus musculus
SEQUENCE: 97
atgattgatc cttccgatgc tgaaactggg ttaaat                             36

SEQ ID NO: 98              moltype = AA   length = 12
FEATURE                    Location/Qualifiers
source                     1..12
                           mol_type = protein
                           organism = Mus musculus
SEQUENCE: 98
MIDPSDAETG LN                                                       12

SEQ ID NO: 99              moltype = DNA   length = 24
FEATURE                    Location/Qualifiers
source                     1..24
                           mol_type = other DNA
                           organism = Mus musculus
SEQUENCE: 99
gttagtgatg gtggtggttc cacc                                          24

SEQ ID NO: 100             moltype = AA   length = 8
FEATURE                    Location/Qualifiers
source                     1..8
                           mol_type = protein
                           organism = Mus musculus
SEQUENCE: 100
VSDGGGST                                                            8

SEQ ID NO: 101             moltype = DNA   length = 24
FEATURE                    Location/Qualifiers
source                     1..24
                           mol_type = other DNA
                           organism = Mus musculus
SEQUENCE: 101
```

-continued

```
attagtagtg ctggtagttt cacc                                          24

SEQ ID NO: 102          moltype = AA  length = 8
FEATURE                 Location/Qualifiers
source                  1..8
                        mol_type = protein
                        organism = Mus musculus
SEQUENCE: 102
ISSAGSFT                                                            8

SEQ ID NO: 103          moltype = DNA  length = 51
FEATURE                 Location/Qualifiers
source                  1..51
                        mol_type = other DNA
                        organism = Mus musculus
SEQUENCE: 103
accattaata ctaatggtgg taccacctat tatcgagaca gtgtgaaggg c           51

SEQ ID NO: 104          moltype = AA  length = 17
FEATURE                 Location/Qualifiers
source                  1..17
                        mol_type = protein
                        organism = Mus musculus
SEQUENCE: 104
TINTNGGTTY YRDSVKG                                                  17

SEQ ID NO: 105          moltype = DNA  length = 51
FEATURE                 Location/Qualifiers
source                  1..51
                        mol_type = other DNA
                        organism = Mus musculus
SEQUENCE: 105
accataaata ctaatggtgg taacacctat tattcagaca atgtgaaggg c           51

SEQ ID NO: 106          moltype = AA  length = 17
FEATURE                 Location/Qualifiers
source                  1..17
                        mol_type = protein
                        organism = Mus musculus
SEQUENCE: 106
TINTNGGNTY YSDNVKG                                                  17

SEQ ID NO: 107          moltype = DNA  length = 51
FEATURE                 Location/Qualifiers
source                  1..51
                        mol_type = other DNA
                        organism = Mus musculus
SEQUENCE: 107
accattagta ctaatggtgc caccgccaat tatccagaca gtgtgaaggg c           51

SEQ ID NO: 108          moltype = AA  length = 17
FEATURE                 Location/Qualifiers
source                  1..17
                        mol_type = protein
                        organism = Mus musculus
SEQUENCE: 108
TISTNGATAN YPDSVKG                                                  17

SEQ ID NO: 109          moltype = DNA  length = 48
FEATURE                 Location/Qualifiers
source                  1..48
                        mol_type = other DNA
                        organism = Mus musculus
SEQUENCE: 109
cacatttggt gggatgatga taagtactat aatccatccc tgaagagc               48

SEQ ID NO: 110          moltype = AA  length = 16
FEATURE                 Location/Qualifiers
source                  1..16
                        mol_type = protein
                        organism = Mus musculus
SEQUENCE: 110
HIWWDDDKYY NPSLKS                                                   16

SEQ ID NO: 111          moltype = DNA  length = 48
FEATURE                 Location/Qualifiers
source                  1..48
                        mol_type = other DNA
                        organism = Mus musculus
```

-continued

```
SEQUENCE: 111
cacatttggt gggatgatga taagtactat aatccatccc ttaagaga                    48

SEQ ID NO: 112        moltype = AA  length = 16
FEATURE               Location/Qualifiers
source                1..16
                      mol_type = protein
                      organism = Mus musculus
SEQUENCE: 112
HIWWDDDKYY NPSLKR                                                        16

SEQ ID NO: 113        moltype = DNA  length = 30
FEATURE               Location/Qualifiers
source                1..30
                      mol_type = other DNA
                      organism = Mus musculus
SEQUENCE: 113
attagaaatc gggctaatgg ttacacaaca                                        30

SEQ ID NO: 114        moltype = AA  length = 10
FEATURE               Location/Qualifiers
source                1..10
                      mol_type = protein
                      organism = Mus musculus
SEQUENCE: 114
IRNRANGYTT                                                              10

SEQ ID NO: 115        moltype = DNA  length = 30
FEATURE               Location/Qualifiers
source                1..30
                      mol_type = other DNA
                      organism = Mus musculus
SEQUENCE: 115
atgaaggatg atagtcttta ctttgacaac                                        30

SEQ ID NO: 116        moltype = AA  length = 10
FEATURE               Location/Qualifiers
source                1..10
                      mol_type = protein
                      organism = Mus musculus
SEQUENCE: 116
MKDDSLYFDN                                                              10

SEQ ID NO: 117        moltype = DNA  length = 30
FEATURE               Location/Qualifiers
source                1..30
                      mol_type = other DNA
                      organism = Mus musculus
SEQUENCE: 117
gcaagtgctg gttattattt ttttgacttc                                        30

SEQ ID NO: 118        moltype = AA  length = 10
FEATURE               Location/Qualifiers
source                1..10
                      mol_type = protein
                      organism = Mus musculus
SEQUENCE: 118
ASAGYYFFDF                                                              10

SEQ ID NO: 119        moltype = DNA  length = 15
FEATURE               Location/Qualifiers
source                1..15
                      mol_type = other DNA
                      organism = Mus musculus
SEQUENCE: 119
ggtaggggggg cccac                                                       15

SEQ ID NO: 120        moltype = AA  length = 5
FEATURE               Location/Qualifiers
source                1..5
                      mol_type = protein
                      organism = Mus musculus
SEQUENCE: 120
GRGAH                                                                    5

SEQ ID NO: 121        moltype = DNA  length = 33
FEATURE               Location/Qualifiers
source                1..33
                      mol_type = other DNA
```

```
                          organism = Mus musculus
SEQUENCE: 121
gcaagaattg gcgattacta taatatggac tac                                    33

SEQ ID NO: 122           moltype = AA   length = 11
FEATURE                  Location/Qualifiers
source                   1..11
                         mol_type = protein
                         organism = Mus musculus
SEQUENCE: 122
ARIGDYYNMD Y                                                            11

SEQ ID NO: 123           moltype = DNA   length = 45
FEATURE                  Location/Qualifiers
source                   1..45
                         mol_type = other DNA
                         organism = Mus musculus
SEQUENCE: 123
acaagacatg cttcctacta tagctacgac cattctatgg actac                      45

SEQ ID NO: 124           moltype = AA   length = 15
FEATURE                  Location/Qualifiers
source                   1..15
                         mol_type = protein
                         organism = Mus musculus
SEQUENCE: 124
TRHASYYSYD HSMDY                                                        15

SEQ ID NO: 125           moltype = DNA   length = 36
FEATURE                  Location/Qualifiers
source                   1..36
                         mol_type = other DNA
                         organism = Mus musculus
SEQUENCE: 125
gcaagacggg ggtacgacgt tgggtgcttt gaccac                                36

SEQ ID NO: 126           moltype = AA   length = 12
FEATURE                  Location/Qualifiers
source                   1..12
                         mol_type = protein
                         organism = Mus musculus
SEQUENCE: 126
ARRGYDVGCF DH                                                          12

SEQ ID NO: 127           moltype = DNA   length = 27
FEATURE                  Location/Qualifiers
source                   1..27
                         mol_type = other DNA
                         organism = Mus musculus
SEQUENCE: 127
gcaagagact acgggctat ggactac                                           27

SEQ ID NO: 128           moltype = AA   length = 9
FEATURE                  Location/Qualifiers
source                   1..9
                         mol_type = protein
                         organism = Mus musculus
SEQUENCE: 128
ARDYGAMDY                                                               9

SEQ ID NO: 129           moltype = DNA   length = 27
FEATURE                  Location/Qualifiers
source                   1..27
                         mol_type = other DNA
                         organism = Mus musculus
SEQUENCE: 129
gcaactgaaa agggagctat gggctac                                          27

SEQ ID NO: 130           moltype = AA   length = 9
FEATURE                  Location/Qualifiers
source                   1..9
                         mol_type = protein
                         organism = Mus musculus
SEQUENCE: 130
ATEKGAMGY                                                               9

SEQ ID NO: 131           moltype = DNA   length = 57
FEATURE                  Location/Qualifiers
source                   1..57
```

-continued

```
                         mol_type = other DNA
                         organism = Mus musculus
SEQUENCE: 131
gctcgaagaa ctgagactat gattacgaca gtgctatatt actatgctat ggactac       57

SEQ ID NO: 132          moltype = AA  length = 19
FEATURE                 Location/Qualifiers
source                  1..19
                        mol_type = protein
                        organism = Mus musculus
SEQUENCE: 132
ARRTETMITT VLYYYAMDY                                                   19

SEQ ID NO: 133          moltype = DNA  length = 54
FEATURE                 Location/Qualifiers
source                  1..54
                        mol_type = other DNA
                        organism = Mus musculus
SEQUENCE: 133
gctcgaagga gggaagttaa cttcggtatt aactattact attctatgga ctac           54

SEQ ID NO: 134          moltype = AA  length = 18
FEATURE                 Location/Qualifiers
source                  1..18
                        mol_type = protein
                        organism = Mus musculus
SEQUENCE: 134
ARRREVNFGI NYYYSMDY                                                    18

SEQ ID NO: 135          moltype = DNA  length = 36
FEATURE                 Location/Qualifiers
source                  1..36
                        mol_type = other DNA
                        organism = Mus musculus
SEQUENCE: 135
gtaagagatt cctatcacta cgggtacttc gatgtc                                36

SEQ ID NO: 136          moltype = AA  length = 12
FEATURE                 Location/Qualifiers
source                  1..12
                        mol_type = protein
                        organism = Mus musculus
SEQUENCE: 136
VRDSYHYGYF DV                                                          12

SEQ ID NO: 137          moltype = DNA  length = 324
FEATURE                 Location/Qualifiers
source                  1..324
                        mol_type = other DNA
                        organism = Mus musculus
SEQUENCE: 137
gacatcttgc tgactcagtc tccagccatc ctgtctgtga gtccaggaaa aagagtcagt      60
ttctcctgca gggccagtca gaacattggc acaagcatac actggtatca gcaaagaaca     120
aatggttctc caaggcttct cataaagtat gcttctaagt ctatatctgg gatttcttcc     180
aggtttagtg gcagtggctc agggacagat tttactctta gtatcaacag tgtggagtct     240
gaagatattg cagcttatta ctgtcaacat agttatagct cccgtggac gttcggtgga      300
ggcaccaagc tggaaatcaa acgg                                            324

SEQ ID NO: 138          moltype = AA  length = 108
FEATURE                 Location/Qualifiers
source                  1..108
                        mol_type = protein
                        organism = Mus musculus
SEQUENCE: 138
DILLTQSPAI LSVSPGKRVS FSCRASQNIG TSIHWYQQRT NGSPRLLIKY ASKSISGISS       60
RFSGSGSGTD FTLSINSVES EDIAAYYCQH SYSFPWTFGG GTKLEIKR                  108

SEQ ID NO: 139          moltype = DNA  length = 324
FEATURE                 Location/Qualifiers
source                  1..324
                        mol_type = other DNA
                        organism = Mus musculus
SEQUENCE: 139
gacatccaga tgactcagtc tccagcctcc ctatctacat ctgtgggaga aactgtcacc      60
atcacatgtc gagcaagtga aaatatttac agttatttag catggtatca gcagagacag     120
ggaaaatctc ctcacctcct ggtcaataat gcaaaaacct tagcagaagg tgtgccatca     180
aggttcagtg gcagtggatc aggcacacat ttttctctga ggatcagcgg cctgcagcct     240
gaagattttg gagttatta ctgtcagcat cattatggta ttccgttcac gttcggaggg      300
gggaccaagt tgtcaataaa acgg                                            324
```

-continued

```
SEQ ID NO: 140            moltype = AA   length = 108
FEATURE                   Location/Qualifiers
source                    1..108
                          mol_type = protein
                          organism = Mus musculus
SEQUENCE: 140
DIQMTQSPAS LSTSVGETVT ITCRASENIY SYLAWYQQRQ GKSPHLLVNN AKTLAEGVPS   60
RFSGSGSGTH FSLRISGLQP EDFGSYYCQH HYGIPFTFGG GTKLSIKR               108

SEQ ID NO: 141            moltype = DNA   length = 339
FEATURE                   Location/Qualifiers
source                    1..339
                          mol_type = other DNA
                          organism = Mus musculus
SEQUENCE: 141
gatgttgtga tgacccagat tccactcact ttgtcggtta ccattggaca accagcctcc   60
atctcttgca agtcaagtca gagcctcttt gatattgatg gaaagacata tttgaattgg  120
ttgttacaga ggccaggcca gtctccaaag cgcctaatct atctggtgtc tgaattggac  180
tctggagtcc ctgacaggtt cactggcagt ggatcaggga cagatttcac actgaaaatc  240
agcagagtgg aggctgagga tttgggagtt tactattgtt ggcaaggtac acattttccg  300
ctcacgttcg gtgctgggac caagctggag ctgaaacgg                         339

SEQ ID NO: 142            moltype = AA   length = 113
FEATURE                   Location/Qualifiers
source                    1..113
                          mol_type = protein
                          organism = Mus musculus
SEQUENCE: 142
DVVMTQIPLT LSVTIGQPAS ISCKSSQSLF DIDGKTYLNW LLQRPGQSPK RLIYLVSELD   60
SGVPDRFTGS GSGTDFTLKI SRVEAEDLGV YYCWQGTHFP LTFGAGTKLE LKR         113

SEQ ID NO: 143            moltype = DNA   length = 324
FEATURE                   Location/Qualifiers
source                    1..324
                          mol_type = other DNA
                          organism = Mus musculus
SEQUENCE: 143
gacatccaga tgacccagtc tccatcctcc ttatctgcct ctctgggaga aagagtcagt   60
ctcacttgtc gggcaagtca ggacattggt ggtagcttaa actggcttca gcagaaacca  120
gatggaacta ttaaacgcct gatctacgcc acatccagct tagattctgg tgtccccaaa  180
aggttcagtg gcagtaggtc tgggtcagtt ttttctctca ccatcaccag ccttgagtct  240
gaagattttg tagactattt ctgtctacaa tatgctagtt ctccgtatac gttcggaggg  300
gggaccaagc tggaaataaa acgg                                         324

SEQ ID NO: 144            moltype = AA   length = 108
FEATURE                   Location/Qualifiers
source                    1..108
                          mol_type = protein
                          organism = Mus musculus
SEQUENCE: 144
DIQMTQSPSS LSASLGERVS LTCRASQDIG GSLNWLQQKP DGTIKRLIYA TSSLDSGVPK   60
RFSGSRSGSV FSLTITSLES EDFVDYFCLQ YASSPYTFGG GTKLEIKR               108

SEQ ID NO: 145            moltype = DNA   length = 324
FEATURE                   Location/Qualifiers
source                    1..324
                          mol_type = other DNA
                          organism = Mus musculus
SEQUENCE: 145
gacattgtga tgactcagtc tccagccacc ctgtctgtga ctccaggaga tagagtctct   60
ctttcctgca gggccagcca gactattagc gacttcttac actggtatca acaaaaatca  120
catgagtctc caaggcttct catcaaatat gcttcccaat ccatctctgg gatcccctcc  180
aggttcagtg gcactggatc agggtcagat ttcactctca ctatcaacag tgtggaacct  240
gaagatgttg gagtgtatta ctgtcaaagt ggtaacacct tccgtggac gttcggtgga   300
ggcaccaagc tggaaatcaa acgg                                         324

SEQ ID NO: 146            moltype = AA   length = 108
FEATURE                   Location/Qualifiers
source                    1..108
                          mol_type = protein
                          organism = Mus musculus
SEQUENCE: 146
DIVMTQSPAT LSVTPGDRVS LSCRASQTIS DFLHWYQQKS HESPRLLIKY ASQSISGIPS   60
RFSGTGSGSD FTLTINSVEP EDVGVYYCQS GNTFPWTFGG GTKLEIKR               108

SEQ ID NO: 147            moltype = DNA   length = 324
FEATURE                   Location/Qualifiers
source                    1..324
```

```
                              mol_type = other DNA
                              organism = Mus musculus
SEQUENCE: 147
gacatccaga tgacacaatc ttcatcctcc ttttctggat ttctaggaga cagagtcacc     60
attacttgca gggcaagtga ggacatacac actcaattag cctggtatca gcagaaacca    120
ggaaatgctc ctaggctctt aaatatctggt gcagccagtt tgaaaagtgg ggttccttca    180
agattcagtg gcactggatc tggaaaggat tacactctca gcattaccag tcttcagact    240
gaagatgttg ctacatatta ctgtcaacag tataggagta ttccgtggac gttcggtgga    300
ggcaccaagc tggaaatcaa acgg                                            324

SEQ ID NO: 148            moltype = AA   length = 108
FEATURE                   Location/Qualifiers
source                    1..108
                          mol_type = protein
                          organism = Mus musculus
SEQUENCE: 148
DIQMTQSSSS FSGFLGDRVT ITCRASEDIH TQLAWYQQKP GNAPRLLISG AASLKSGVPS     60
RFSGTGSGKD YTLSITSLQT EDVATYYCQQ YRSIPWTFGG GTKLEIKR                 108

SEQ ID NO: 149            moltype = DNA   length = 339
FEATURE                   Location/Qualifiers
source                    1..339
                          mol_type = other DNA
                          organism = Mus musculus
SEQUENCE: 149
gatgtttga tgacccaaac tccgctctcc ctgcctgtca gtcttggaga tcacgcctcc      60
atctcttgca gatctagtca gtacattgtt catagtactg gaaccaccta tttagaatgg    120
tacctacaga aaccaggcca gtctccacag ctcctgatct acaaagtttc caaccgattt    180
tctggggtcc cagacaggtt cactggcagt ggatcaggga cagatttcac actcaggatc    240
agcagagtgg aggctgagga tctgggagtt tatttctgct ttcaaggttc acattttcca    300
ttcacgttcg gctcggggac aaagttggaa ataaaacgg                            339

SEQ ID NO: 150            moltype = AA   length = 113
FEATURE                   Location/Qualifiers
source                    1..113
                          mol_type = protein
                          organism = Mus musculus
SEQUENCE: 150
DVLMTQTPLS LPVSLGDHAS ISCRSSQYIV HSTGTTYLEW YLQKPGQSPQ LLIYKVSNRF     60
SGVPDRFTGS GSGTDFTLRI SRVEAEDLGV YFCFQGSHFP FTFGSGTKLE IKR            113

SEQ ID NO: 151            moltype = DNA   length = 339
FEATURE                   Location/Qualifiers
source                    1..339
                          mol_type = other DNA
                          organism = Mus musculus
SEQUENCE: 151
gaagttgtga tgacccaaac tccactctcc ttgcctgtca gtcttggaga tcaagcctcc      60
atctcttgca gatctagtca ttaccttgtt catgataacg gaaacaccta tgttgaatgg    120
tacctgcaga agccaggcca gtctccaaag ctcctgatct acaaagtttc caaccgattt    180
tctggagtcc cagacaggtt tactggcagt ggttcaggga cagatttcac actcaagatc    240
agcagagtgg agtctgagga tctgggaatt tattactgct ttcaaggttc acatttccca    300
ttcacgttcg gctcggggac agagttggaa ataaaacgg                            339

SEQ ID NO: 152            moltype = AA   length = 113
FEATURE                   Location/Qualifiers
source                    1..113
                          mol_type = protein
                          organism = Mus musculus
SEQUENCE: 152
EVVMTQTPLS LPVSLGDQAS ISCRSSHYLV HDNGNTYVEW YLQKPGQSPK LLIYKVSNRF     60
SGVPDRFTGS GSGTDFTLKI SRVESEDLGI YYCFQGSHFP FTFGSGTELE IKR            113

SEQ ID NO: 153            moltype = DNA   length = 339
FEATURE                   Location/Qualifiers
source                    1..339
                          mol_type = other DNA
                          organism = Mus musculus
SEQUENCE: 153
gatgttttga tgacccaaac tccactctcc ctgcctgtca gtcttggaga tcaagcctcc      60
atctcttgca gatctagtca gaacattgtc catagtactg gaaacaccta tttagaatgg    120
tacctgcaga aaccaggcca gtctccaaag ctcctgattt ataaagtttc caaccgattt    180
tctggggtcc caaacaggtt ccgtggcagt ggatcaggga cagatttcac actcaagatc    240
accagagtgg aggctgagga tctgggaatt tattactgct ttcaaggttc acattttcca    300
ttcacgttcg gctcggggac aaagttggaa ataaaacgg                            339

SEQ ID NO: 154            moltype = AA   length = 113
FEATURE                   Location/Qualifiers
source                    1..113
```

```
                        mol_type = protein
                        organism = Mus musculus
SEQUENCE: 154
DVLMTQTPLS LPVSLGDQAS ISCRSSQNIV HSTGNTYLEW YLQKPGQSPK LLIYKVSNRF   60
SGVPNRFRGS GSGTDFTLKI TRVEAEDLGI YYCFQGSHFP FTFGSGTKLE IKR          113

SEQ ID NO: 155         moltype = DNA   length = 321
FEATURE                Location/Qualifiers
source                 1..321
                        mol_type = other DNA
                        organism = Mus musculus
SEQUENCE: 155
caaattgttc tcacccagtc tccagcaatc atgtctgcat ctccagggga gaaggtcacc   60
atgacctgca gtgtcagctc aagtgtaagt tacatacact ggtaccaaca gaagtcaggc  120
acctccccca aaagatggat ttatgacaca tccaaactgg cttctggagt ccctgctcgc  180
ttcagtggca gtgggtctgg gacctcttac tctctcacaa tcagcagcat ggaggctgaa  240
gatgctgcca cttattactg ccaccagtgg agtactaacc cacccacgtt cggagggggg  300
accaagctgg aaataagacg g                                           321

SEQ ID NO: 156         moltype = AA   length = 107
FEATURE                Location/Qualifiers
source                 1..107
                        mol_type = protein
                        organism = Mus musculus
SEQUENCE: 156
QIVLTQSPAI MSASPGEKVT MTCSVSSSVS YIHWYQQKSG TSPKRWIYDT SKLASGVPAR   60
FSGSGSGTSY SLTISSMEAE DAATYYCHQW STNPPTFGGG TKLEIRR                107

SEQ ID NO: 157         moltype = DNA   length = 321
FEATURE                Location/Qualifiers
source                 1..321
                        mol_type = other DNA
                        organism = Mus musculus
SEQUENCE: 157
caaattgttc tcacccagtc tccagcactc atgtctgcat ctccagggga gaaggtcacc   60
atgacctgca gtgccagctc aagtgtaagt tacatgtgct ggtaccagca gaagccaaga  120
tcctccccca aaccctggat ttatctcaca tccaacctgg cttctggagt ccctgctcgc  180
ttcagtggca gtgggtctgg gacctcttac tctctcacaa tcagtagcat ggaggctgaa  240
gatgctgcca cttattactg ccagcagtgg agtagtaacc cacccacgtt cggtgctggg  300
accaagctgg agctgaaacg g                                           321

SEQ ID NO: 158         moltype = AA   length = 107
FEATURE                Location/Qualifiers
source                 1..107
                        mol_type = protein
                        organism = Mus musculus
SEQUENCE: 158
QIVLTQSPAL MSASPGEKVT MTCSASSSVS YMCWYQQKPR SSPKPWIYLT SNLASGVPAR   60
FSGSGSGTSY SLTISSMEAE DAATYYCQQW SSNPPTFGAG TKLELKR                107

SEQ ID NO: 159         moltype = DNA   length = 321
FEATURE                Location/Qualifiers
source                 1..321
                        mol_type = other DNA
                        organism = Mus musculus
SEQUENCE: 159
gaaatccaga tgacacagac tccatcctcc ctgtctgcct ctctgggaga cagagtcacc   60
atcacttgca gtgcaagtca gggcattaac aattatttga actggtatca gcagaaacca  120
ggtggaaaga ctagactcct catctattat acatcaactt tacagtcagg agtcccatca  180
aggttcagtg gcagtgggtc tgggacacat tattctctca ccatcagcaa tctggaacct  240
gaagatattg ccacttacta ttgtcagcag tttagtaaac ttcggacatt cggtggaggc  300
accaggctgg aaatcaaacg g                                           321

SEQ ID NO: 160         moltype = AA   length = 107
FEATURE                Location/Qualifiers
source                 1..107
                        mol_type = protein
                        organism = Mus musculus
SEQUENCE: 160
EIQMTQTPSS LSASLGDRVT ITCSASQGIN NYLNWYQQKP GGKTRLLIYY TSTLQSGVPS   60
RFSGSGSGTH YSLTISNLEP EDIATYYCQQ FSKLRTFGGG TRLEIKR                107

SEQ ID NO: 161         moltype = DNA   length = 324
FEATURE                Location/Qualifiers
misc_feature           128
                        note = MISC_FEATURE - n at position 128 is c or a
source                 1..324
                        mol_type = other DNA
                        organism = Homo sapiens
```

```
SEQUENCE: 161
gagattgtgc tgactcagag tccagacttc cagtcagtga cccccaagga gaaagtcacc    60
atcacatgcc gggcaagcca gaacatcggc acaagcattc actggtacca gcagaagccc   120
gatcagtncc ctaagctgct gatcaaatat gcctctaaga gtatttcagg ggtgccctct   180
agattcagcg gctccgggtc tggaacagac tttactctga ccattaactc cctggaggct   240
gaagatgccg ctacttacta ttgtcagcat agctactcat tcccttggac attcgggcag   300
gggaccaaag tggaaatcaa acgt                                          324

SEQ ID NO: 162           moltype = AA   length = 108
FEATURE                  Location/Qualifiers
VARIANT                  43
                         note = MISC_FEATURE - Xaa at position 43 is Ser or Tyr
source                   1..108
                         mol_type = protein
                         organism = Homo sapiens
SEQUENCE: 162
EIVLTQSPDF QSVTPKEKVT ITCRASQNIG TSIHWYQQKP DQXPKLLIKY ASKSISGVPS    60
RFSGSGSGTD FTLTINSLEA EDAATYYCQH SYSFPWTFGQ GTKVEIKR                108

SEQ ID NO: 163           moltype = DNA   length = 339
FEATURE                  Location/Qualifiers
source                   1..339
                         mol_type = other DNA
                         organism = Homo sapiens
SEQUENCE: 163
gatattgtga tgacccaaac tccgctctcc ctgtccgtca cccctggaca gccggcctcc    60
atctcttgca gatctagtca gaacattgtt catagtactg aaacaccta tttagaatgg     120
tacctacaga aaccaggcca gtctccacag ctcctgatct acaaagtttc caaccgattt    180
tctgggtcc cagacaggtt cagtggcagt ggatcaggga cagatttcac actcaaaatc     240
agcagagtgg aggctgagga tgttggagtt tattactgct ttcaaggttc acattttcca    300
ttcacgttcg gccaagggac caaggtggaa atcaaacgt                          339

SEQ ID NO: 164           moltype = AA   length = 113
FEATURE                  Location/Qualifiers
source                   1..113
                         mol_type = protein
                         organism = Homo sapiens
SEQUENCE: 164
DIVMTQTPLS LSVTPGQPAS ISCRSSQNIV HSTGNTYLEW YLQKPGQSPQ LLIYKVSNRF    60
SGVPDRFSGS GSGTDFTLKI SRVEAEDVGV YYCFQGSHFP FTFGQGTKVE IKR          113

SEQ ID NO: 165           moltype = DNA   length = 360
FEATURE                  Location/Qualifiers
source                   1..360
                         mol_type = other DNA
                         organism = Mus musculus
SEQUENCE: 165
caggttactc tgaaagagtc tggccctggg atattgcagc cctcccagac cctcagtctg    60
acttgttctt ctctgggtt ctcactgacc acttctggct tgggtgttgc ctggattcgt     120
cagccttcag ggaagggtct ggagtggctg gcacacattt ggtcggatgg tgacacgcgc    180
tattacccag ccctgaagaa ccgactgaca atctccaagg attcctccag caaccaggtc    240
ttcctcaaga tcgcccgtgt ggacactgca gatactgcca catactactg tgctcgaatc    300
aaggatgata gtctttactt tgacaactgg ggccaaggca ctattttcac agtctcctca    360

SEQ ID NO: 166           moltype = AA   length = 120
FEATURE                  Location/Qualifiers
source                   1..120
                         mol_type = protein
                         organism = Mus musculus
SEQUENCE: 166
QVTLKESGPG ILQPSQTLSL TCSFSGFSLT TSGLGVAWIR QPSGKGLEWL AHIWSDGDTR    60
YYPALKNRLT ISKDSSSNQV FLKIARVDTA DTATYYCARM KDDSLYFDNW GQGTIFTVSS   120

SEQ ID NO: 167           moltype = DNA   length = 351
FEATURE                  Location/Qualifiers
source                   1..351
                         mol_type = other DNA
                         organism = Mus musculus
SEQUENCE: 167
cagatccagt tggtgcagtc tggggctgaa ctggcaaaac ctggggcctc agtgaggatg    60
tcctgcgaga cttctggcta cacctttact agctactgga tacactggat aaaagagagg   120
cctggacagg gtctggaatg gattggatac attaatcctg acactgatta tagtgagtac    180
aatcagaaat tcaaggacaa ggccagattg actgcagaca atcctccac cacagcctac     240
atggagctga cagcctgac atttgatgat tctgcagtct attactgtgc aagtgctggt     300
tattatttt ttgacttctg gggccaaggc accactctca gtctcctc a               351

SEQ ID NO: 168           moltype = AA   length = 117
FEATURE                  Location/Qualifiers
source                   1..117
```

```
                              mol_type = protein
                              organism = Mus musculus
SEQUENCE: 168
QIQLVQSGAE LAKPGASVRM SCETSGYTFT SYWIHWIKER PGQGLEWIGY INPDTDYSEY   60
NQKFKDKARL TADKSSTTAY MELNSLTFDD SAVYYCASAG YYFFDFWGQG TTLTVSS      117

SEQ ID NO: 169               moltype = DNA   length = 336
FEATURE                      Location/Qualifiers
source                       1..336
                             mol_type = other DNA
                             organism = Mus musculus
SEQUENCE: 169
gaggttcagc tgcagcagtc tggggcagaa cttgtgaaac caggggcctc agtcaagttg   60
tcctgtacaa cttctggcct caacattaaa gacatctata ttcactgggt gaagcagagg  120
cctgaacagg gcctggagtg gattgggagg attgatcctg cgaacggtaa gactgcatat  180
gacctgaagt tccaggccaa ggccactata acagcagaca catcttccaa aacagcctac  240
ctgcacctca gcagcctgac atctgaggac actgccgtct attactgtgg tagggggggcc  300
cactggggcc aaggcaccac tctcacagtc tcctca                            336

SEQ ID NO: 170               moltype = AA   length = 112
FEATURE                      Location/Qualifiers
source                       1..112
                             mol_type = protein
                             organism = Mus musculus
SEQUENCE: 170
EVQLQQSGAE LVKPGASVKL SCTTSGLNIK DIYIHWVKQR PEQGLEWIGR IDPANGKTAY   60
DLKFQAKATI TADTSSKTAY LHLSSLTSED TAVYYCGRGA HWGQGTTLTV SS          112

SEQ ID NO: 171               moltype = DNA   length = 354
FEATURE                      Location/Qualifiers
source                       1..354
                             mol_type = other DNA
                             organism = Mus musculus
SEQUENCE: 171
cagatccagt tggtgcagtc tgggcctcag ctggttaggc ctggggcttc agtgaagata   60
tcctgcgagg cttctggtta ctcattcacc aactactgga tacactgggt gaagcagagg  120
cctgacagg gtcttgagtg gattggcatg attgatcctt ccgatgctga aactgggtta  180
aatcagaagt tcaaggacaa ggccacattg actgtagaca atcctccag cacagcctac  240
atgcaactca gcagcccgac atctgaagac tctgcggtct attactgtgc aagaattggc  300
gattactata atatggacta ctggggtcaa ggaacctcag tcaccgtctc ctca        354

SEQ ID NO: 172               moltype = AA   length = 118
FEATURE                      Location/Qualifiers
source                       1..118
                             mol_type = protein
                             organism = Mus musculus
SEQUENCE: 172
QIQLVQSGPQ LVRPGASVKI SCEASGYSFT NYWIHWVKQR PGQGLEWIGM IDPSDAETGL   60
NQKFKDKATL TVDKSSTAY MQLSSPTSED SAVYYCARIG DYYNMDYWGQ GTSVTVSS     118

SEQ ID NO: 173               moltype = DNA   length = 366
FEATURE                      Location/Qualifiers
source                       1..366
                             mol_type = other DNA
                             organism = Mus musculus
SEQUENCE: 173
gaagtgaagg tggtggagtc tgggggaggt ttagtgcagc ctggagggtc cctgaaactc   60
tcctgtgcag cctctggatt cactttcagt gactatccca tgtcttgggt tcgccagact  120
ccagagaaga gactggagtg ggtcgcatac gttagtgatg gtggtggttc cacctactat  180
ccagacattg taaagggccg attcaccatc tcccgagaca tgccaagaa caccctgtac  240
cttcaaatga gcagtctgaa gtctgaggac acggccatgt atttctgtac aagacatgct  300
tcctactata gctacgacca ttctatggac tactggggtc agggaacctc agtcaccgtc  360
tcatca                                                             366

SEQ ID NO: 174               moltype = AA   length = 122
FEATURE                      Location/Qualifiers
source                       1..122
                             mol_type = protein
                             organism = Mus musculus
SEQUENCE: 174
EVKVVESGGG LVQPGGSLKL SCAASGFTFS DYPMSWVRQT PEKRLEWVAY VSDGGGSTYY   60
PDIVKGRFTI SRDNAKNTLY LQMSSLKSED TAMYFCTRHA SYYSYDHSMD YWGQGTSVTV  120
SS                                                                 122

SEQ ID NO: 175               moltype = DNA   length = 357
FEATURE                      Location/Qualifiers
source                       1..357
                             mol_type = other DNA
                             organism = Mus musculus
```

```
SEQUENCE: 175
cagatccagt tggtgcagtc tggggggagac ttagtgaggc ctggagggtc cctgaaactc    60
tcctgtgcag cctctggatt cactttcagt agctttggca tgtcttggat tcgccagact    120
ccagacaaga ggctggagtg ggtcgcaacc attagtagtg ctggtagttt cacctactat    180
ccagacagtg tgaagggccg attcaccatc tccagagaca atgccaggaa caccctgtat    240
ctacaaatga acagtctgaa gtctgaggac tcagccatgt attactgtgc aagacggggg    300
tacgacgttg ggtgctttga ccactgggc cgaggcacca ctctcacagt ctcctca        357

SEQ ID NO: 176          moltype = AA   length = 119
FEATURE                 Location/Qualifiers
source                  1..119
                        mol_type = protein
                        organism = Mus musculus
SEQUENCE: 176
QIQLVQSGGD LVRPGGSLKL SCAASGFTFS SFGMSWIRQT PDKRLEWVAT ISSAGSFTYY    60
PDSVKGRFTI SRDNARNTLY LQMNSLKSED SAMYYCARRG YDVGCFDHWG RGTTLTVSS     119

SEQ ID NO: 177          moltype = DNA   length = 348
FEATURE                 Location/Qualifiers
source                  1..348
                        mol_type = other DNA
                        organism = Mus musculus
SEQUENCE: 177
gaggtgcacc tggtggagtc tggggggaggc ttagtgcagc ctggagggtc cctgaaactc    60
tcctgtgcag cctctggatt cactttcagt acctatggca tgtcttgggt tcgccagact    120
ccagacaaga ggctggagtt ggtcgcgacc attaatacta atggtggtac cacctattat    180
cgagacagtg tgaagggccg attcaccatc tccagagaca atgccaagaa caccctgtac    240
ctgcaaatga gcagtctgaa gtctgatgac acagccatgt attactgtgc aagagactac    300
ggggctatgg actactgggg tcaaggaacc tcagtcaccg tctcctca                348

SEQ ID NO: 178          moltype = AA   length = 116
FEATURE                 Location/Qualifiers
source                  1..116
                        mol_type = protein
                        organism = Mus musculus
SEQUENCE: 178
EVHLVESGGG LVQPGGSLKL SCAASGFTFS TYGMSWVRQT PDKRLELVAT INTNGGTTYY    60
RDSVKGRFTI SRDNAKNTLY LQMSSLKSDD TAMYYCARDY GAMDYWGQGT SVTVSS        116

SEQ ID NO: 179          moltype = DNA   length = 345
FEATURE                 Location/Qualifiers
source                  1..345
                        mol_type = other DNA
                        organism = Mus musculus
SEQUENCE: 179
gatgtgcacc tggtggagtc tggggggaggc ttagtgcagc ctggagggtc cctgacagtc    60
tcctgcgcag cctctggatt cactttcagt acctatggca tgtcttgggt tcgccagact    120
cgagacaaga ggctggagtt ggtcgcaacc ataaatacta atggtggtaa cacctattat    180
tcagacaatg tgaagggccg attcaccatt tccagagaca atgccaagaa caccctgtat    240
ttggaaatga gaggtctgag gtctgggac acagccatgt attactgtgc aagagactac    300
ggggctatgg actactgggg tcaaggaacc tcagtcaccg tctct                   345

SEQ ID NO: 180          moltype = AA   length = 115
FEATURE                 Location/Qualifiers
source                  1..115
                        mol_type = protein
                        organism = Mus musculus
SEQUENCE: 180
DVHLVESGGG LVQPGGSLTV SCAASGFTFS TYGMSWVRQT RDKRLELVAT INTNGGNTYY    60
SDNVKGRFTI SRDNAKNTLY LEMRGLRSGD TAMYYCARDY GAMDYWGQGT SVTVS         115

SEQ ID NO: 181          moltype = DNA   length = 348
FEATURE                 Location/Qualifiers
source                  1..348
                        mol_type = other DNA
                        organism = Mus musculus
SEQUENCE: 181
gaggtgcagc tgcagcagcc tggggggaggc ttagtacagc ctggagggtc cctgacactc    60
tcctgtgcaa cctctggatt cactttcagt agttatggca tgtcttgggt tcgccagact    120
ccagccaaga ggctggagtt ggtcgcaacc attagtacta atggtgccac cgccaattat    180
ccagacagtg tgaagggccg attcaccatc tccagagaca atgccaagag caccctgtac    240
ctacaaatgc gcagtctgaa gtctgaggac acagccatgt attactgtgc aactgaaaag    300
ggagctatgg gctactgggg tcaaggaacc tcagtcaccg tctcctca                348

SEQ ID NO: 182          moltype = AA   length = 116
FEATURE                 Location/Qualifiers
source                  1..116
                        mol_type = protein
                        organism = Mus musculus
```

```
SEQUENCE: 182
EVQLQQPGGG LVQPGGSLTL SCATSGFTFS SYGMSWVRQT PAKRLELVAT ISTNGATANY   60
PDSVKGRFTI SRDNAKSTLY LQMRSLKSED TAMYYCATEK GAMGYWGQGT SVTVSS        116

SEQ ID NO: 183            moltype = DNA   length = 381
FEATURE                   Location/Qualifiers
source                    1..381
                          mol_type = other DNA
                          organism = Mus musculus
SEQUENCE: 183
caagttactc taaaagagtc tggccctggg atattgaagc cctcacagac cctcagtctg   60
acttgttctt tctctgggtt ttcactgacc acttctggta tgggtgtagg ctggattcgt  120
cagccttcag ggaagggtct ggagtggctg gcacacattt ggtgggatga tgataagtac  180
tataatccat ccctgaagag ccaggtcaca atctccaagg acacctccag aaaccaggta  240
ttcctcaaga tcaccagtgt ggacactgca gatactgcca cttactactg tgctcgaaga  300
actgagacta tgattacgac agtgctatat tactatgcta tggactactg gggtcaagga  360
acctcagtca ccgtctcctc a                                            381

SEQ ID NO: 184            moltype = AA   length = 127
FEATURE                   Location/Qualifiers
source                    1..127
                          mol_type = protein
                          organism = Mus musculus
SEQUENCE: 184
QVTLKESGPG ILKPSQTLSL TCSFSGFSLT TSGMGVGWIR QPSGKGLEWL AHIWWDDDKY   60
YNPSLKSQVT ISKDTSRNQV FLKITSVDTA DTATYYCARR TETMITTVLY YYAMDYWGQG  120
TSVTVSS                                                            127

SEQ ID NO: 185            moltype = DNA   length = 378
FEATURE                   Location/Qualifiers
source                    1..378
                          mol_type = other DNA
                          organism = Mus musculus
SEQUENCE: 185
caagttactc taaaagagtc tggccctggg atattgaagc cctcacagac cctcagtctg   60
acttgttctt tctctggatt ttcactgagc acttctggtt tgggtgtagg ctggattcgt  120
cagccttcag ggaagggtct ggagtggctg gcacacattt ggtgggatga tgataagtac  180
tataatccat cccttaagag acagatcaca atctccaagg attcctccag aaaccaggta  240
ttcctcaaga tcaccaatgt ggacactgca gatactgcca cttactactg tgctcgaagg  300
agggaagtta acttcggtat taactattac tattctatgg actactgggg tcaaggaacc  360
tcagtcaccg tctcctca                                                378

SEQ ID NO: 186            moltype = AA   length = 126
FEATURE                   Location/Qualifiers
source                    1..126
                          mol_type = protein
                          organism = Mus musculus
SEQUENCE: 186
QVTLKESGPG ILKPSQTLSL TCSFSGFSLS TSGLGVGWIR QPSGKGLEWL AHIWWDDDKY   60
YNPSLKRQIT ISKDSSRNQV FLKITNVDTA DTATYYCARR REVNFGINYY YSMDYWGQGT  120
SVTVSS                                                             126

SEQ ID NO: 187            moltype = DNA   length = 363
FEATURE                   Location/Qualifiers
source                    1..363
                          mol_type = other DNA
                          organism = Mus musculus
SEQUENCE: 187
gaggtgaagc tggtggagtc tggaggacgc ttggtacagc ctgggaattc tctgagactc   60
tcctgtgcaa cttctggatt caccttcagt gattattaca tgagttgggt ccgccagact  120
ccaggaaggg cacttgagtg gttgagtttt attagaaatc gggctaatgg ttacacaaca  180
gagtacagtg catctgtgaa gggtcgattc accatctcca gagataattc caaagcatc   240
ctctatcttc acatgagcac cctgagacct gaggacagtg ccacttatta ctgtgtaaga  300
gattcctatc actacgggta cttcgatgtc tggggcgcag gaccacggt caccgtctcc  360
tca                                                                363

SEQ ID NO: 188            moltype = AA   length = 121
FEATURE                   Location/Qualifiers
source                    1..121
                          mol_type = protein
                          organism = Mus musculus
SEQUENCE: 188
EVKLVESGGR LVQPGNSLRL SCATSGFTFS DYYMSWVRQT PGRALEWLSF IRNRANGYTT   60
EYSASVKGRF TISRDNSQSI LYLHMSTLRP EDSATYYCVR DSYHGYFDV WGAGTTVTVS   120
S                                                                  121

SEQ ID NO: 189            moltype = DNA   length = 360
FEATURE                   Location/Qualifiers
source                    1..360
```

```
                              mol_type = other DNA
                              organism = Homo sapiens
SEQUENCE: 189
caggtgaccc tgaaggaatc cgggcctact ctggtgaaac ctacccagac tctgactctg    60
acttgtactt ttagcggctt ctcactgacc acatctggac tgggagtggc ttggatcaga   120
cagcctcctg gaaaggccct ggagtggctg gctcacattt ggagcgacgg cgatactcgg   180
tactatccag ccctgaaaaa cagactgact atcaccaagg acacatccaa aaaccaggtg   240
gtcctgacaa tgactaatat ggaccccgtc gataccgcaa catactattg cgcccatatg   300
aaggatgact ctctgtactt tgataactgg gggcagggga ctctggtgac cgtgagcagc   360

SEQ ID NO: 190              moltype = AA  length = 120
FEATURE                     Location/Qualifiers
source                      1..120
                            mol_type = protein
                            organism = Homo sapiens
SEQUENCE: 190
QVTLKESGPT LVKPTQTLTL TCTFSGFSLT TSGLGVAWIR QPPGKALEWL AHIWSDGDTR    60
YYPALKNRLT ITKDTSKNQV VLTMTNMDPV DTATYYCAHM KDDSLYFDNW GQGTLVTVSS   120

SEQ ID NO: 191              moltype = DNA  length = 348
FEATURE                     Location/Qualifiers
source                      1..348
                            mol_type = other DNA
                            organism = Homo sapiens
SEQUENCE: 191
gaggtgcagc tgctggaatc tggggggggga ctggtgcagc ctggaggaag cctgagactg    60
agttgtgccg caagtgggtt tacatttagc tcctacggaa tgagctgggt gaggcaggct   120
ccaggcaagg gactggagtg ggtctctgca atcagtacca acggagccac agcttactat   180
gccgactccg tgaagggccg gttcactatc tcaagagata acagcaagaa caccctgtat   240
ctgcagatga attctctgcg ggcagaagac acagccgtct actattgcgc tactgagaaa   300
ggggcaatga gccactgggg acagggcaca ctggtgaccg tgagttcc                348

SEQ ID NO: 192              moltype = AA  length = 116
FEATURE                     Location/Qualifiers
source                      1..116
                            mol_type = protein
                            organism = Homo sapiens
SEQUENCE: 192
EVQLLESGGG LVQPGGSLRL SCAASGFTFS SYGMSWVRQA PGKGLEWVSA ISTNGATAYY    60
ADSVKGRFTI SRDNSKNTLY LQMNSLRAED TAVYYCATEK GAMSHWGQGT LVTVSS       116

SEQ ID NO: 193              moltype = DNA  length = 318
FEATURE                     Location/Qualifiers
source                      1..318
                            mol_type = other DNA
                            organism = Mus musculus
SEQUENCE: 193
gctgatgctg caccaactgt atccatcttc ccaccatcca gtgagcagtt aacatctgga    60
ggtgcctcag tcgtgtgctt cttgaacaac ttctacccca aagacatcaa tgtcaagtgg   120
aagattgatg gcagtgaacg acaaaatggc gtcctgaaca gttggactga tcaggacagc   180
aaagacagca cctacagcat gagcagcacc ctcacgttga ccaaggacga gtatgaacga   240
cataacagct atacctgtga ggccactcac aagacatcaa cttcacccat tgtcaagagc   300
ttcaacagga atgagtgt                                                 318

SEQ ID NO: 194              moltype = AA  length = 106
FEATURE                     Location/Qualifiers
source                      1..106
                            mol_type = protein
                            organism = Mus musculus
SEQUENCE: 194
ADAAPTVSIF PPSSEQLTSG GASVVCFLNN FYPKDINVKW KIDGSERQNG VLNSWTDQDS    60
KDSTYSMSST LTLTKDEYER HNSYTCEATH KTSTSPIVKS FNRNEC                  106

SEQ ID NO: 195              moltype = DNA  length = 315
FEATURE                     Location/Qualifiers
source                      1..315
                            mol_type = other DNA
                            organism = Mus musculus
SEQUENCE: 195
ggtcagccca agtccactcc cactctcacc gtgtttccac cttcctctga ggagctcaag    60
gaaaacaaag ccacactggt gtgtctgatt tccaactttt ccccgagtgg tgtgacagtg   120
gcctggaagg caaatggtac acctatcacc caggtgtgg acacttcaaa tcccaccaaa   180
gagggcaaca agttcatggc cagcagcttc ctacatttga tcatcggacca gtggagatct   240
cacaacagtt ttacctgtca agttacacat gaaggggaca ctgtggagaa gagtctgtct   300
cctgcagaat gtctc                                                    315

SEQ ID NO: 196              moltype = AA  length = 105
FEATURE                     Location/Qualifiers
source                      1..105
```

-continued

```
                              mol_type = protein
                              organism = Mus musculus
SEQUENCE: 196
GQPKSTPTLT VFPPSSEELK ENKATLVCLI SNFSPSGVTV AWKANGTPIT QGVDTSNPTK    60
EGNKFMASSF LHLTSDQWRS HNSFTCQVTH EGDTVEKSLS PAECL                    105

SEQ ID NO: 197            moltype = DNA   length = 975
FEATURE                   Location/Qualifiers
source                    1..975
                          mol_type = other DNA
                          organism = Mus musculus
SEQUENCE: 197
gccaaaacaa cagccccatc ggtctatcca ctggcccctg tgtgtggaga tacaactggc    60
tcctcggtga ctctaggatg cctggtcaag ggttatttcc ctgagccagt gaccttgacc   120
tggaactctg gatccctgtc cagcggtgtg cacaccttcc cagctgtcct gcagtctgac   180
ctctacactc tgagcagctc agtgactgtc ccctccagca cctggcccag cgagaccgtc   240
acctgcaacg ttgcccaccc ggccagcagc accaaggtgg acaagaaaat tgtgcccagg   300
gattgtggtt gtaagccttg catatgtaca gtcccagaag tatcatctgt cttcatcctg   360
cccccaaagc ccaaggatgt gctcaccatt actctgactc ctaaggtcac gtgtgttgtg   420
gtagacatca gcaaggatga tcccgaggtc cagttcagct ggtttgtaga tgatgtggag   480
gtgcacacag ctcagacgca accccgggag gagcagttca acagcacttt ccgctcagtc   540
agtgaacttc ccatcatgca ccaggactgg ctcaatggca aggagttcaa atgcagggtc   600
aacagtgcag ctttccctgc ccccatcgag aaaaccatct ccaaaaccaa aggcagaccg   660
aaggctccac aggtgtacac cattccacct cccaaggagc agatggccaa ggataaagtc   720
agtctgacct gcatgataac agacttcttc cctgaagaca ttactgtgga gtggcagtgg   780
aatgggcagc cagcggagaa ctacaagaac actcagccca tcatggacac agatggctct   840
tacttcgtct acagcaagct caatgtgcag aagagcaact gggaggcagg aaatactttc   900
acctgctctg tgttacatga gggcctgcac aaccaccata ctgagaagag cctctcccac   960
tctcctggta aaggc                                                    975

SEQ ID NO: 198            moltype = AA   length = 325
FEATURE                   Location/Qualifiers
source                    1..325
                          mol_type = protein
                          organism = Mus musculus
SEQUENCE: 198
AKTTAPSVYP LAPVCGDTTG SSVTLGCLVK GYFPEPVTLT WNSGSLSSGV HTFPAVLQSD    60
LYTLSSSVTV PSSTWPSETV TCNVAHPASS TKVDKKIVPR DCGCKPCICT VPEVSSVFIF   120
PPKPKDVLTI TLTPKVTCVV VDISKDDPEV QFSWFVDDVE VHTAQTQPRE EQFNSTFRSV   180
SELPIMHQDW LNGKEFKCRV NSAAFPAPIE KTISKTKGRP KAPQVYTIPP PKEQMAKDKV   240
SLTCMITDFF PEDITVEWQW NGQPAENYKN TQPIMDTDGS YFVYSKLNVQ KSNWEAGNTF   300
TCSVLHEGLH NHHTEKSLSH SPGKG                                         325

SEQ ID NO: 199            moltype = DNA   length = 20
FEATURE                   Location/Qualifiers
source                    1..20
                          mol_type = other DNA
                          note = MISC_FEATURE - Primer
                          organism = synthetic construct
SEQUENCE: 199
tttggrggga agatgaagac                                                20

SEQ ID NO: 200            moltype = DNA   length = 21
FEATURE                   Location/Qualifiers
source                    1..21
                          mol_type = other DNA
                          note = MISC_FEATURE - Primer
                          organism = synthetic construct
SEQUENCE: 200
ttaacactct cccctgttga a                                              21

SEQ ID NO: 201            moltype = DNA   length = 21
FEATURE                   Location/Qualifiers
source                    1..21
                          mol_type = other DNA
                          note = MISC_FEATURE - Primer
                          organism = synthetic construct
SEQUENCE: 201
ttaacactca ttcctgttga a                                              21

SEQ ID NO: 202            moltype = DNA   length = 21
FEATURE                   Location/Qualifiers
source                    1..21
                          mol_type = other DNA
                          note = MISC_FEATURE - Primer
                          organism = synthetic construct
SEQUENCE: 202
tggacaggga tccagagttc c                                              21
```

-continued

```
SEQ ID NO: 203        moltype = DNA   length = 21
FEATURE               Location/Qualifiers
source                1..21
                      mol_type = other DNA
                      note = MISC_FEATURE - Primer
                      organism = synthetic construct
SEQUENCE: 203
tggacagggc tccatagttc c                                         21

SEQ ID NO: 204        moltype = DNA   length = 20
FEATURE               Location/Qualifiers
source                1..20
                      mol_type = other DNA
                      note = MISC_FEATURE - Primer
                      organism = synthetic construct
SEQUENCE: 204
actcgtcctt ggtcaacgtg                                           20
```